United States Patent
Beaucage et al.

(10) Patent No.: US 10,087,465 B2
(45) Date of Patent: Oct. 2, 2018

(54) TRANS-ACTING ELEMENTS FOR INTRACELLULAR DELIVERY OF NUCLEIC ACID SEQUENCES

(71) Applicant: The United States of America, as Represented by the Secretary of the Department of Health and Human Services, Washington, DC (US)

(72) Inventors: Serge L. Beaucage, Silver Spring, MD (US); Harsh V. Jain, Silver Spring, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/265,436

(22) Filed: Sep. 14, 2016

(65) Prior Publication Data

US 2017/0130246 A1    May 11, 2017

Related U.S. Application Data

(63) Continuation-in-part of application No. PCT/US2015/020402, filed on Mar. 13, 2015.

(60) Provisional application No. 61/952,928, filed on Mar. 14, 2014.

(51) Int. Cl.
| | |
|---|---|
| *C07H 21/04* | (2006.01) |
| *C12N 15/11* | (2006.01) |
| *C12N 15/113* | (2010.01) |
| *C12N 15/87* | (2006.01) |
| *C12N 15/90* | (2006.01) |

(52) U.S. Cl.
CPC .......... *C12N 15/907* (2013.01); *C07H 21/04* (2013.01); *C12N 15/11* (2013.01); *C12N 15/113* (2013.01); *C12N 15/87* (2013.01); *C12N 2310/14* (2013.01); *C12N 2310/3181* (2013.01); *C12N 2310/3233* (2013.01)

(58) Field of Classification Search
CPC ...... C07H 21/04; C12N 15/11; C12N 15/113; C12N 15/87; C12N 15/907; C12N 2310/14; C12N 2310/3181; C12N 2310/3233
USPC ...................... 435/91.1; 536/25.32, 25.6, 4.1
See application file for complete search history.

(56) References Cited

FOREIGN PATENT DOCUMENTS

WO    2015138868 A9    9/2015

OTHER PUBLICATIONS

Grajkowski, The 2-N-Formyl-N-methyl)aminoethyl Group as a Potential Phosphate/Thiophosphate Protecting Group in Solid-Phase Oligodeoxyribonucleotide Synthesis, Org. Lett., 3: 1287-1290 (2001).*
Cieślak et al. (#1), Thermolytic 4-Methylthio-1-butyl Group for Phosphate/Thiophosphate Protection in Solid-Phase Synthesis of DNA Oligonucleotides, J. Org. Chem., 69: 2509-2515 (2004).*
Cieślak et al. (#2) Thermolytic Properties of a 3-(2-Pyridyl)-1-propyl and 2[N-Methyl N (2-pyridyl)] aminoethyl Phosphate/Thiophosphate Protecting Groups in Solid-Phase Synthesis of Oligodeoxyribunonucleotides, J. Org. Chem., 68: 10123-10129 (2003).*
Jain et al. / Bioorg. Med. Chem. 21 (2013) 6224-6232.*
International Search Report and Written Opinion: International Application No. PCT/US2015/020402; International Filing Date Mar. 13, 2015; dated Jun. 2, 2015; 9 pages.
Jain et al ; "Assessment of the Cellular Internalization of Thermolytic Phosphorothioate DNA Oligonucleotide Prodrugs"; Bioorganic & Medicinal Chemistry; 21; pp. 6224-6232; (2013).

* cited by examiner

*Primary Examiner* — Janet L Epps-Smith
(74) *Attorney, Agent, or Firm* — Klarquist Sparkman, LLP

(57) ABSTRACT

Compounds of the formula $$(Z)_x$$

wherein: each Z is independently selected from 2'-deoxythymidinyl moiety, 2'-deoxyadenosinyl moiety, and a 2'-deoxycytidinyl moiety, x is an integer from 5-20, wherein said 2'-deoxythymidinyl moieties are connected by thiophosphate triester linkages, and 3-12 of said thiophosphate triester linkages being positively charged linkages of the formula:

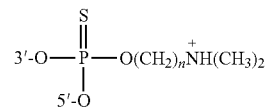

where n is an integer from 2 to 6; and the remainder of the thiophosphate triester linkages are neutral linkages of the formula:

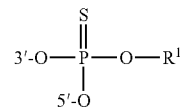

provided that when x is 5-6, the number of positively charged linkages is 3, when x is 7-8, the number of positively charged linkages is 3-4, when x is 9-12, the number of positively charged linkages is 3-10, and when x is 13-20, the number of positively charged linkages is 4-12.

23 Claims, 22 Drawing Sheets
Specification includes a Sequence Listing.

PS-dT₈[3+]

PS-dA$_8$[3+]

PS-dT₁₃[8+]

PS-dT₁₅[10+]

PS-dT$_{17}$[12+]

Figure 23A
Figure 23B
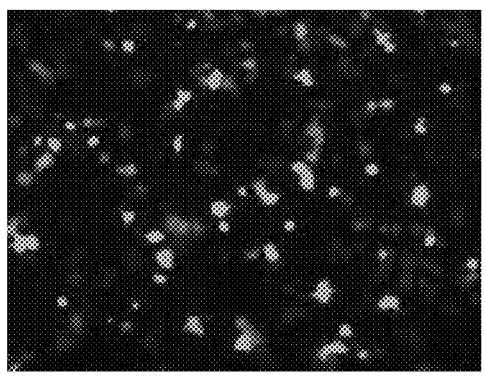
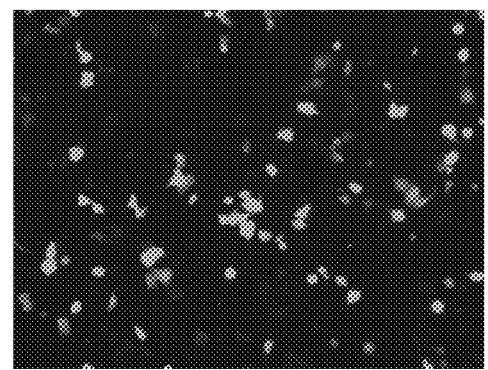

TRANS-ACTING ELEMENTS FOR INTRACELLULAR DELIVERY OF NUCLEIC ACID SEQUENCES

CROSS-REFERENCE TO RELATED APPLICATIONS

This patent application is a continuation-in-part of PCT/US2015/020402, filed on Mar. 13, 2015, which claims priority to U.S. provisional Application Ser. No. 61/952,928, filed on Mar. 14, 2014, the contents of which are incorporated by reference herein in their entirety.

GOVERNMENT RIGHTS

The inventions described herein were developed with support from the Food and Drug Administration. The U.S. government has certain rights in the inventions.

TECHNICAL FIELD

The disclosure is related to trans-acting elements for intracellular delivery of nucleic acids.

BACKGROUND

Oligonucleotide-based drugs show promise as a novel form of chemotherapy. Among the hurdles that have to be overcome on the way of applicable nucleic acid therapeutics, inefficient cellular uptake and subsequent release from endosomes to cytoplasm appear to be the most severe ones. Thus, the ability to deliver nucleic acids (e.g., antisense oligonucleotides and their peptide nucleic acid or phosphorodiamidate morpholino analogues, plasmid DNA, RNA such as mRNA, tRNA and siRNA) to specific cell-type offers opportunities to overcome these shortcomings and the potential to develop novel therapeutics for the treatment of many diseases that are difficult to treat effectively with traditional therapies (e.g., hereditary diseases, cancer).

Watson-Crick base-pairing of nucleic acid sequences with key sequences of mRNA targets has been shown to inhibit the ability of these mRNAs to interact with the cellular machinery required for protein synthesis. For example, the interaction of nucleic acid sequences with the initiation codon or splicing sequences of mRNA targets can alter the transcription of these mRNAs and expression of the encoded proteins. In this context, most human genes undergo alternative splicing events, which are triggered by an intricate and highly regulated machinery requiring the sequence-specific binding of several proteins to nuclear pre-mRNAs. Steric interference imparted by RNase H-incompetent nucleic acid analogues complementary to specific pre-mRNA splice sites has been shown to be efficient in re-directing the splicing machinery during assembly of the mature mRNAs. The biomedical relevance of alternative splicing events has been demonstrated through skipping the mutated exons in dystrophin pre-mRNA as a viable approach to the clinical treatment of Duchenne muscular dystrophy.

Steric interference leading to splice correction requires sequence-specific and high affinity binding of nuclease-resistant RNase-H incompetent oligonucleotide analogues complementary to any targeted intron-exon junctions in the precursor mRNA. Negatively charged 2'-O-methyl RNA phosphorothioate sequences and uncharged peptide nucleic acid (PNA) or phosphorodiamidate morpholino (PMO) oligomers were found adequate for inducing splice correcting events. Currently, cationic lipids are the most popular carriers for in vitro cellular transfection of negatively charged DNA/RNA oligonucleotides and their analogues. However, in addition to being cytotoxic and of poor stability in the presence of serum proteins, these carriers cannot be used for the cellular internalization of uncharged PNAs or PMOs. Remarkably, the conjugation of cationic cell penetrating peptides (CPPs) to PNA or PMO oligomers led to pre-mRNA splicing correction activities in mammalian cells. It should however be noted that the covalent attachment of highly cationic CPPs to PNAs or PMOs may be challenging, as it could produce insoluble conjugates or could inhibit the PNA or PMO portion of the conjugates to perform their intended functions. Although this method was successful at eliciting corrective nuclear pre-mRNA splicing events, this approach to the cellular delivery of PNA oligomers faces technical and cost-effectiveness challenges.

It is well documented that RNA interference (RNAi) has broad potential for silencing any gene. To achieve the clinical potential of RNAi, delivery materials are required to transport short negatively charged double-stranded interfering RNAs (siRNAs) to the site of action in the cells of target tissues. A clinically advanced platform for the cellular delivery of siRNAs is based on the use of dynamic poly-conjugates (DPC). These conjugates incorporate several components, each intended to play a particular role in the delivery process. Typically, siRNAs are attached to a membrane-disrupting polymer by a hydrolysable disulfide linker; the polymer is shielded by polyethylene glycol (PEG), which is designed to be cleaved in an acidic endosomal environment and expose the membrane-disrupting polymer for endosomal release. In the cytosol, the siRNAs are cleaved from the polymer and trigger the RNAi machinery. DPC systems have been shown effective at silencing two different genes when administered intravenously. However, the complexity of DPC systems creates problems in the scale-up of their manufacturing protocols where tightly controlled mixing steps are required to achieve consistent quality of the polyconjugates.

The delivery of DNA and RNA can be used, under gene therapy settings, to tackle various acquired or heritable diseases, where natural immunity is aberrant or lacking. Gene therapy is based on the underlying principle that disease can be addressed by introduction of exogenous genetic material into somatic cells of patients for the purpose of modulating gene expression of desired proteins.

Shortcomings in the delivery of genetic material arise because of the sensitivity of unprotected genetic material to extracellular enzymes. After cellular entry, the genetic material is subjected to intracellular degradation in endosomal/lysosomal compartments. Unassisted genetic material compartmental release is negligible and the small fraction that may escape is exposed to further cytoplasmic degradation and plagued with poor translocation kinetics. When nuclear entry is required for therapeutic activity, crossing the nuclear membranes represents an additional impediment. Regardless of the desired outcome, the use of natural or artificial gene carrier vector systems are required to overcome the above limitations.

The formation of stable cationic lipids-nucleic acid particles that possess the chemical and biophysical properties required to overcome delivery obstructions is essential for an effective gene delivery process. Complexation of genetic material in the formation of lipoplexes proceeds by electrostatic interactions between cationic vectors and anionic nucleic acids. This process results in the compaction of sub-micrometer-sized particles, each composed of numerous DNA (or RNA) molecules. Effective particle formation sterically protects genetic materials from nucleolytic enzymes, enhances cell permeability/uptake, and increases cytosolic mobility. Complexation of genes is most easily controlled by adjusting lipid:gene weight ratios. Optimal ratios correspond to the amount of vector needed to fully complex the genetic material. Although gene delivery is thought to be improved by use of excessive charge, which enable nucleic acids to achieve transient, yet stable interactions, within the nanoparticle, the use of excessive charge can result in undesired toxicity and binding forces that are too strong for efficient gene unpacking. Thus, desired specific structural properties for each vector type must be considered to allow rational design of nanoparticles with the greatest gene delivery potential.

When all is considered, there is indeed a need in the art for structurally simpler, more efficient and cost effective agents for in vitro cellular transfection of neutral and negatively charged nucleic acids (e.g., plasmid DNA, DNA/RNA oligonucleotides including siRNAs, short hairpin RNAs and microRNAs) and their analogues.

SUMMARY

The present disclosure concerns, inter alia, efficient and cost effective agents for in vitro cellular transfection of neutral and charged DNA/RNA oligonucleotides and their analogues, as well as methods for utilizing such agents and kits containing such agents.

In one aspect, included herein is a compound of the formula $(Z)_x$ wherein:
each Z is independently selected from 2'-deoxythymidinyl, 2'-deoxyuridinyl, 2'-deoxyadenosinyl, 2'-deoxycytidinyl, 5-methyl-2'-deoxycytidinyl, 2'-deoxyinosinyl or 7-deaza, 2'-deoxyguanosinyl) moiety, and their corresponding 2'-O-methyl ribonucleosidyl counterparts, in particular 2'-O-methyl uridinyl, x is an integer from 5-20, wherein said 2'-deoxythymidinyl, 2'-deoxyuridinyl, 2'-deoxyadenosinyl, 2'-deoxycytidinyl, 5-methyl-2'-deoxycytidinyl, 2'-deoxyinosinyl or 7-deaza-2'-deoxyguanosinyl) moieties and their corresponding 2'-O-methyl ribonucleosidyl counterparts are connected by thiophosphate triester linkages, 3-12 of said thiophosphate triester linkages being positively charged linkages of the formula:

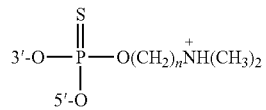

wherein n is an integer from 2 to 6;
the remainder of said thiophosphate triester linkages, where applicable, are neutral linkages of the formula:

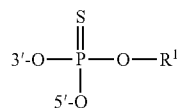

wherein each $R^1$ is, independently, an alkyl, cycloalkyl, alkenyl, cycloalkenyl, alkynyl, alkyl ether, cycloalkyl ether alkyl thioether, cycloalkyl thioether, alkylpolyether, a nitrogen-containing or a nitrogen and oxygen-containing heterocyclic alkylyl group containing 6-28 carbons or cholesteryl;

provided that when x is 5-6, the number of positively charged linkages is 3, when x is 7-8, the number of positively charged linkages is 3-4, when x is 9-12, the number of positively charged linkages is 3-10, and when x is 13 to 20, the number of positively charged linkages is 4-12.

In certain embodiments, the ratio of neutral linkages to positively charged linkages is from 0.3 to 1.5.

In some embodiments, $(Z)_x$ is $(dT)_x$, $(dU)_x$, $(dA)_x$, $(dI)_x$, $(dC)_x$, $d(^{5-Me}C)_x$, $d(^{7-deaza}G)_x$, (2'-O-methyl U)$_x$, (2'-O-methyl A)$_x$, (2'-O-methyl C)$_x$, (2'-O-methyl $^{5-Me}$C)$_x$, (2'-O-methyl $^{5-Me}$U)$_x$ or (2'-O-methyl $^{7-deaza}$G)$_x$.

In some embodiments, $(Z)_x$ is $(dT)_x$, $(dA)_x$, or $(dC)_x$, or (2'-O-methyl U)$_x$.

In certain compounds, $R^1$ is $C_4$-$C_{10}$ alkyl. In some embodiments, n is an integer 2 to 4. Certain preferred embodiments have $R^1$ as 1-octyl and n is 4.

Preferred compounds include those designated PS-dT$_8$[3+], PS-dA$_8$[3+], PS-dC$_8$[3+], PS-dT$_{11}$[6+], PS-dT$_{13}$[8+], PS-dT$_{15}$[10+] and PS-dT$_{17}$[12+] schematically presented below.

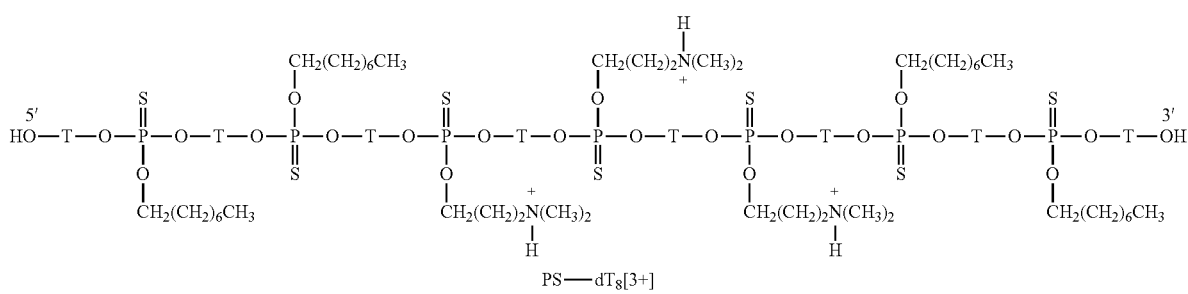

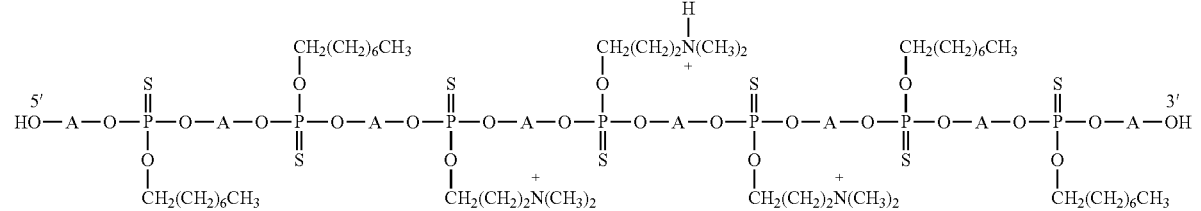
PS—dA₈[3+]
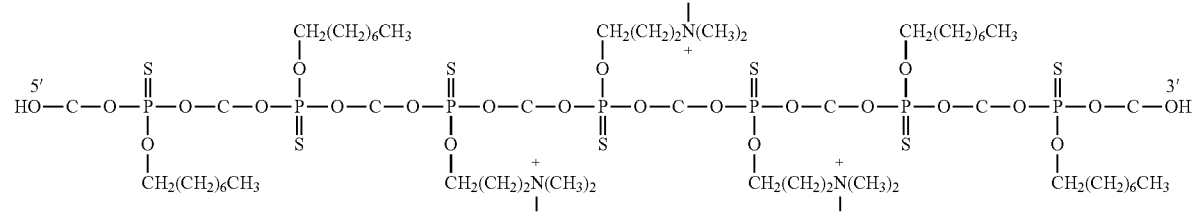
PS—dC₈[3+]
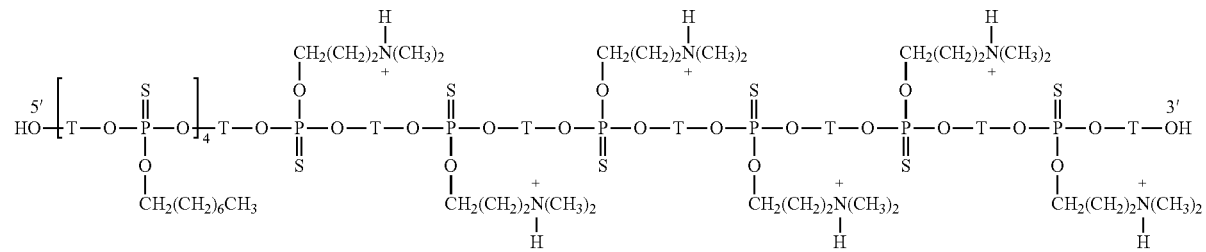
PS—dT₁₁[6+]
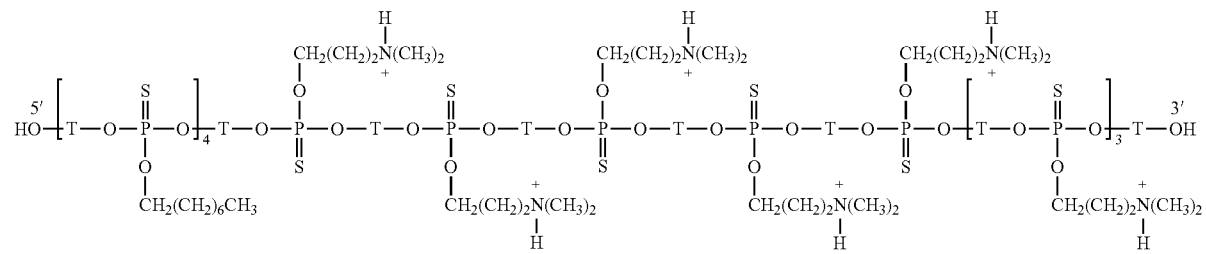
PS—dT₁₃[8+]
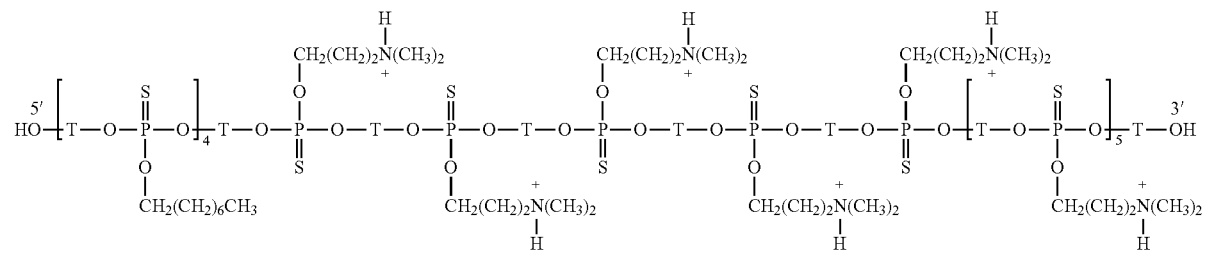
PS—dT₁₅[10+]
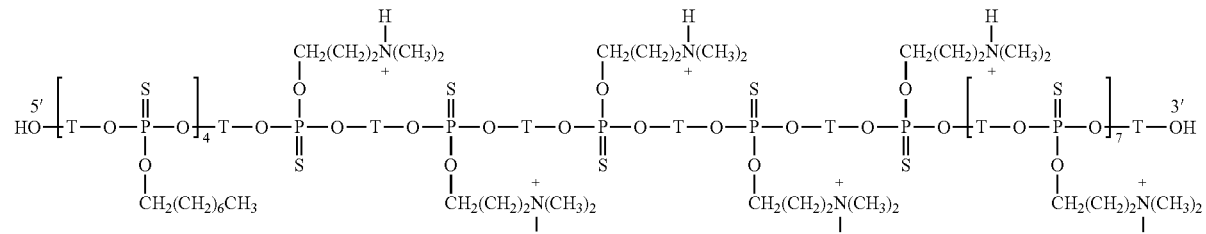
PS—dT₁₇[12+]

Abbreviations: T, 2'-deoxythymidinyl; A, 2'-deoxyadenosinyl; C, 2'-deoxycytidinyl An additional preferred compound is PS-2'-OMeU$_8$[3+] as shown in FIG. 28.

In another aspect, the invention concerns methods of introducing a nucleic acid into a cell by utilizing a compound described herein as a transfection agent. In some embodiments, the method comprises (i) contacting said nucleic acid with a transfection agent described herein to form a complex; and (ii) contacting the complex with said cell. The nucleic acid can be charged or uncharged. Some preferred nucleic acids have a negative charge. Preferred nucleic acids include is peptide nucleic acids (PNA) and morpholino phosphorodiamidate (PMO), phosphorothioate DNA sequences, DNA plasmids and siRNA sequences.

In some embodiments, the methods have a threshold percentage delivery of nucleic acid to a target cell is at least 20%.

In other embodiments, the compound is delivered to the cell in a medium and said compound did not induce cytotoxicity of more than 15% higher than that of the medium in the absence of said compound.

In yet another aspect, the invention concerns a kit comprising a transfection agent described herein and a nucleic acid.

In a further aspect, the invention concerns phosphoramidite monomers disclosed herein (including those in FIG. 9) and oligomers of such monomers.

BRIEF DESCRIPTION OF THE DRAWINGS

FIG. 23 shows delivery of plasmid in HeLa pLuc cells in the absence of serum (A) and in the presence of 10% FBS (B) using PS-dT$_{11}$[6+] (4 μM) as the transfection reagent.

DETAILED DESCRIPTION

Figure 1:
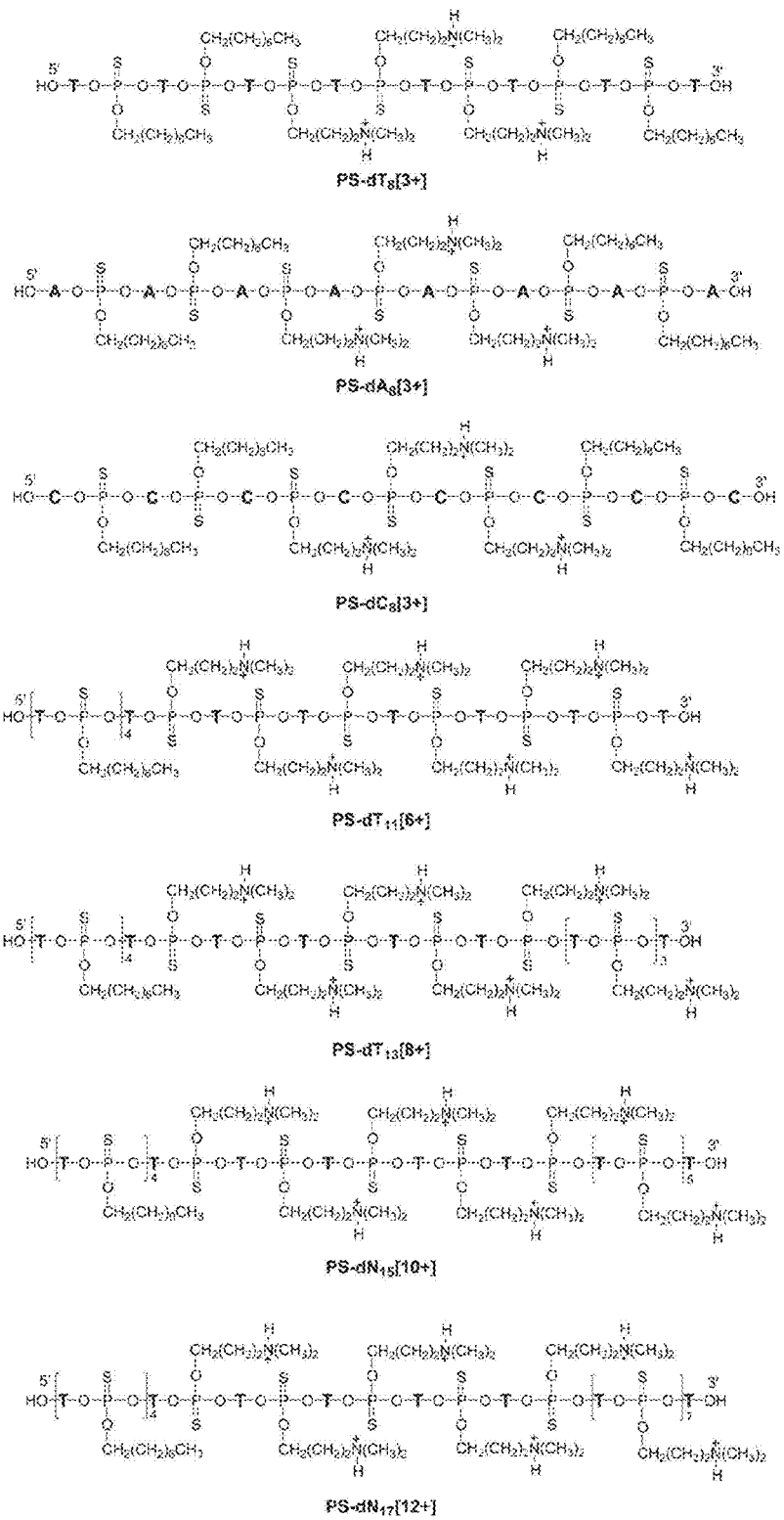
FIG. 1 presents schematic representations of the compounds designated PS-dT$_8$[3+], PS-dA$_8$[3+], PS-dC$_8$[3+], PS-dT$_{11}$[6+], PS-dT$_{13}$[8+], PS-dT$_{15}$[10+] and PS-dT$_{17}$[12+].

The present disclosure concerns, inter alia, use of trans-acting phosphorothioate DNA elements (PS-dT$_8$[3+], PS-dC$_8$[3+], PS-dA$_8$[3+], PS-dT$_{11}$[6+], PS-dT$_{13}$[8+], PS-dT$_{15}$[10+], PS-dT$_{17}$[12+], PS-2'-OMeU$_8$[3+], and mixed constructs) for the transfection of charged and uncharged species such as PNA, PMO, RNA, DNA oligomers. Novel amphipathic trans-acting phosphorothioate DNA elements (PS-dT$_8$[3+], PS-dC$_8$[3+] and PS-dA$_8$[3+]) have been developed for the transfection of uncharged PNA and PMO oligomers targeting the defective luciferase gene in the well-studied HeLa pLuc705 cell line. The structural design of PS-dT$_8$[3+], PS-dC$_8$[3+] and PS-dA$_8$[3+] is based on earlier observations of the increased cellular uptake of an uncharged thermosensitive DNA oligonucleotide prodrug in Vero cells upon replacement of four neutral thiophosphate triester functions with four positively charged ones. Hydrophobic groups were incorporated into the DNA elements to impart amphiphilicity, which is known to facilitate in vitro cellular delivery of nucleic acids. The objectives were to: (i) demonstrate the efficiency of PS-dT$_8$[3+]-, PS-dC$_8$[3+]- or PS-dA$_8$[3+]-mediated internalization of appropriately designed PNA and PMO oligomers in various cell lines, and (ii) confirm the functionality of these oligomers through alternate splicing of the pre-mRNA luciferase gene in the HeLa pLuc705 cell line. The schematic representation of a DNA element is shown below. "ONO" represents 2'-deoxythymidynyl-, 2'-deoxycytidinyl- or 2'-deoxyadenosinyl- or 2'-O-methyluridinyl-.

difficulty in the manufacturing of these cationic lipids by automated techniques, unlike the instant positively charged DNA-based tranfection elements. Furthermore, the transfection efficiency of cationic lipids is outweighed by their cytotoxicity and in many cases by the presence of serum-containing media. Importantly, cationic lipid cannot deliver in trans uncharged PNA or morpholino oligomers in mammalian cells even if the uncharged oligomers are polyA-tailed. Our DNA-based transfection elements can deliver efficiently uncharged polyA-tailed PNA and PMO oligomers in mammalian cells with minimal cytotoxicity in serum-free or serum containing media. The inventors have observed that a cationic guanidinium-based transfection reagent conjugated to a PMO oligomer is be 10-times less efficient than our DNA-based transfection elements for the delivery of the polyA-tailed PMO sequence in HeLa cells.

Lipofectamine® is the state of the art lipid transfection reagent and is commercially available at a high cost. The instantly described DNA-based transfection elements are economically prepared using standard laboratory techniques. Lipofectamine® functions well as a transfection agent for certain compounds but mainly in serum free media. The DNA-based transfection agents described herein work well in both serum-free and serum-containing media. In addition, the cytotoxicity of Lipofectamine® is by far greater than our DNA-based transfection elements.

In regard to known cell-penetrating peptides (CPPs), these peptides require conjugation to the oligomers (uncharged PNAs/PMOs or negatively charged nucleic acids) for transfection; CPPs do not work in trans like the DNA-based transfection elements described herein. The conjugation of CPPs to oligomers is a very tedious and relatively inefficient process. Although CPPs have been found effective as transfecting reagents, they were shown, upon conjugation, to negatively affect the aqueous solubility of the oligomers and prevent them to perform their intended functions. A major limitation of CPPs is that one CPP must be conjugated to each uncharged or negatively charged oligomer sequence for delivery into mammalian cells. Para-

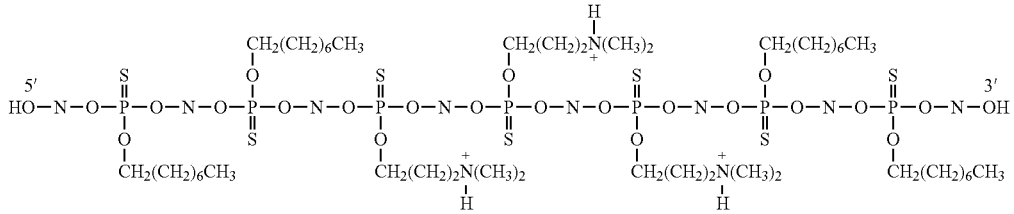

The instant oligomers provide novel structures and utility over oligomers known in the art. Rather than DNA based oligomers like those of the instant disclosure, commercial transfection products focus on the use of cationic lipids or naturally positively charged peptides. The state of the art product is Lipofectamine®, a cationic lipid. To date, DNA based oligomers have not been able to be used as transfection agents. The compounds of the instant invention are effective transfection agents and are advantageous over current state of the art products.

The two major classes of transfection reagents are cationic lipids (Lipofectamine®, DOTAP, DOTMA, DOSPA, DC-Chol and the like) and cell-penetrating peptides. Many cationic lipids are commercially available but suffer from low transfection efficiencies and cytotoxicities. There is also doxically, one DNA-based transfection element can deliver efficiently any uncharged polyA-tailed PNA and PMO oligomer sequence or negatively charged nucleic acid into mammalian cells. One must therefore conclude that much like the cationic lipids, the transfection efficiency of CPPs is outweighed by inherent shortcomings including conjugation and lack of aqueous solubility and functionality of the CPP-conjugates.

In short, the oligomers of the instant disclosure are cheaper and more flexible in use (both serum conditions and charge of the element to be transported) than the state of the art products.

Figure 9:
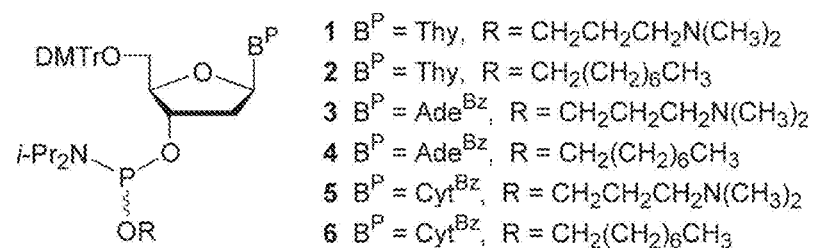
FIG. 9 presents schematic representations of the deoxyribonucleoside phosphoramidites used in the solid-phase synthesis PS-dT$_8$[3+], PS-dA$_8$[3+], PS-dC$_8$[3+], PS-dT$_{11}$[6+], PS-dT$_{13}$[8+], PS-dT$_{15}$[10+] and PS-dT$_{17}$[12+]. Abbreviations: DMTr, 4,4'-dimethoxytrityl; Thy, thymin-1-yl; Ade$^{Bz}$, N$^6$-benzoyladenin-9-yl, Cyt$^{Bz}$, N$^4$-benzoylcytosin-1-yl.
Figure 10:
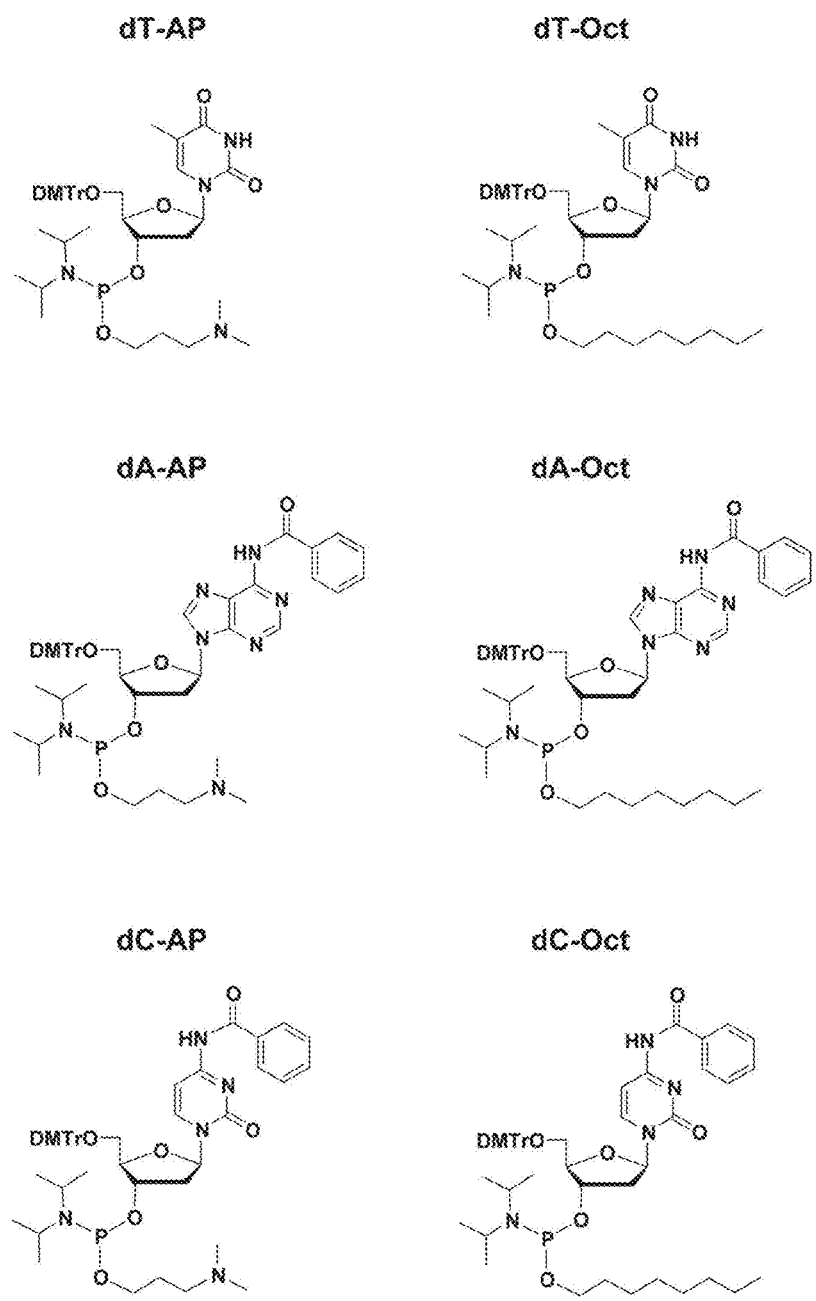
FIG. 10 presents the chemical structures of the deoxyribonucleoside phosphoramidites used in the solid-phase synthesis PS-dT$_8$[3+], PS-dA$_8$[3+], PS-dC$_8$[3+], PS-dT$_{11}$[6+], PS-dT$_{13}$[8+], PS-dT$_{15}$[10+] and PS-dT$_{17}$[12+]. Abbreviation: DMTr, 4,4'-dimethoxytrityl.

The chemical synthesis of PS-dT$_8$[3+], PS-dC$_8$[3+] and PS-dA$_8$[3+] or mixed compositions is easily performed using standard solid-phase techniques and appropriate deoxyribonucleoside phosphoramidites (FIG. 9, below). The detailed preparation of these phosphoramidites is described herein.

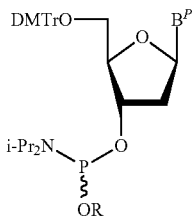

| | |
|---|---|
| $B^P$=Thy, R=$CH_2CH_2CH_2N(CH_3)_2$ | 1 |
| $B^P$=Thy, R=$CH_2(CH_2)_6CH_3$ | 2 |
| $B^P$=Ade$^{Bz}$, R=$CH_2CH_2CH_2N(CH_3)_2$ | 3 |
| $B^P$=Ade$^{Bz}$, R=$CH_2(CH_2)_6CH_3$ | 4 |
| $B^P$=Cyt$^{Bz}$, R=$CH_2CH_2CH_2N(CH_3)_2$ | 5 |
| $B^P$=Cyt$^{Bz}$, R=$CH_2(CH_2)_6CH_3$ | 6 |

Fluoresceinated and unlabeled PNA and PMO oligomers along with appropriate control sequences were obtained from commercial sources (PNA Bio, Inc. and Gene Tools LLC). These sequences are listed in Table 1.

The PS-dT$_8$[3+]-mediated cellular internalization of 5′-fluoresceinated PNA oligomers in HEK 293, HeLa, HeLa pLuc705, MCF7 and SK—N—SH live cells was evaluated by flow cytometry. The results of the FACS analyses are presented in FIG. 11, which shows that the polyA-tailed PNA oligomers 7 and 8 are efficiently internalized in the presence of PS-dT$_8$[3+] in all the cell lines under study. In contrast, the PNA oligomer 9 lacking the polyA stretch is not significantly internalized under similar conditions. Without being held to theory, it was hypothesized that the affinity of PS-dT$_8$[3+] for the polyA tail of the PNA oligomers, is responsible for their cellular uptake.

Figure 12:
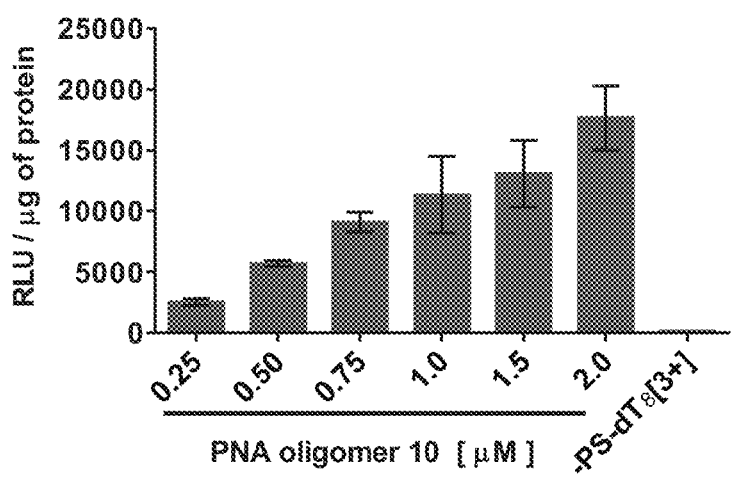
FIG. 12 shows concentration-dependence of splice correction activity upon PS-dT$_8$[3+]-mediated delivery of the PNA oligomer 10 in HeLa pLuc 705 cells. The concentration of PS-dT$_8$[3+] is 2 μM. Abbreviation: RLU, relative light unit.
Figure 13:
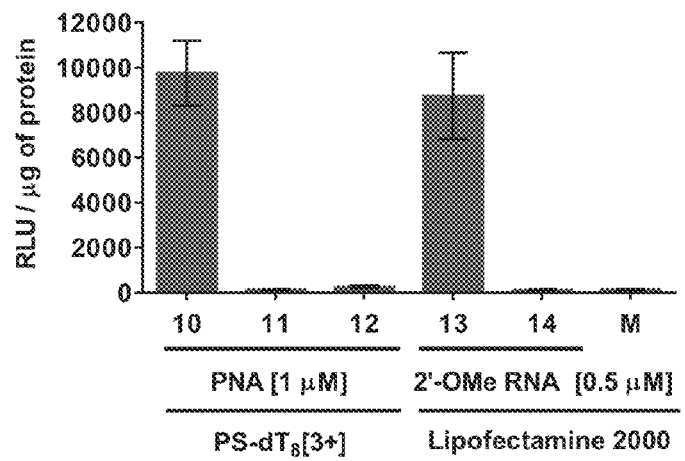
FIG. 13 shows comparative splice correction activity between the PS-dT$_8$[3+]-assisted delivery of PNA oligomers 10, 11, 12 and the Lipofectamine™ 2000-mediated delivery of the 2'-OMe RNA sequences 13 and 14 at the indicated concentrations while the concentration of PS-dT$_8$[3+] and Lipofectamine 2000 was kept at 2 μM and 2 μL/mL, respectively in all experiments. Abbreviations: RLU, relative light unit; M, medium.

The efficiency of PS-dT$_8$[3+] in the cellular uptake of polyA-tailed PNA oligomers was assessed through the luciferase splice correction assay in which the mutated intron 2 of the human β-globin gene has been inserted within the coding sequence of a luciferase reporter gene (pLuc705). The activation of a cryptic splice site in this intron leads to a defective luciferase enzyme. In the presence of a PNA oligomer complementary to the aberrant splice site, correct splicing is restored and results in an active luciferase. A concentration-dependence of splice correction activity by PS-dT$_8$[3+]-mediated internalization of the PNA oligomer 10 in HeLa pLuc705 cells is shown in FIG. 12. FIG. 13 shows a comparative splice correction activity between the PS-dT$_8$[3+]-assisted deliveries of PNA oligomers (11 and 12) and 2′-OMe RNA sequences (13 and 14).

Clearly demonstrated in FIG. 12 is the efficiency with which the polyA-tailed PNA oligomer 10 is internalized into

TABLE 1

Sequence of commercial PNA and PMO oligomers

| Oligomer Number | SEQ ID NO. | Type | Sequence[a] |
|---|---|---|---|
| 7 | 1 | PNA | F1-CCTCTTACCTCAGTTACA-AAAAAA-NH$_2$ |
| 8 | 2 | PNA | F1-GTGGCCGTTTACGTCGCC-AAAAAA-NH$_2$ |
| 9 | 3 | PNA | F1-CCTCTTACCTCAGTTACA-NH$_2$ |
| 10 | 4 | PNA | H-CCTCTTACCTCAGTTACA-AAAAAA-NH$_2$ |
| 11 | 5 | PNA | H-GTGGCCGTTTACGTCGCC-AAAAAA-NH$_2$ |
| 12 | 6 | PNA | H-CCTCTTACCTCAGTTACA-NH$_2$ |
| 13 | 7 | 2′-OMe RNA | 5′-C•C•U•C•U•U•A•C•C•U•C•A•G•U•U•A•C•A |
| 14 | 8 | 2′-OMe RNA | 5′-G•U•G•G•C•C•G•U•U•U•A•C•G•U•C•G•C•C |
| 15 | 9 | PNA | H-CCTCTTACCTCAGTTACA-TTTTTT-NH$_2$ |
| 16 | 10 | PNA | H-CCTCTTACCTCAGTTACA-CCCCCC-NH$_2$ |
| 17 | 11 | PNA | H-AAAAAA-CCTCTTACCTCAGTTACA-NH$_2$ |
| 18 | 12 | PMO | CCTCTTACCTCAGTTACA-AAAAAA-F1 |
| 19 | 13 | PMO | GTGGCCGTTTACGTCGCC-AAAAAA-F1 |
| 20 | 14 | PMO | CCTCTTACCTCAGTTACA-F1 |
| 21 | 15 | PMO | CCTCTTACCTCAGTTACA-AAAAAA |
| 22 | 16 | PMO | GTGGCCGTTTACGTCGCC-AAAAAA |
| 23 | 17 | PMO | CCTCTTACCTCAGTTACA |
| 24 | 18 | PMO | CCTCTTACCTCAGTTACA-AATAAA |

[a]F1, fluorescein; phosphorothioate diester

HeLa pLuc705 cells when using the trans-acting DNA element PS-dT$_8$[3+] as a carrier.

Figure 11:
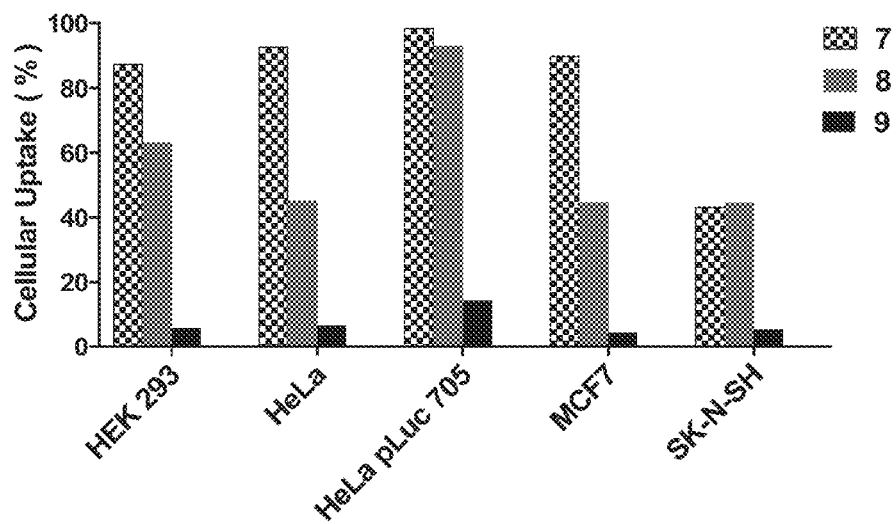
FIG. 11 illustrates internalization of the PS-dT$_8$[3+]:PNA oligomer complexes in live cells. The concentration of PNA oligomer 7, 8, or 9 is 1 M.

This experiment also indicated that 10 escaped endosomal entrapment and induced splice correction of the pre-mRNA encoding luciferase in the nucleus of the cells. In the absence of PS-dT$_8$[3+] in this experiment no luciferase activity was detected. As shown in FIG. 13, the negative control polyA-tailed PNA oligomer 11 failed, as expected, to restore luciferase activity even though PS-dT$_8$[3+] was competently carrying the corresponding fluoresceinated PNA oligomer conjugates 7 and 8 into HeLa pLuc705 cells (FIG. 11). The PNA oligomer 12, which is 10 lacking the polyA stretch, did not restore luciferase activity, because PS-dT$_8$[3+] failed to efficiently internalize its fluoresceinated conjugate 9 into HeLa pLuc705 cells (FIG. 11). For comparability purposes, the negatively charged positive control 2'-OMe RNA sequences 13, which was transfected into HeLa pLuc705 cells using Lipofectamine™ 2000 as the carrier, showed comparable luciferase activity as that produced by the PS-dT$_8$[3+]-assisted transfection of the polyA-tailed PNA oligomer 10 at a two-fold higher concentration. No luciferase activity was generated when the negative control 2'-OMe RNA sequences 14 was transfected under identical conditions (FIG. 13). The uniqueness of PS-dT$_8$[3+] for cellular internalization of neutral PNA oligomers is convincingly demonstrated when compared to the use of preformed PNA/DNA heteroduplexes that is required for efficient Lipofectamine™ 2000-assisted delivery of PNA oligomers into live mammalian cells.

Figure 14:
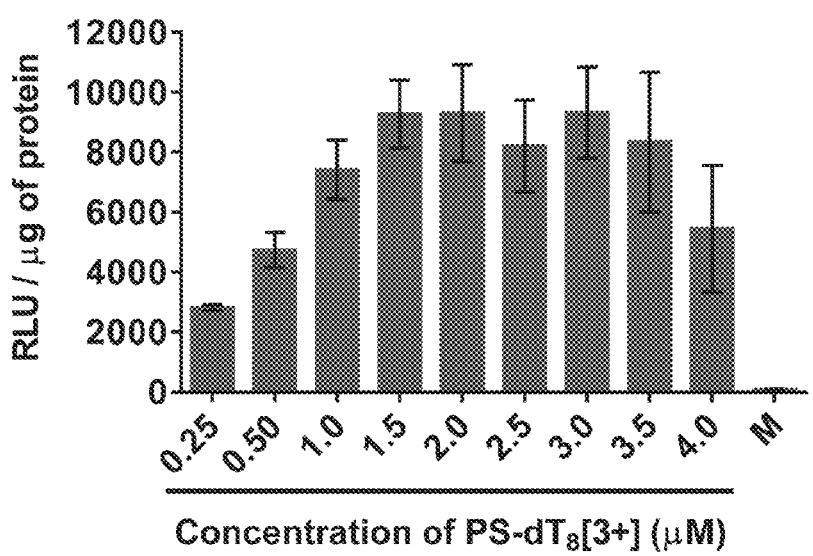
FIG. 14 illustrates the relevance of the concentration of PS-dT$_8$ [3+] to the production of luminescence upon transfection of the polyA-tailed PNA oligomer 10 into HeLa pLuc705 cells. The concentration of the PNA oligomer 10 is 1 μM. Abbreviations: RLU, relative light unit; M, medium.

The relationship between the concentration of PS-dT$_8$[3+] and the extent of luminescence production upon transfection of the polyA-tailed PNA oligomer 10 into HeLa pLuc705 cells was then investigated (FIG. 14). Luciferase activity was found to be optimal at a PS-dT$_8$[3+] concentration in the range of 2-3 µM. When the concentration of PS-dT$_8$[3+] exceeded 3 µM, luciferase activity began to decrease due to increased PS-dT$_8$[3+] cytotoxicity. The spatial arrangement and the criticality of polyA stretch of the PNA oligomer 10 in terms of requirements for recognition by PS-dT$_8$[3+] and cellular internalization were evaluated. This was achieved by moving the polyA stretch from the N-terminus of 8 to its C-terminus or replacing the polyA stretch with a polyT or a polyC stretch at the N-terminus. The consequences of these structural changes were monitored by measuring luciferase activity upon PS-dT$_8$[3+]-mediated transfection of these modified PNA oligomers (15-17) into HeLa pLuc705 cells.

Figure 15:
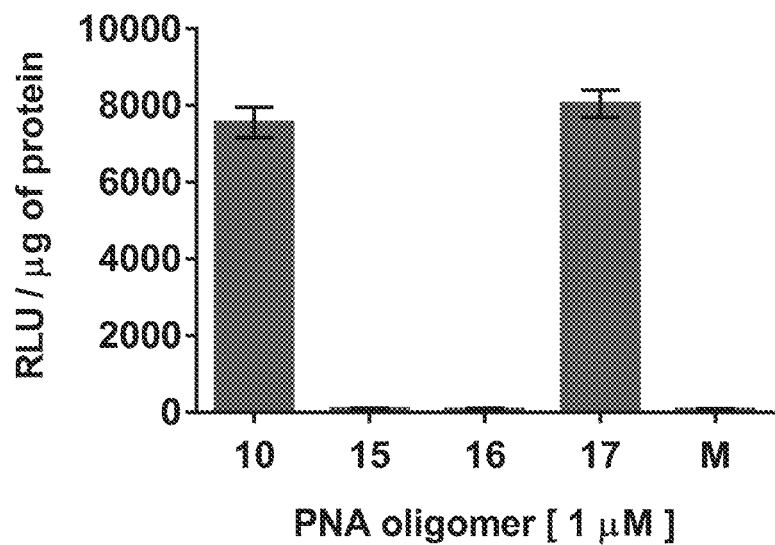
FIG. 15 shows the relevance of the spatial arrangement and recognition of the polyA-stretch for efficient PS-dT$_8$ [3+]-assisted uptake of PNA oligomers 10, 15-17 in HeLa pLuc705 cells. The concentration of PS-dT$_8$[3+] is 2 μM. Abbreviations: RLU, relative light unit; M, medium.

FIG. 15 shows that moving the polyA stretch from the N-terminus of 10 to its C-terminus did not significantly affect the PS-dT$_8$[3+]-assisted transfection efficiency of PNA oligomer 17 under similar conditions. However, replacing the polyA stretch of 10 with a polyT or a polyC stretch at the N-terminus did not lead to the production of luciferase activity due to poor PS-dT$_8$[3+]-mediated cellular internalization of PNA oligomers 15 and 16 in HeLa pLuc705 cells. These findings suggest that recognition of the polyA stretch of PNA oligomer 10 by PS-dT$_8$[3+] is necessary for efficient cellular uptake of the oligomer.

Figure 16:
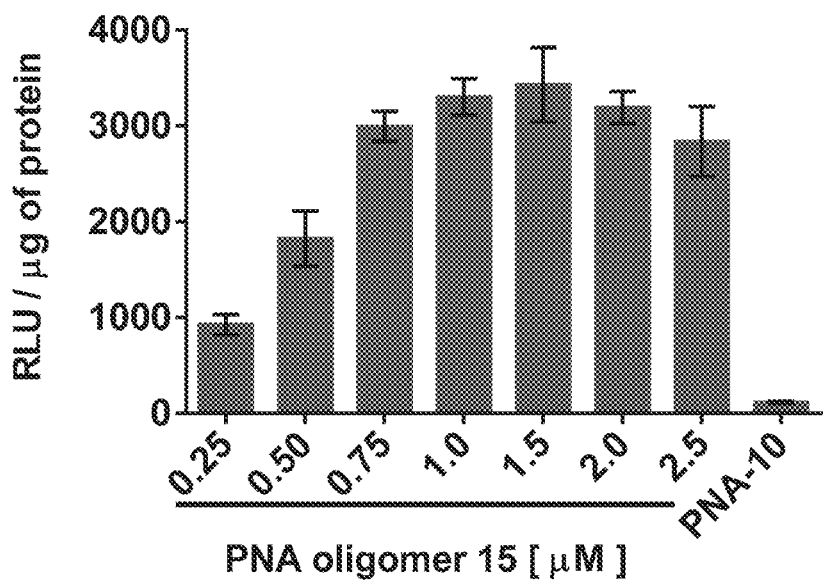
FIG. 16 shows concentration-dependence of splice correction activity upon PS-dAs[3+]-mediated delivery of the PNA oligomer 15. The concentration of the PNA oligomer 10 and PS-dA$_8$[3+] is 1 M and 2.0 μM, respectively. Abbreviation: RLU, relative light unit.

However, when the PNA oligomer 15 is transfected into HeLa pLuc705 cells using the PS-dA$_8$[3+] DNA element, luciferase activity is restored to a level that is dependent of the concentration of 15, to reach half the level of luciferase activity obtained with the PS-dT$_8$[3+]:10 complex under similar conditions (FIG. 16). This relatively lower luciferase activity may tentatively result from interfering tail complementarity of polyadenylated cellular mRNAs with the polyT-tailed PNA oligomer 15. Such interference can potentially lead to a significantly decreased nuclear concentration of 15, when compared to that of 10, for pre-mRNA splicing correction under similar conditions.

Poor luciferase activity was detected when PS-dA$_8$[3+] was used as the carrier for the PNA oligomer 10 under near identical conditions (FIG. 16). These results are consistent with the recognition of the polyT stretch of PNA oligomer 15 by PS-dA$_8$[3+] as a critical requirement for efficient cellular uptake of the oligomer when considering that PS-dA$_8$[3+] failed to internalize 16, 17 (data not shown) into HeLa pLuc705 cells.

Figure 17:
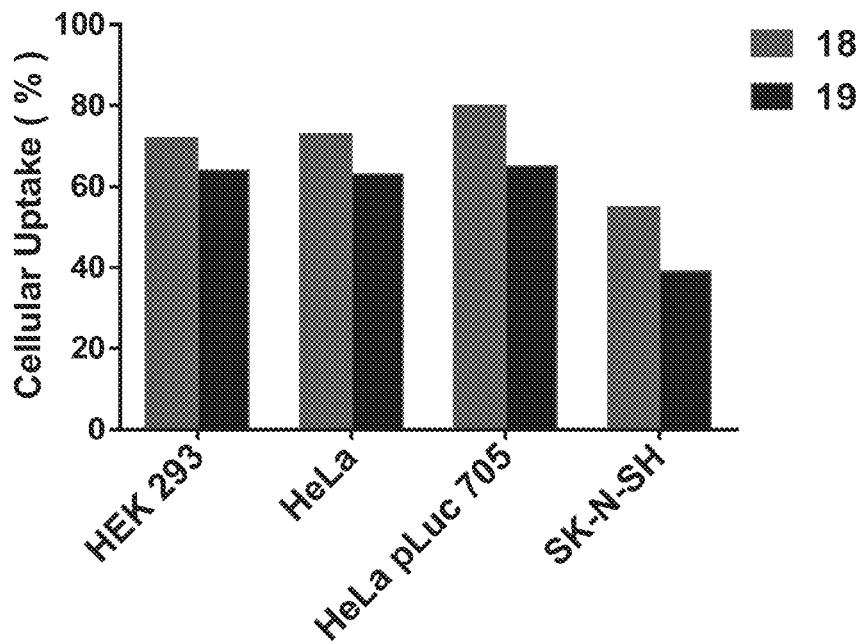
FIG. 17 shows internalization of the PS-dT$_8$[3+]:PMO oligomer complexes in live cells. The concentration of PMO oligomer 18 or 19 is 1 μM. The concentration of PS-dT$_8$[3+] is 2 μM. Abbreviation: M, medium.

The PS-dT$_8$[3+]-mediated delivery of the fluoresceinated PMO oligomers 18, 19 and 20 into the same cell lines, as those used for the internalization of PNA oligomers, was monitored by flow cytometry under similar experimental conditions. As shown in FIG. 17, the results of the FACS analyses confirmed the delivery of the polyA-tailed PMO oligomers 18 and 19 by PS-dT$_8$[3+] in all cell lines. However, the PS-dT$_8$[3+]-mediated internalization of the PMO oligomer 20, lacking the polyA stretch, was reduced to that of the medium in any of the cell lines tested.

Figure 18:
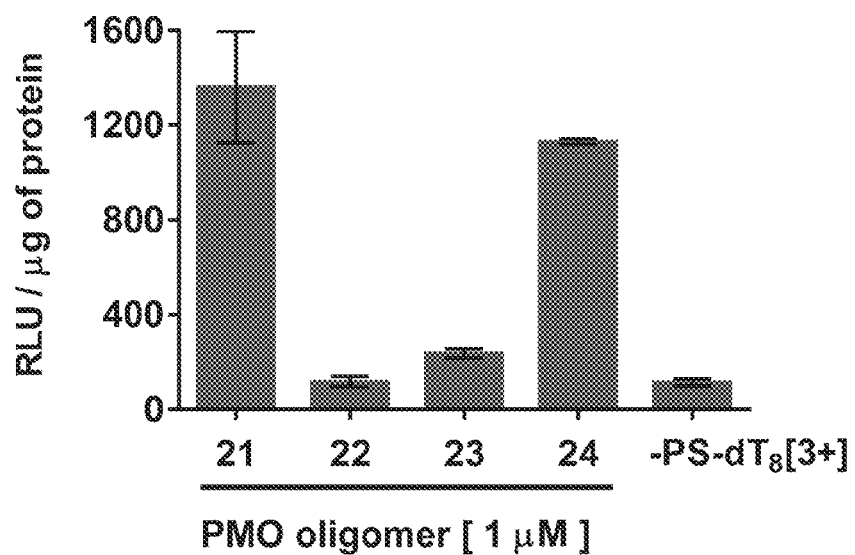
FIG. 18 shows the relevance of the recognition of the polyA-stretch for efficient PS-dT$_8$[3+]-assisted internalization of PMO oligomers 21-24 (1 μM) in HeLa pLuc705 cells. The concentration of PS-dT$_8$[3+] is 2 μM. Abbreviation: RLU, relative light unit.

Consistent with the PNA oligomer study, the PS-dT$_8$[3+]-assisted internalization of PMO oligomer 21 into HeLa pLuc705 cells led to the production luciferase activity production at a level that is about 5-fold less than that obtained with PNA oligomers at similar oligomer concentrations. (FIG. 18) On the basis of evidence indicating that PMO oligomers exhibited a 4-fold higher binding affinity for complementary bacterial RNA than PNA oligomers, these results indicate that PS-dT$_8$[3+] is less competent at internalizing PMO oligomers than PNA oligomers into HeLa pLuc 705 cells. Noteworthy is the replacement of one 2'-deoxyadenosine residue with 2'-deoxythymidine in the polyA tail of PMO oligomer 21, which did not significantly affect the ability of PS-dT$_8$[3+] to internalize oligomer 24 into HeLa pLuc705 cells on the basis of luciferase activity production (FIG. 18). Thus one A→T modification in the polyA tail of 24 is not sufficient to prevent its recognition and cellular internalization by PS-dT$_8$[3+], which would have resulted in a significant lack of splice correction activity. As expected, in the absence of PS-dT$_8$[3+], the internalization of oligomer 21 into HeLa pLuc705 cells is reduced to that of the negative control oligomer 22 or that of the positive control oligomer 23 lacking the polyA tail (FIG. 18).

Figure 19:
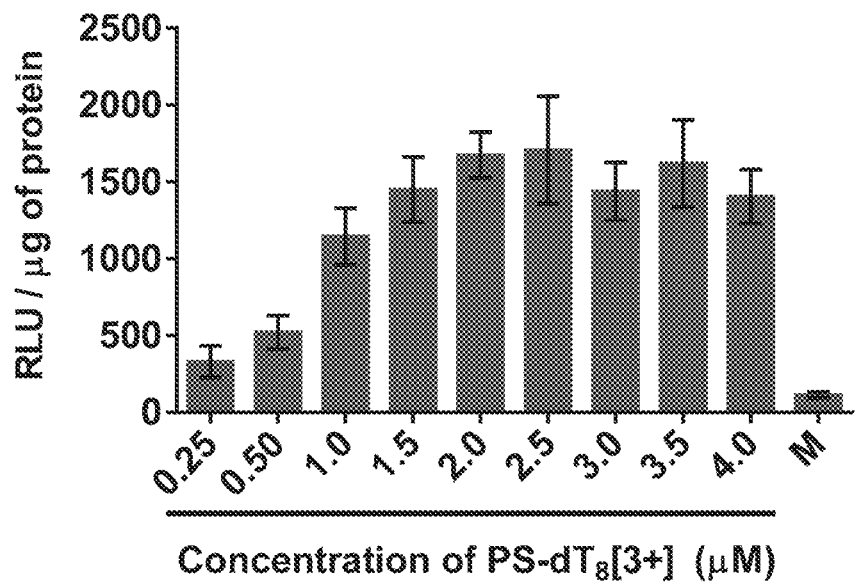
FIG. 19 shows the relevance of the concentration of PS-dT$_8$[3+] to the production of luminescence upon transfection of the polyA-tailed PMO oligomer 21 (1 μM) into HeLa pLuc705 cells. Abbreviation: RLU, relative light unit; M, medium.
Figure 20:
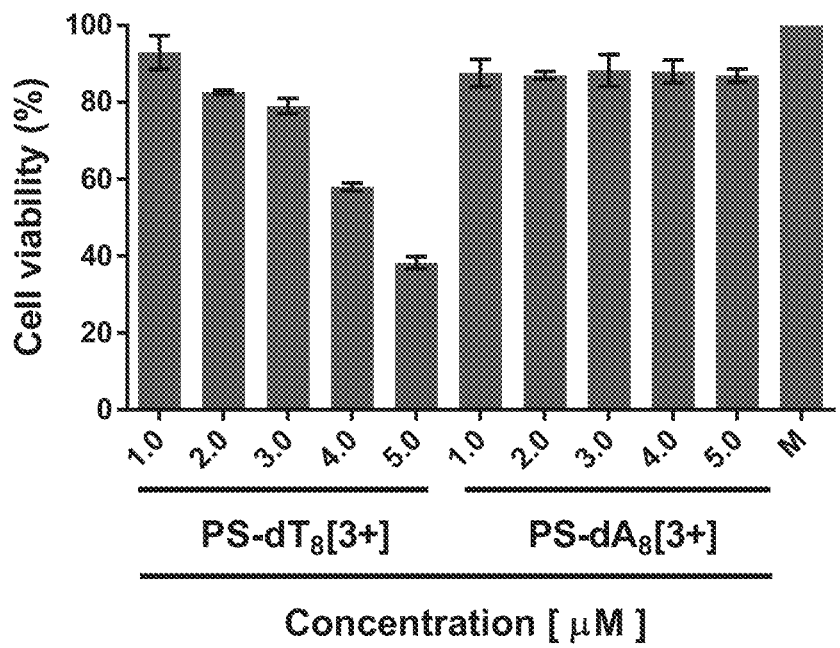
FIG. 20 shows the concentration dependence of the cytotoxicity of PS-dT$_8$[3+] and PS-dA$_8$[3+] in HeLa pLuc705 cells. Abbreviation: M, medium.

The effect of PS-dT$_8$[3+] concentration on the cellular uptake of PMO oligomer 21 into HeLa pLuc705 cells was also investigated. Similar to the study performed with the PNA oligomer 10, the PS-dT$_8$[3+]-mediated delivery of the PMO oligomer 21 into HeLa PLuc 705 cells was found optimal, in terms of luciferase activity production, when the concentration of PS-dT$_8$[3+] was in the range of 2-3 µM. At a PS-dT$_8$[3+] concentration exceeding 3.5 µM, the production of luciferase activity decreased, presumably because of increased PS-dT$_8$[3+] cytotoxicity at such concentrations (FIG. 19). Indeed, when the concentration of PS-dT$_8$[3+] alone in HeLa pLuc 705 cells reaches 5.0 M, only 40% of the cells are viable. In contrast, the cytotoxicity of PS-dA$_8$[3+] is significantly lower than that of PS-dT$_8$[3+] given that 90% of the cells remain viable under identical conditions (FIG. 20).

Definitions: The term "alkyl" is used herein refers to both straight- and branched-chain saturated aliphatic hydrocarbon groups having at least one carbon atoms, e.g., 1 to 12, 1 to 8 or 1 to 6 carbon atoms. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, n-heptyl, n-octyl, and the like.

The term "cycloalkyl", employed alone or in combination with other terms, is defined herein as, unless otherwise stated, a monocyclic, bicyclic, tricyclic, fused, bridged, or spiro monovalent saturated hydrocarbon moiety of 3-10 carbon atoms, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like.

"Alkenyl" is intended to include both straight- and branched-chain alkyl group with at least one carbon-carbon double bond, e.g., having 2-12, 2-8 or 2-6 carbon atoms. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, and the like.

The term "cycloalkenyl", employed alone or in combination with other terms, is defined herein as, unless otherwise stated, a monocyclic, bicyclic, tricyclic, fused, bridged, or spiro monovalent unsaturated hydrocarbon moiety of 3-10 carbon atoms containing at least one double bond, wherein the carbon atoms are located inside or outside of the ring system. Any suitable ring position of the cycloalkenyl moiety may be covalently linked to the defined chemical structure. Examples of cycloalkenyl moieties include, but are not limited to, chemical groups such as cyclopropenyl, cyclopropenylmethyl cyclobutenyl, cyclopentenyl, cyclohexenyl, cyclohexenylmethyl, cyclohexenylethyl, cycloheptenyl, norbornenyl, and homologs, isomers, and the like.

"Alkynyl" is intended to cover both straight- and branched-chain alkyl group with at least one carbon-carbon triple bond, e.g., having 2-12, 2-8 or 2-6 carbon atoms.

As used herein, the terms "alkyl ether" and "alkyl thioether" are intended to include alkyl chains, either in a straight or branched configuration, with an oxygen or sulfur atom respectively having two points of attachment (i.e., is a diradical) in the chain.

The terms "cycloalkyl ether" and "cycloalkyl thioether" refer to cycloalkyl groups having at least one oxygen or sulfur atom, respectively, in the cycloalkyl ring.

The term "alkylpolyether" refers to an alkyl group containing a polyether group either within the alkyl chain or at the terminus of the alkyl group.

The term "cholesteryl," as used herein, refers to steroidal hydrocarbon moieties derived from, or structurally similar to cholesterol.

"dT" refers to a 2'-deoxythymidinyl moiety.

"dA" refers to a 2'-deoxyadenosinyl moiety.

"dC" refers to a 2'-deoxycytidinyl moiety.

The invention is illustrated by the following examples that are intended to be illustrative and not limiting in nature.

EXAMPLES

Materials and Methods

Common chemicals and solvents including acetonitrile, benzene, triethylamine, dichloromethane, hexane, acetone, DMSO, 3-(N,N-dimethylamino)propan-1-ol, 1-octanol, bis (N,N-diisopropylamino)chlorophosphine, anhydrous solvents (MeCN, $CH_2Cl_2$, $C_6H_6$) and deuterated solvents ($C_6D_6$, DMSO-$d_6$) were all purchased from commercial sources (Fisher or Aldrich) and used without further purification.

5'-O-(4,4'-Dimethoxytrityl)-2'-deoxythymidine, $N^6$-benzoyl-5'-O-(4,4'-dimethoxytrityl)-2'-deoxyadenosine and $N^4$-benzoyl-5'-O-(4,4'-dimethoxytrityl)-2'-deoxycytidine were purchased from ChemGenes and were used as received. All ancillary reagents commonly used in solid-phase DNA/RNA synthesis including 3H-1,2-benzodithiol-3-one 1,1-dioxide, 3-(dimethylaminomethylidene)amino-3H-1,2,4-dithiazole-3-thione and succinylated long chain alkylamine controlled-pore glass (CPG) support functionalized with either 2'-deoxythymidine, $N^6$-benzoyl-2'-deoxyadenosine or $N^4$-benzoyl-2'-deoxycytidine, as the leader nucleoside, were obtained from Glen Research and used without further purification. The PNA and PMO oligomers listed in Table 1 were purchased from PNA Bio Inc. and Gene Tools LLC, respectively, and were used as received.

Flash chromatography purifications were performed on glass columns (6.0 cm or 2.5 cm I.D.) packed with silica gel 60 (EMD, 230-400 mesh), whereas analytical thin-layer chromatography (TLC) analyses were conducted on 2.5 cm×7.5 cm glass plates coated with a 0.25 mm thick layer of silica gel 60 $F_{254}$ (EMD).

$^1$H-Decoupled $^{31}$P NMR analysis of compounds 1-6 was performed using an NMR spectrometer operating at 121.5 MHz (300 MHz for $^1$H). Samples were maintained at a temperature of 298° K.; all spectra were recorded in deuterated solvents and chemical shifts δ were reported in parts per million (ppm) relative to appropriate internal references.

High resolution mass spectra of compounds 1-6 were obtained using a Bruker Daltonics ApexQ FT-ICR mass spectrometer equipped with a 12 T magnet. Electrospray ionization in positive ion mode was used to generate $[M+H]^+$ and $[M+Na]^+$ ions out of test samples [0.01 mg dissolved in 1 mL of 10 mM ammonium acetate in MeCN: $H_2O$ (1:1 v/v)]. Spectra were externally calibrated using 0.5 mg/mL solution of CsI in water, which yielded a series of peaks in the mass range used for analysis (200-2000 m/z).

Cell culture reagents including Dulbecco's Minimum Essential Medium (DMEM) supplemented with 10% heat-inactivated fetal calf serum, L-glutamine, sodium pyruvate, penicillin, streptomycin, hygromycin, propidium iodide, Lipofectamine™ 2000 and Trypsin, were obtained from Invitrogen (Life Technologies). Phenol red MEM medium, Phenol red-free MEM medium and 0.4% Trypan Blue were purchased from MediaTech. Monensin (Sigma) was kindly provided by Dr. James Keller (CBER, FDA).

Flat-bottom 96-well plates were purchased from BD-Falcon. The CCK-8 Kit for cytotoxicity studies was purchased from Dojindo Molecular Technologies.

Scheme 1. Chemical synthesis of the deoxyribonucleoside phosphoramidites used in the solid-phase synthesis of PS-dT8[3+] and PS-dA8[3+]. DMTr, 4,4'dimethoxytrityl; Thy, thymin-1-yl; Ade$^{Bz}$, $N^6$-benzoyladenin-9-yl; Cyt$^{Bz}$, $N^4$-benzoylcytosin-1-yl.

$$(i\text{-}Pr_2N)_2PCl \xrightarrow[2\ h,\ 25°\ C.]{ROH,\ Et_3N,\ C_6H_6} (i\text{-}Pr_2N)_2POR$$

$$R = CH_2CH_2CH_2N(CH_3)_2 \text{ or } CH_2(CH_2)_6CH_3$$

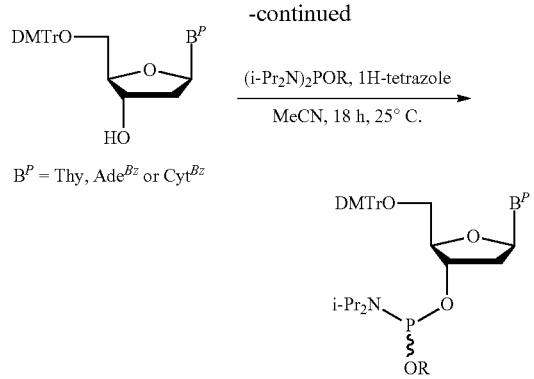

$B^P$ = Thy, Ade$^{Bz}$ or Cyt$^{Bz}$

1 $B^P$ = Thy, R = CH$_2$CH$_2$CH$_2$N(CH$_3$)$_2$
2 $B^P$ = Thy, R = CH$_2$(CH$_2$)$_6$CH$_3$
3 $B^P$ = Ade$^{Bz}$, R = CH$_2$CH$_2$CH$_2$N(CH$_3$)$_2$
4 $B^P$ = Ade$^{Bz}$, R = CH$_2$(CH$_2$)$_6$CH$_3$
5 $B^P$ = Cyt$^{Bz}$, R = CH$_2$CH$_2$CH$_2$N(CH$_3$)$_2$
6 $B^P$ = Cyt$^{Bz}$, R = CH$_2$(CH$_2$)$_6$CH$_3$

Preparation of N,N,N',N'-tetraisopropyl-O-[3-(N,N-dimethylamino)prop-1-yl]phosphordiamidite: To a stirred solution of 3-(N,N-dimethylamino)propan-1-ol (436 µL, 3.70 mmol) and bis(N,N-diisopropylamino)chlorophosphine (1.00 g, 3.70 mmol) in anhydrous benzene (20 mL) was added, under inert atmosphere, Et$_3$N (1.00 mL, 7.17 mmol). Progress of the reaction was monitored by $^{31}$P NMR spectroscopy; formation of the product ($\delta_P$ 122.4 ppm) was found to be complete within 2 h at ~25° C. The suspension was passed through a glass column packed with silica gel (~15 g), which had been pre-equilibrated in benzene:Et$_3$N (9:1 v/v); the filtrate was evaporated to an oil under reduced pressure. The oily material was dissolved in dry benzene (10 ml) and the resulting solution was swirled in a dry ice-acetone bath. The frozen material was lyophilized under high vacuum to give the phosphordiamidite as a viscous oil (1.10 g, 3.29 mmol, 88%), which was of sufficient purity to be used without further purification in the preparation of the deoxyribonucleoside phosphoramidites 1, 3 and 5.

Preparation of N,N,N',N'-Tetraisopropyl-O-[octan-1-yl]phosphordiamidite: The preparation of this compound was performed at the same scale and under conditions similar to those employed for the synthesis of 1 with the exception of using 1-octanol (583 µl, 3.70 mmol) instead of 3-(N,N-dimethylamino)propan-1-ol. The phosphordiamidite 2 was isolated as a viscous oil, the yield of which was similar to that obtained for 1, after silica gel purification. The phosphordiamidite was used without further purification in the preparation of deoxyribonucleoside phosphoramidites 4 and 6.

The preparation of N,N,N',N'-tetraisopropyl-O-[octan-1-yl]phosphordiamidite was performed at the same scale, under similar conditions, using 1-octanol (583 µL, 3.70 mmol) instead of 3-(N,N-dimethylamino)propan-1-ol. The phosphordiamidite was isolated as a viscous oil in a similar yield, after silica gel purification, and used directly in the preparation of the deoxyribonucleoside phosphoramidites 2, 4 and 6.

General procedure for the preparation of deoxyribonucleoside phosphoramidites (1-6): To a stirred solution of N,N,N',N'-tetraisopropyl-O-[3-(N,N-dimethylamino)prop-1-yl]phosphordiamidite or N,N,N,N'-tetraisopropyl-O-[octan-1-yl]phosphordiamidite (2.0 mmol) in MeCN (20 mL) was added 4,4'-dimethoxytriyl deoxythymidine, N$^6$-benzoyl-4,4'-dimethoxytrityl 2'-deoxyadenosine or N$^4$-benzoyl-4,4'-dimethoxytrityl 2'-deoxycytidine (1.0 mmol) along with 0.45 M 1H-tetrazole in MeCN (2.2 mL, 1.0 mmol). The reaction mixture was stirred for 18 h at ~25° C. The reaction mixture was then concentrated under reduced pressure to a gummy material; the crude phosphoramidite was purified by chromatography on silica gel (~25 g), which was equilibrated in a solution of hexane:Et$_3$N (95:5 v/v). The product was eluted from the column using a gradient of CH$_2$Cl$_2$ (0→95%) in hexane: Et$_3$N (95:5 v/v). Fractions containing the pure phosphoramidite, as indicated by TLC, were pooled together and were evaporated to dryness under low pressure. The foamy material was dissolved in dry benzene (5 mL) and the resulting solution was manually stirred in a dry ice-acetone bath. The frozen material was then lyophilized under high vacuum to give the phosphoramidite 1-6 as a white powder, the yields of which were in the range of (75-85%).

5'-O-(4,4'-Dimethoxytrityl)-3'-O—[(N,N-diisopropylamino)(3-[N,N-dimethylamnino]prop-1-yl)oxy]phosphinyl-2'-deoxythymidine (1). $^{31}$P NMR (121 MHz, C$_6$D$_6$): δ 148.8, 148.3. +HRMS: calculated for C$_{42}$H$_{57}$N$_4$O$_8$P [M]$^+$ 777.3986, found 777.3984.

5'-O-(4,4'-Dimethoxytrityl)-3'-O—[(N,N-diisopropylamino)(octan-1-yl)oxy]phosphinyl-2'-deoxythymidine (2). $^{31}$P NMR (121 MHz, C$_6$D$_6$): δ 148.6, 147.9. +HRMS: calculated for C$_{45}$H$_{62}$N$_3$O$_8$P [M+H]$^+$ 804.4353, found 804.4338.

N$^6$-Benzoyl-5'-O-(4,4'-dimethoxytrityl)-3'-O—[(N,N-diisopropylamino)(3-[N,N-dimethylamino]prop-1-yl)oxy]phosphinyl-2'-deoxyadenosine (3). $^{31}$P NMR (121 MHz, C$_6$D$_6$): δ 148.3. +HRMS: calculated for C$_{49}$H$_{60}$N$_7$O$_7$P [M+H]$^+$ 890.4364, found 890.4353.

N$^6$-Benzoyl-5'-O-(4,4'-dimethoxytrityl)-3'-O—[(N,N-diisopropylamino)(octan-1-yl)oxy]phosphinyl-2'-deoxyadenosine (4). $^{31}$P NMR (121 MHz, C$_6$D$_6$): δ 148.4, 148.3. +HRMS: calculated for C$_{52}$H$_{65}$N$_6$O$_7$P [M+H]$^+$ 917.4725, found 917.4767.

N$^4$-Benzoyl-5'-O-(4,4'-dimethoxytrityl)-3'-O—[(N,N-diisopropylamino)(3-[N,N-dimethylamino]prop-1-yl)oxy]phosphinyl-2'-deoxycytidine (5). $^{31}$P NMR (121 MHz, C$_6$D$_6$): δ 148.9, 148.6. +HRMS: calculated for C$_{48}$H$_{60}$N$_5$O$_8$P [M+H]$^+$ 866.4252, found 866.4241.

N$^4$-Benzoyl-5'-O-(4,4'-dimethoxytrityl)-3'-O—[(N,N-diisopropylamino)(octan-1-yl)oxy]phosphinyl-2'-deoxycytidine (6). $^{31}$P NMR (121 MHz, C$_6$D$_6$): δ 147.8, 147.4.

Solid-phase synthesis of PS-dT$_8$[3+], PS-dT$_{11}$[6+], PS-dT$_{13}$[8+], PS-dT$_{15}$[10+], PS-dT$_{17}$[12+], PS-dA$_8$[3+] and PS-dC$_8$[3+]: Solid-phase synthesis of PS-dT$_8$[3+], PS-dT$_{11}$[6+], PS-dT$_{13}$[8+], PS-dT$_{15}$[10+], PS-dT$_{17}$[12+], PS-dA$_8$[3+] and PS-dC$_8$[3+] was performed on a 0.2 µmole scale using a succinylated long chain alkylamine controlled-pore glass support loaded with either 5'-O-(4,4'-dimethoxytrityl)-2'-deoxythymidine, 5'-O-(4,4'-dimethoxytrityl)-N$^6$-benzoyl-2'-deoxyadenosine or 5'-O-(4,4'-dimethoxytrityl)-N$^4$-benzoyl-2'-deoxycytidine as the leader nucleoside. The syntheses were carried out using an ABI 394 DNA/RNA synthesizer and phosphoramidites 1-6 as 0.1 M solutions in dry MeCN. The coupling reactions were effected in the presence of 1H-tetrazole over a period of 600 s. All ancillary reagents necessary for the preparation of the DNA sequences were purchased and utilized as recommended by the instrument's manufacturer. The oxidation step of the synthesis cycle was performed using 3-(dimethylaminomethylidene)amino-3H-1,2,4-dithiazole-3-thione (0.05 M in pyridine-MeCN (4:6 v/v). This sulfurization step was performed before the capping step and the reaction time for these steps was 600 s and 120 s, respectively. The iterative cleavage of the 5'-DMTr group was carried out over a period of 60 s. Upon complete assembly of the PS-dT$_8$[3+], PS-dT$_{11}$[6+], PS-dT$_{13}$[8+], PS-dT$_{15}$[10+], PS-dT$_{17}$[12+], PS-dA$_8$[3+] and PS-dC$_8$[3+] sequences, the PS-dT$_8$[3+], PS-dT$_{11}$[6+], PS-dT$_{13}$[8+], PS-dT$_{15}$[10+], PS-dT$_{17}$[12+] synthesis columns were placed into a stainless steel pressure vessel and exposed to pressurized methylamine gas (~2.5 bar at 25° C.) over a period of 3 min, whereas the PS-dA$_8$[3+] and PS-dC$_8$[3+] synthesis columns were subjected to pressurized ammonia gas (~10 bar at 25° C.) over a period of 12 h.

Upon removal of residual methylamine or ammonia gas from the pressure container, the PS-dT$_8$[3+], PS-dT$_{11}$[6+], PS-dT$_{13}$[8+], PS-dT$_{15}$[10+], PS-dT$_{17}$[12+], PS-dA$_8$[3+] and PS-dC$_8$[3+] sequences were individually eluted off their respective synthesis columns using a solution (0.5 mL) of Et$_3$N:MeCN:H$_2$O (1:60:39 v/v/v). Each PS-dT$_8$[3+], PS-dT$_{11}$[6+], PS-dT$_{13}$[8+], PS-dT$_{15}$[10+], PS-dT$_{17}$[12+], PS-dA$_8$[3+] or PS-dC$_8$[3+] solution was evaporated to dryness using a stream of air. Crude PS-dT$_8$[3+], PS-dT$_{11}$[6+], PS-dT$_{13}$[8+], PS-dT$_{15}$[10+], PS-dT$_{17}$[12+], PS-dA$_8$[3+] and PS-dC$_8$[3+] sequences were each stored at −20° C. and used without purification.

PS-dT$_8$[3+]: +ESI-MS: calculated for C$_{127}$H$_{205}$N$_{19}$O$_{47}$P$_7$S$_7$ [M+H]$^+$ 3189, found 3189.
PS-dT$_{11}$[6+]:+ESI-MS: calculated for C$_{172}$H$_{280}$N$_{28}$O$_{65}$P$_{10}$S$_{10}$ [M+2H]$^{+2}$2203, found 2203.
PS-dT$_{13}$[8+]:+ESI-MS: calculated for C$_{202}$H$_{330}$N$_{34}$O$_{77}$P$_{12}$S$_{12}$ [M+2H]$^{+2}$2609, found 2608
PS-dT$_{15}$[10+]:+ESI-MS: calculated for C$_{232}$H$_{380}$N$_{40}$O$_{89}$P$_{14}$S$_{14}$ [M+2H]$^{+2}$ 3015, found 3014
PS-dT$_{17}$[12+]:+ESI-MS: calculated for C$_{262}$H$_{430}$N$_{46}$O$_{101}$P$_{16}$S$_{16}$ [M+2H]$^{+2}$ 3421, found 3419
PS-dA$_8$[3+]: +ESI-MS: calculated for C$_{127}$H$_{196}$N$_{43}$O$_{31}$P$_7$S$_7$ [M+H]$^+$ 3261, found 3261.
PS-dC$_8$[3+]: +ESI-MS: calculated for C$_{119}$H$_{196}$N$_{27}$O$_{39}$P$_7$S$_7$ [M]$^+$3068, found 3068.

Thermal denaturation protocol: dTtaPS was mixed with the polyA-tailed PNA oligomer 10 in either 1×PBS buffer (pH 7.4) or 1.0 M NaCl in 1×PBS buffer while keeping the total strand concentration at ca. 2 µM. Thermal denaturation profiles (absorbance vs temperature) of the dTtaPS:10 complex was measured at 260 nm using a UV/Vis spectrophotometer equipped with a Peltier temperature controller and interfaced with a personal computer. Denaturation of the complex was performed over a temperature range of −5 to 60° C. The temperature was ramped at the rate of 1° C./min; temperature measurements were recorded at every 1° C. with an equilibration time of 30 s between each measurement. Heating and cooling profiles were recorded.

Cell culture: HEK293 (ATCC® CRL-1573'), HeLa (ATCC® CCL-2™) MCF7 (ATCC® HTB-22™) CHO-K1 (ATCC® CCL-61™), GC-2spd(ts) (ATCC® CRL-2196™) and SK—N—SH (ATCC® HTB-11™) cell lines were purchased from ATCC. All cell lines were exponentially grown in ATCC recommended media containing 100 U penicillin and 100 µg/ml streptomycin. The HeLa pLuc 705 cell line, kindly provided by Prof. Rudolph Juliano (University of North Carolina, Chapel Hill), was exponentially grown in Dulbecco's Minimum Essential Medium (DMEM) supplemented with 10% heat-inactivated fetal calf serum (FBS), 1.5 mM L-glutamine, 1.0 mM sodium pyruvate, 100 U penicillin, 100 µg/mL streptomycin and 200 µg/mL hygromycin, and maintained at 37° C. in a humidified-incubator under 5% CO$_2$.

Complex formation between PNA or PMO oligomers and dTtaPS or dAtaPS: Appropriate amounts of PNA or PMO oligomers were diluted in serum-free OptiMEM™ (20 µl). dTtaPS or dAtaPS was added to the oligomer solution to achieve a final concentration that is twice that of the oligomer. After 30 min incubation at 37° C., the PNA or PMO oligomer: dTtaPS or dAtaPS complexes were stored at 4° C. for 15 minutes or until used. Stock solutions (2×) of the complexes were made by adding OptiMEM™ to appropriate volumes.

Flow cytometry analysis of cellular uptake in live cells: The internalization of fluorescently-labeled PNA or PMO sequences (Table 1) in HEK 293, HeLa, MCF7 and SK—N—SH cells was assessed by flow cytometry. Cells were seeded in a 96-well plate (10$^4$ cells/well) and allowed to grow at 37° C. for 24 h in 10% FBS-MEM. The culture medium of each well was then replaced with fresh medium (100 µl) containing any of the fluorescently-labeled PNA or PMO sequences, the final concentration of which was 1 µM. After an incubation of 18 h at 37° C., the medium was removed from each well by suction and 0.25% Trypsin (50 µl) was added. Upon complete cell detachment, a solution (100 µl) of ice-cold 2% FBS in phosphate-buffered saline (PBS, pH 7.4) was added to each well. The cells were collected into tubes, to which was added 0.4% Trypan blue (50 µl) and 200 M monensin (20 µl), and analyzed by fluorescence-activated cell sorting (FACS) using a BD FACScan™ flow cytometer. A total of 5000 events were counted and the results were reported as a percentage of the cells that have internalized the fluorescently-labeled oligomers.

Luciferase assay protocol: HeLa pLuc 705 cells were seeded in a 96-well plate (2×10$^4$ cells/well) and allowed to grow at 37° C. for 18 h in 10% FBS-DMEM. The culture medium of each well was then replaced with either fresh serum-free or 20% serum-containing OptiMEM™ (50 µl) for experiments intended to be performed in serum-free or in 10% serum-containing media. A 2× solution of PNA or PMO oligomer:dTtaPS or dAtaPS complexes (50 µl) was added to the cells in order to achieve pre-determined complex concentrations, as indicated in the Figures. After a 4-hour incubation at 37° C., 20% FBS in OptiMEM™ (100 µl was added to serum-free experiments and cells were incubated for an additional 18 h at 37° C. The media was then removed by suction and the cells were mixed with a cell lysis reagent (50 µl) and agitated at ambient temperature for 10 minutes. The cell lysate (30 µl) was placed in a white 96-well plate and Bright-Glo™ reagent (20 µl) was added. Luciferase activity was measured using a microplate reader. For each well, luminescence was integrated over a period of 1 sec and recorded as relative light units (RLU). Luminescence measurements were normalized to the amount of protein present in the test sample.

Protein concentration measurements: Protein concentrations were determined from cell lysates (5 µL), which were obtained using a lysis reagent that is compatible with the Coomassie™ (Bradford) reagent, as per the manufacturer's instructions.

Energy-dependence of the dTtaPS-assisted internalization of PNA oligomer 10 in HeLa pLuc 705 cells: HeLa pLuc 705 cells were seeded in a 96-well plate (2×10$^4$ cells/well) and allowed to grow at 37° C. for 18 h in 10% FBS-DMEM. While the cell culture was maintained at 37° C. or 4° C., a 2× solution of a PNA oligomer 10:dTtaPS complex was prepared as described above. The cell culture medium was replaced with the PNA oligomer:dTtaPS complex solution to provide an oligomer and dTtaPS final concentration of 1.0 M and 2.0 M, respectively. After an incubation of 1 h at 37° C. or 4° C., the medium was removed by suction and luciferase activity was measured as described above in the Luciferase assay protocol. Luminescence measurements were normalized to the amounts of protein present in the test samples and reported as percent luminescence remaining relative to that of the experiment performed at 37° C.

Endocytic pathway assays: HeLa pLuc 705 cells were seeded in a 96-well plate and grown in 10% FBS-DMEM as described above. The cell culture was then pre-incubated for 30 min at 37° C. in the presence of chlorpromazine, nystatin or 5-(N-ethyl-N-isopropyl)amiloride (EIPA), the final concentration of which was 30 µM, 50 µM or 1 mM, respectively. A 2× solution of PNA oligomer 10:dTtaPS complex was added to the cells to provide an oligomer and dTtaPS final concentration of 1.0 µM and 2.0 µM, respectively. The cells were then incubated for an additional 30 min at 37° C., whereupon luciferase activity was measured as described above in the Luciferase assay protocol. Luminescence measurements were normalized to the amounts of protein present in the test samples and reported as percent luminescence remaining relative to that of the experiment performed in the absence of endocytic pathway inhibitors.

Competition assay: HeLa pLuc 705 cells were seeded in a 96-well plate and grown in 10% FBS-DMEM as described above. Predetermined amounts of polyA-tailed PNA oligomer 10 and octathymidilyl DNA phosphorothioate (PS-$dT_8$) were placed in individual microfuge tubes so that the molar ratio of PNA:PS-$dT_8$ in each tube was 1:1, 1:2 or 1:4. OptiMEM™ (20 µl) was added to each of the three tubes, which were then placed in a heating block pre-heated to 60° C. After 2 min, the tubes were removed from the heating block, allowed to cool slowly to 20° C., and then, left standing in a cold room (4° C.) for 15 min. dTtaPS was added to the mixture of oligomers of each tube to achieve a concentration that is equimolar to that of the PNA oligomer 10. After a 30 min incubation at 37° C., the PNA/PS-$dT_8$:dTtaPS complexes were stored at 4° C. for 15 minutes or until used. A 2× solution of the PNA/PS-$dT_8$:dTtaPS complexes taken from each microfuge tube was added to the cells to provide a final concentration of 1.0 µM for the PNA oligomer, 1.0, 2.0 or 4.0 µM for PS-$dT_8$ and 1.0 µM for dTtaPS. The cells were then incubated for an additional 30 min at 37° C., whereupon luciferase activity was measured as described above in the Luciferase assay protocol. Luminescence measurements were normalized to the amounts of protein present in the test samples and reported as percent luminescence remaining relative to that of the experiment performed in the absence of PS-$dT_8$.

Confocal microscopy analysis of dTtaPS-assisted internalization of PNA or PMO oligomers in HeLa pLuc 705 cells: HeLa pLuc 705 cells (5×10⁴ cells/well) were seeded in 8-well chambered slides and cultured for 24 h at 37° C. in 10% FBS-MEM (200 µl). The culture medium of each well was then replaced with 20% FBS containing fresh medium (200 µl) and the fluoresceinated PNA or PMO oligomer: dTtaPS complex that was prepared as described above to provide an oligomer and dTtaPS final concentration of 1.0 M and 2.0 µM, respectively. After a 12 h incubation at 37° C., the medium was removed and a 0.4% Trypan Blue solution (200 µl) was added to quench the fluorescence stemming from extracellular fluoresceinated oligonucleotides. After a period of 5 minutes at ambient temperature, the cells were washed twice with PBS (pH 7.4, 200 µl) followed by the addition of fresh phenol red-free DMEM (200 µl) supplemented with 10% FBS. The intracellular distribution of fluorescence was determined without fixation using a Leica SP8 confocal microscope system and analysed using the Leica LASAF software. Hoechst 33342 was used, in accordance with the manufacturer's staining protocols, for the detection of nuclei. Images were acquired at a 63× magnification.

Example 1: Complex Formation Between PNA/PMO Oligomers and PS-$dT_8$[3+] or PS-$dA_8$[3+]

Appropriate amounts of PNA/PMO oligomers were diluted in OptiMEM™ (20 µL) to achieve the concentration of 1 µM or as indicated in the Figures. PS-$dT_8$[3+] or PS-dAs[3+] was added to the above oligomer solutions. After a 30 min incubation at 37° C., the PNA/PMO oligomer:PS-$dT_8$[3+] or PS-$dA_8$[3+] complexes were removed and kept at 4° C. for 15 minutes or until used. Stock solutions of the complexes were made by adding OptiMEM™ to appropriate volumes.

Luciferase Assay: Prior to performing experiments, HeLa pLuc 705 cells were seeded in a 96-well plate (2×10⁴ cells/well) and allowed to grow at 37° C. for 18 h in 10% FBS DMEM. The culture medium of each well was then replaced with either fresh 50 µL serum free or 20% serum-containing OptiMEM™ for experiments intended to be performed in serum free or in 10% serum-containing media. A 2× solution of the PNA/PMO oligomer:PS-$dT_8$[3+] or PS-$dA_8$[3+] complexes (50 µL) was added to the cells in order to achieve a pre-determined concentration as indicated in the figures. After a 4-hour incubation at 37° C., 20% FBS in OptiMEM (100 µL) was added to serum free experiments and cells were incubated for an additional 18 h at 37° C. The media was then removed by suction and the cells were mixed with a cell lysis reagent (50 µL) and agitated at ambient temperature over a period of 10 minutes. The cell lysate (30 µL) was placed in white 96-well plate and Bright-Glow™ reagent (20 µL) was added. Luciferase activity was measured using a microplate reader. For each well, luminescence was integrated over a period of 1 sec and recorded as relative light units (RLU). Luminescence was normalized based on the amount of protein present in the sample.

Protein concentration: Protein concentrations were determined from cell lysates (5 µL), which were obtained using a lysis reagent that is compatible with the Coomassie™ (Bradford) reagent, as per manufacturer's instructions.

Example 2: Delivery of siRNA Targeting Enhanced Green Fluorescent Protein (eGFP)

A trans-acting DNA transfection element (PS-$dT_{11}$[6+]) has been engineered for the delivery of a commercial siRNA (Ambion®Silencer® GFP) targeting the short half-life eGFP mRNA in Vero cells and to demonstrate the cellular internalization and functional activity of the siRNA at inhibiting the production of eGFP.

Typically, an appropriate volume of a 20 µM siRNA stock solution was added to OptiMEM™ (20 µL). The required volume of a 1 mM stock solution of trans-acting DNA transfection element (PS-$dT_{11}$ [6+]) was added to each siRNA solution. The resulting siRNA/PS-$dT_{11}$ [6+] solutions were incubated for 30 min at ambient temperature. The siRNA:PS-$dT_{11}$[6+] complexes were then diluted with OptiMEM™ to get twice (2×) the desired concentration.

Live Vero pdleGFP cells were seeded in a 96-well plate (2×10⁴ cells/well) and allowed to grow at 37° C. for 18 h in 10% FBS DMEM. The culture medium of each well was then replaced with fresh serum-free or 20% FBS OptiMEM™ (50 µL) medium. The 2× solution of siRNA:

PS-dT$_{11}$[6+] complexes (50 µL) was added to the cells to produce final concentrations of 5 to 40 nM siRNA and 1 M PS-dT$_{11}$[6+] per well. After a 4-h serum-free incubation, 20% FBS in OptiMEM™ (100 µL) was added to each well and the cell cultures were incubated at 37° C. for an additional 18 h. The cell culture media was removed by suction and 0.25% trypsin (50 µL) was added. Upon complete cell detachment, a solution (100 µL) of ice-cold 2% FBS in phosphate-buffered saline (PBS, pH 7.4) was added. The cells of each well were collected into tubes, to which was added 0.4% Trypan blue (50 µL), and were analyzed by fluorescence activated cell sorting (FACS) using a BD FACScan™ flow cytometer. A total of 1×10$^4$ events were counted and the percentage of eGFP knockdown was recorded.

Figure 21:
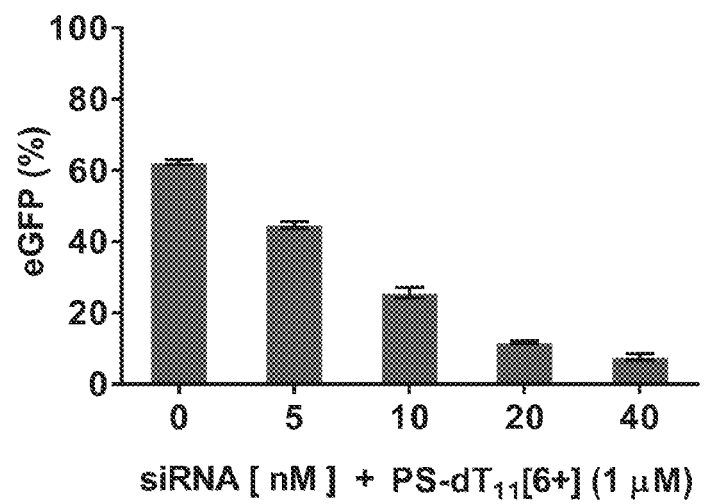
FIG. 21 shows dose-response relationship, in serum-containing medium, between the inhibition of eGFP production and the external concentration of siRNA being used for internalization in Vero cells. The data is presented as the percentage of cells expressing eGFP.

The delivery of siRNA in Vero cells, using the trans-acting DNA transfection element PS-dT$_{11}$[6+], resulted in an eGFP knockdown commensurate to the concentration of the siRNA being internalized (FIG. 21).

Figure 22:
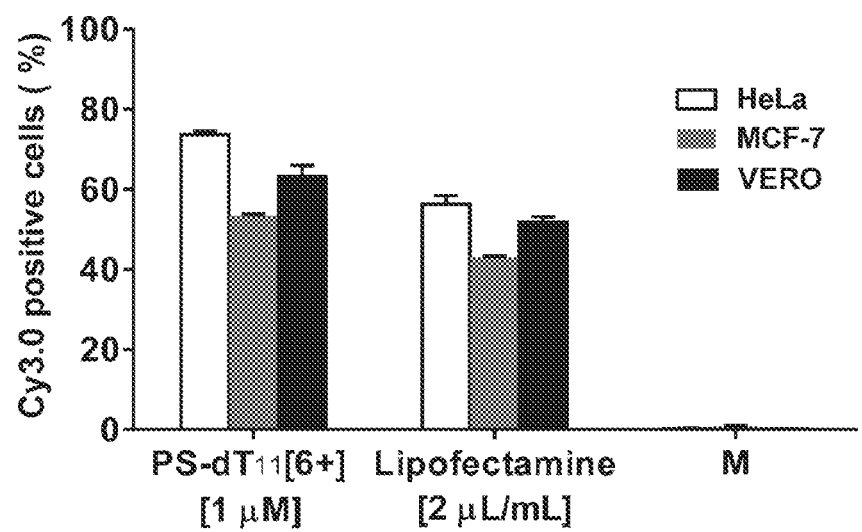
FIG. 22 presents data on the uptake of 20 nM Cy3.0 labeled control siRNA in various mammalian cell lines. Abbreviation: M, medium.
Figure 24A:
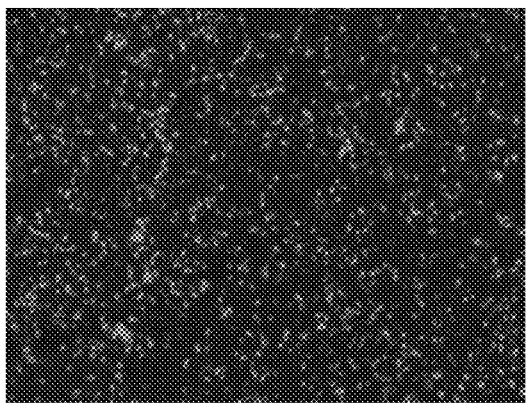
FIG. 24 shows delivery of commercial eGFP expressing plasmid in CHO cells in the absence of serum using (A) PS-dT$_{11}$[6+], (B) PS-dT$_{13}$[8+], (C) PS-dT$_{15}$[10+] or (D) PS-dT$_{17}$[12+] as the transfection reagent, the concentration of which is 5 μM.
Figure 24B:
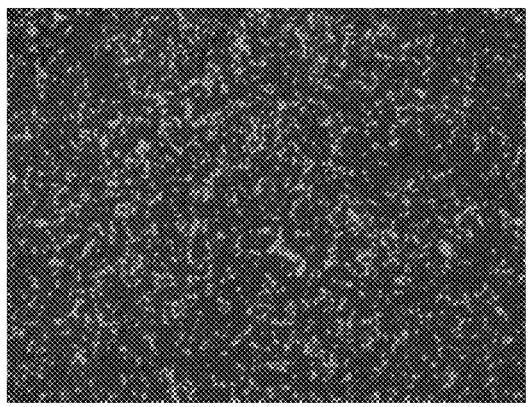
Figure 24C:
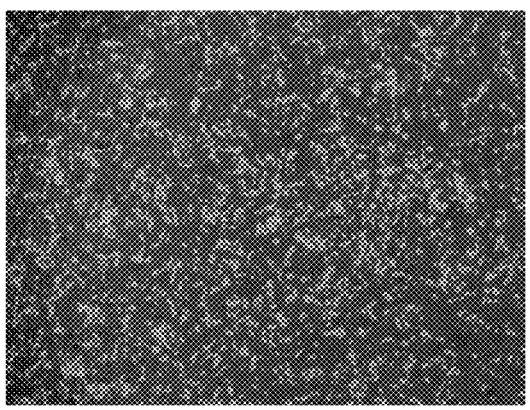
Figure 24D:
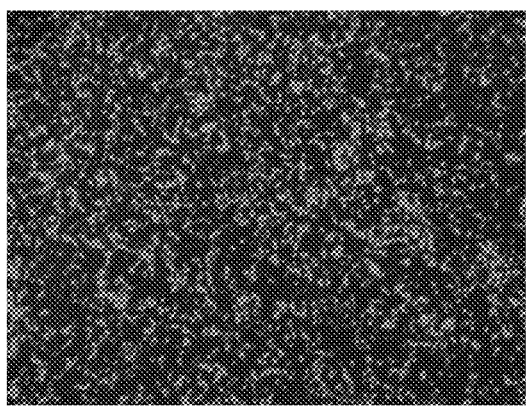
Figure 25A:
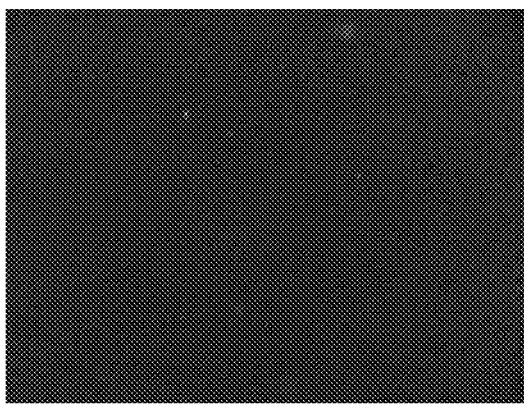
FIG. 25 shows delivery of commercial eGFP expressing plasmid in GC-2 cells in the absence of serum using (A) PS-dT$_{11}$[6+], (B) PS-dT$_{13}$[8+], (C) PS-dTs$_{15}$[10+] or (D) PS-dT$_{17}$[12+] as the transfection reagent, the concentration of which is 5 μM.
Figure 25B:
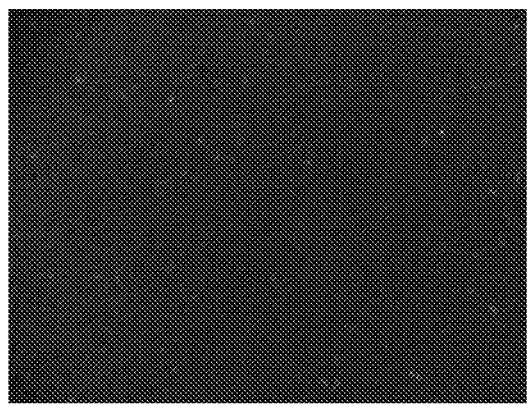
Figure 25C:
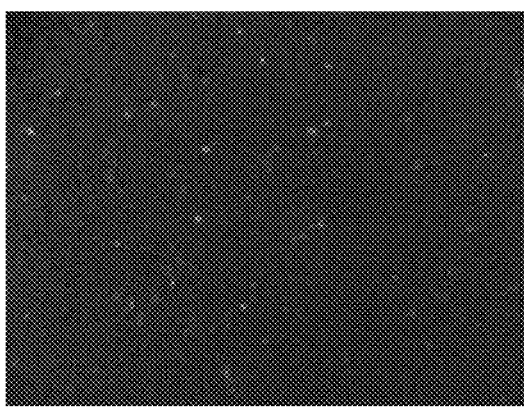
Figure 25D:
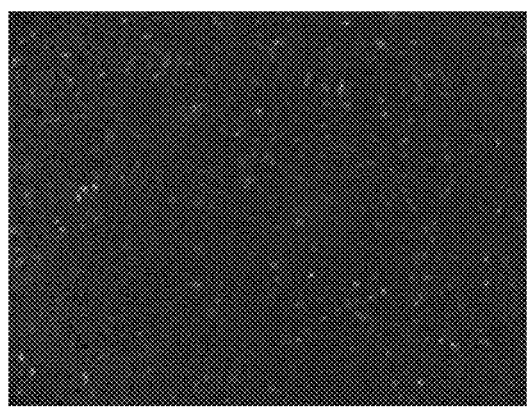
Figure 26A:
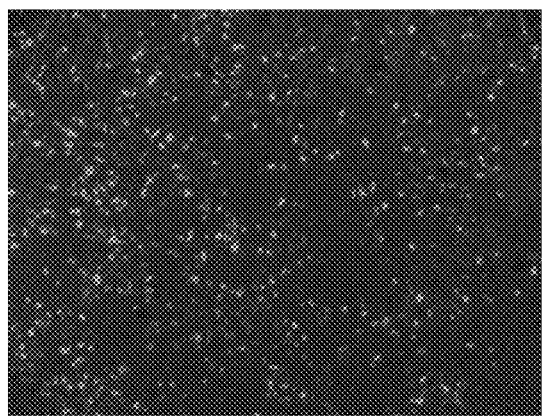
FIG. 26 shows delivery of commercial eGFP expressing plasmid in HEK 293 cells in the absence of serum using (A) PS-dT$_{11}$[6+], (B) PS-dT$_{13}$[8+], (C) PS-dT$_{15}$[10+] or (D) PS-dT$_{17}$[12+] as the transfection reagent the concentration of which is 5 μM.
Figure 26B:
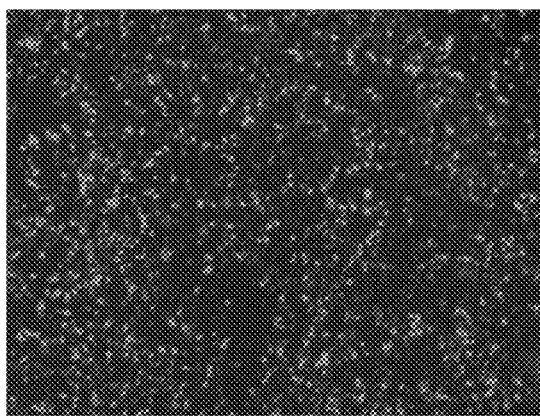
Figure 26C:
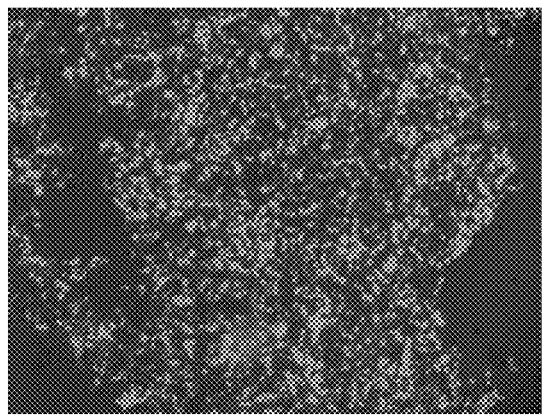
Figure 26D:
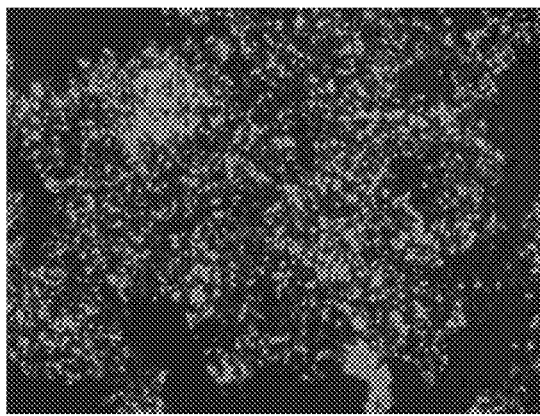
Figure 27A:
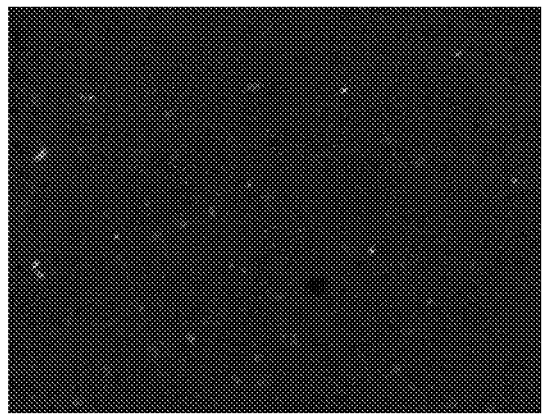
FIG. 27 shows delivery of commercial eGFP expressing plasmid in HeLa cells in the absence of serum using (A) PS-dT$_{11}$[6+], (B) PS-dT$_{13}$[8+], (C) PS-dTs$_5$[10+] or (D) PS-dT$_{17}$[12+] as the transfection reagent the concentration of which is 5 μM.
Figure 27B:
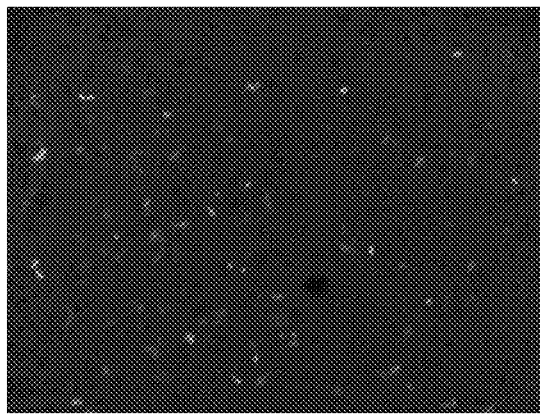
Figure 27C:
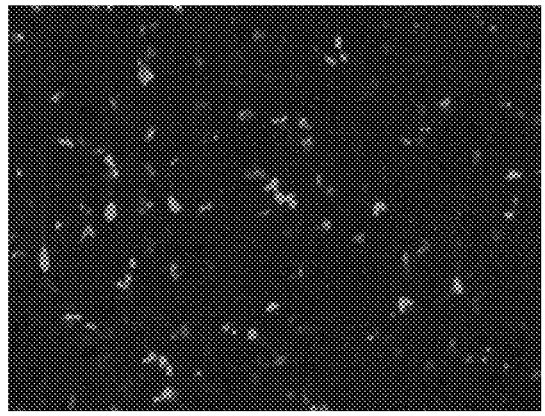
Figure 27D:
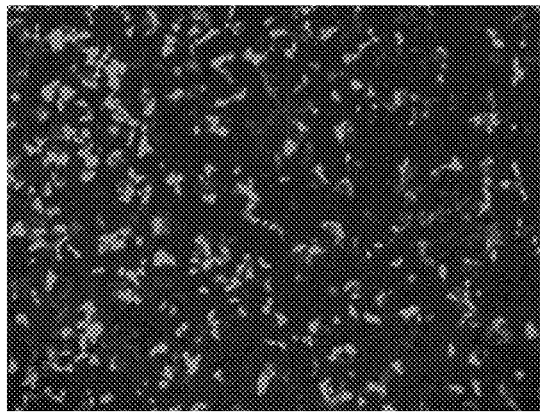

The generality of Cy3.0-labeled control siRNA uptake in various mammalian cell lines when using PS-dT$_{11}$[6+] and Lipofectamine 2000 as transfection reagents is demonstrated by FACS analysis. The results of this analysis are shown in FIG. 22.

Example 3: Delivery of eGFP Plasmid

The trans-acting DNA transfection element PS-dT$_{11}$[6+] was also shown to deliver plasmids in HeLa pLuc cells.

As described above, an appropriate amount of commercial eGFP expressing plasmid was diluted in OptiMEM™ (20 µL). The appropriate amount of trans-acting DNA transfection element PS-dT$_{11}$[6+], PS-dT$_{13}$[8+], PS-dT$_{15}$[10+] or PS-dT$_{17}$[12+] was added to the plasmid DNA solution. The resulting plasmid:PS-dT$_{11}$[6+], PS-dT$_{13}$[8+], PS-dT$_{15}$[10+] or PS-dT$_{17}$[12+] solution was incubated for 30 min at room temperature. The plasmid:PS-dT$_{11}$[6+], PS-dT$_{13}$[8+], PS-dT$_{15}$[10+] or PS-dT$_{17}$[12+] complexes were diluted with OptiMEM™ to get twice (2×) the desired concentration.

Live HeLa pLuc 705, CHO, GC-2, HEK 293 or Hela cells were seeded in a 96-well plate (2×10$^4$ cells/well) and allowed to grow at 37° C. for 18 h in 10% FBS DMEM. The culture medium of each well was then replaced with fresh serum-free OptiMEM™ (50 µL) medium. The 2× solution of plasmid: PS-dT$_{11}$[6+], PS-dT$_{13}$[8+], PS-dT$_{15}$[10+] or PS-dT$_{17}$[12+] complex (50 µL) was added to each well in order to provide 100 ng plasmid and a concentration of 5 M PS-dT$_{11}$[6+], PS-dT$_{13}$[8+], PS-dT$_{15}$[10+] or PS-dT$_{17}$[12+] per well. After a 4-h serum-free incubation, 20% FBS in OptiMEM™ (100 µL) was added and the cell cultures were incubated for an additional 18 h at 37° C.

Images of live cells were recorded using an Olympus fluorescence microscope at 4× and presented in FIG. 23-27.

Example 4

Examples 2 and 3 are repeated using PS-dC$_8$[3+] or PS-dC [6+], PS-dA$_8$[3+] or PS-dA$_{11}$[6+], where appropriate, or transfection elements composed of PS-dT, -dC and -dA moieties.

Example 5: The Chemical Synthesis of dTtaPS and dAtaPS

Figure 2:
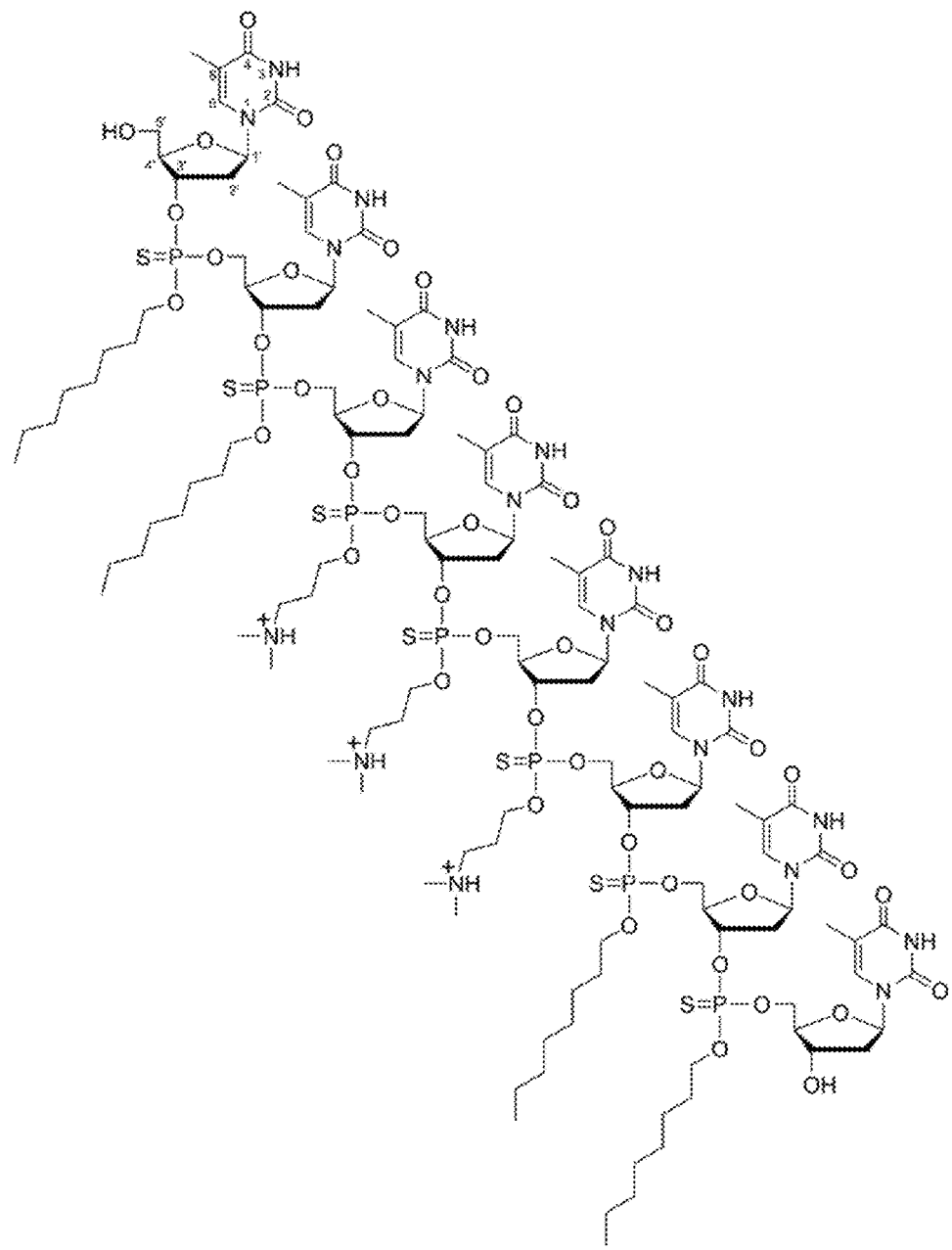
FIG. 2 presents a chemical structure of PS-dT$_8$[3+].
Figure 3:
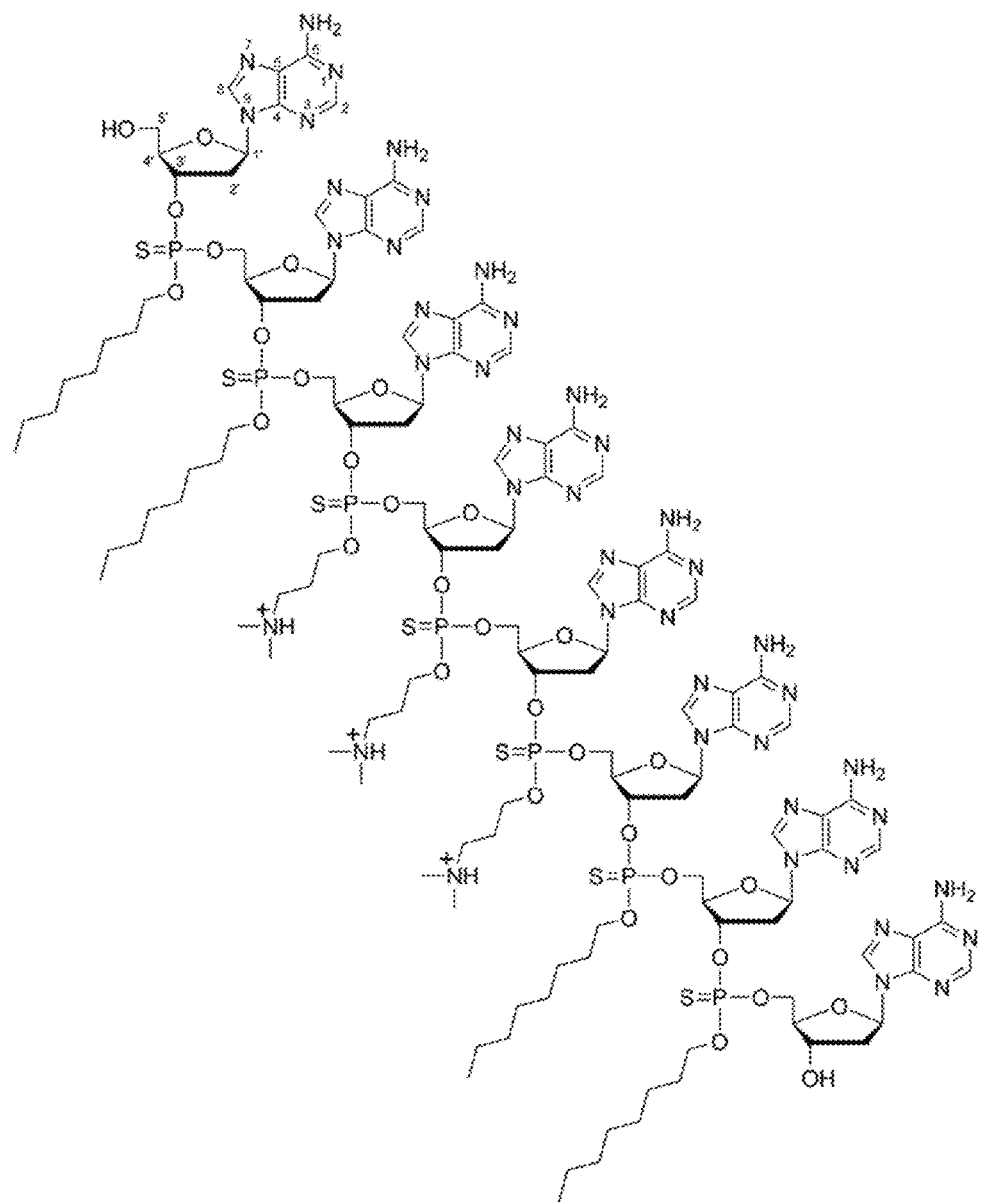
FIG. 3 presents a chemical structure of PS-dA$_8$[3+].

The solid-phase synthesis of dTtaPS and dAtaPS begins with the preparation of the phosphordiamidites, which are required for the preparation of the deoxyribonucleoside phosphoramidites 3-6 (FIG. 9). Thus, the reaction of an equimolar amount of commercial bis(N,N-diisopropylamino)chlorophosphine with either 3-(N,N-dimethylamino)propan-1-ol or 1-octanol in the presence of excess triethylamine in anhydrous benzene, produced the phosphordiamidite in a yield exceeding 85% after purification on silica gel. Treatment of commercially available 4,4'-dimethoxytrityl deoxythymidine or N$^6$-benzoyl-4,4'-dimethoxytrityl 2'-deoxyadenosine with the phosphordiamidite and 1H-tetrazole in a molar ratio of 1:2:1, respectively, in anhydrous MeCN afforded the deoxyribonucleoside phosphoramidites 3-6 (FIG. 2). These phosphoramidites were isolated as white powders in yields of 75-85% after purification on silica gel and lyophilisation from dry benzene. The identity of phosphoramidites 3-6 was confirmed by $^{31}$P-NMR spectroscopy and high-resolution mass spectrometry.

The synthesis of dTtaPS and dAtaPS on appropriately functionalized controlled pore glass (CPG) supports was easily achieved using the deoxyribonucleoside phosphoramidites 3-6 as 0.1 M solutions in MeCN. The coupling time of the 1H-tetrazole-activated phosphoramidites 3-6 was extended to 10 min to maximize stepwise coupling efficiencies, which were determined to be in the order of 98-99% based on the 4,4'-dimethoxytrityl cation assay. Upon exposure to pressurized gaseous amines and release from the CPG support, the purity of diastereomeric dTtaPS and dAtaPS was assessed by C4-RP-HPLC analysis, which revealed broad product peaks consistent with the diastereomeric and amphiphilic nature of these compounds. The purity of dTtaPS and dAtaPS was nonetheless found adequate to support our investigations.

Figure 4:
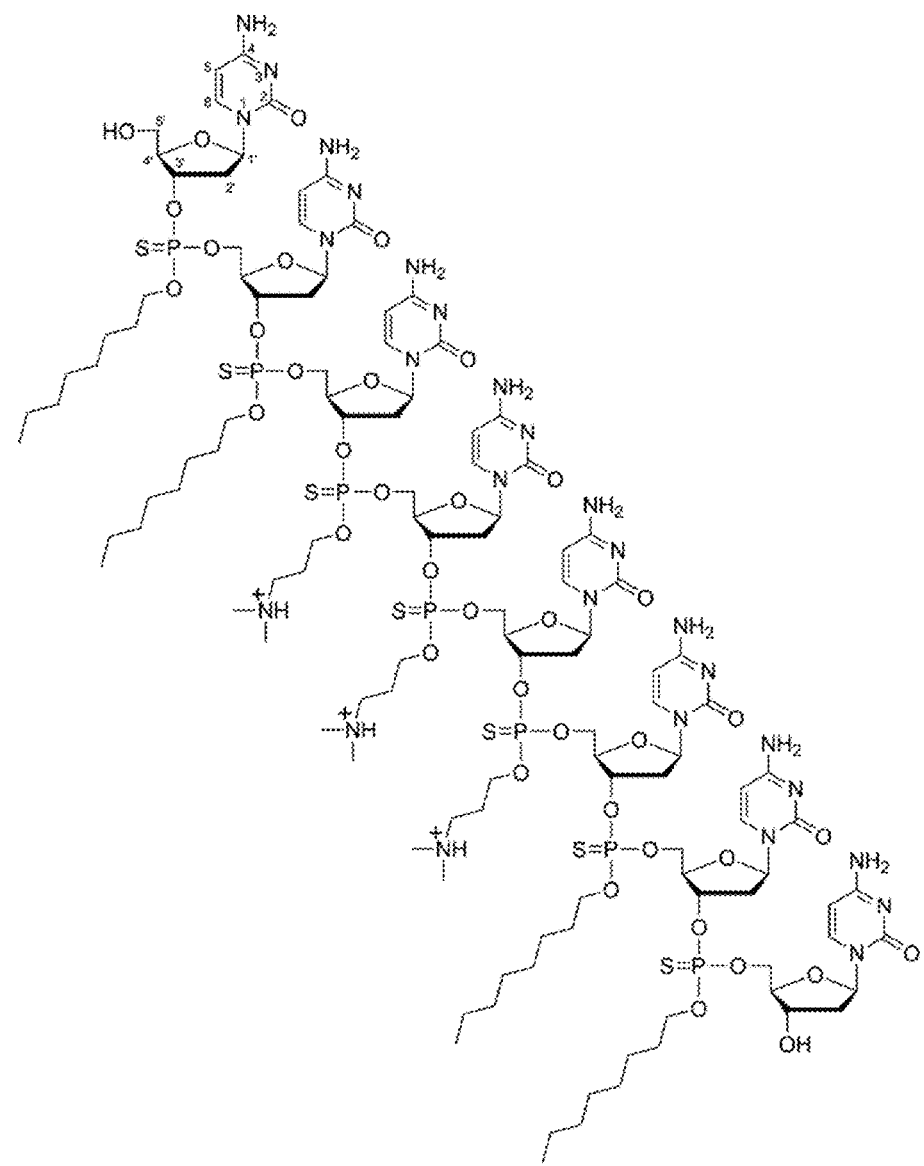
FIG. 4 presents a chemical structure of PS-dC$_8$[3+].
Figure 5:
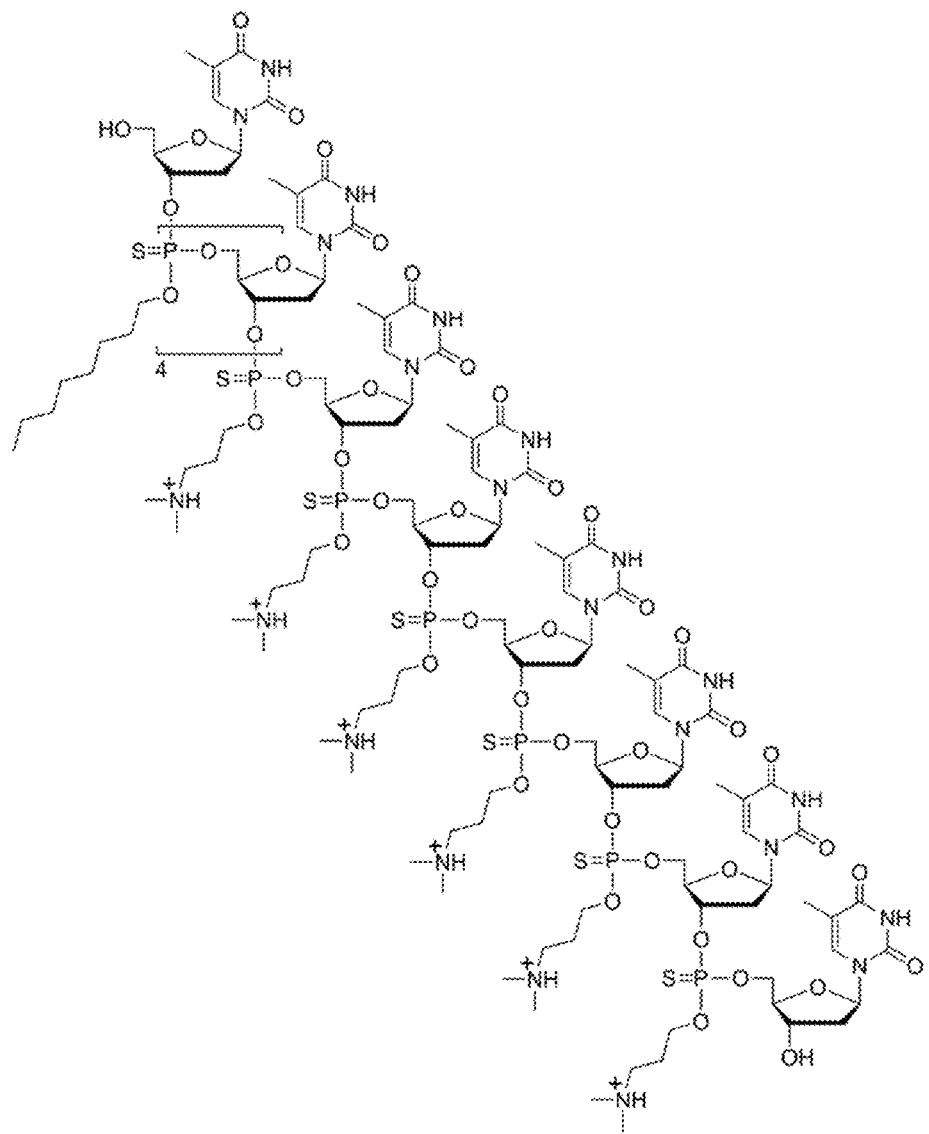
FIG. 5 presents a chemical structure of PS-dT$_{11}$[6+].
Figure 6:
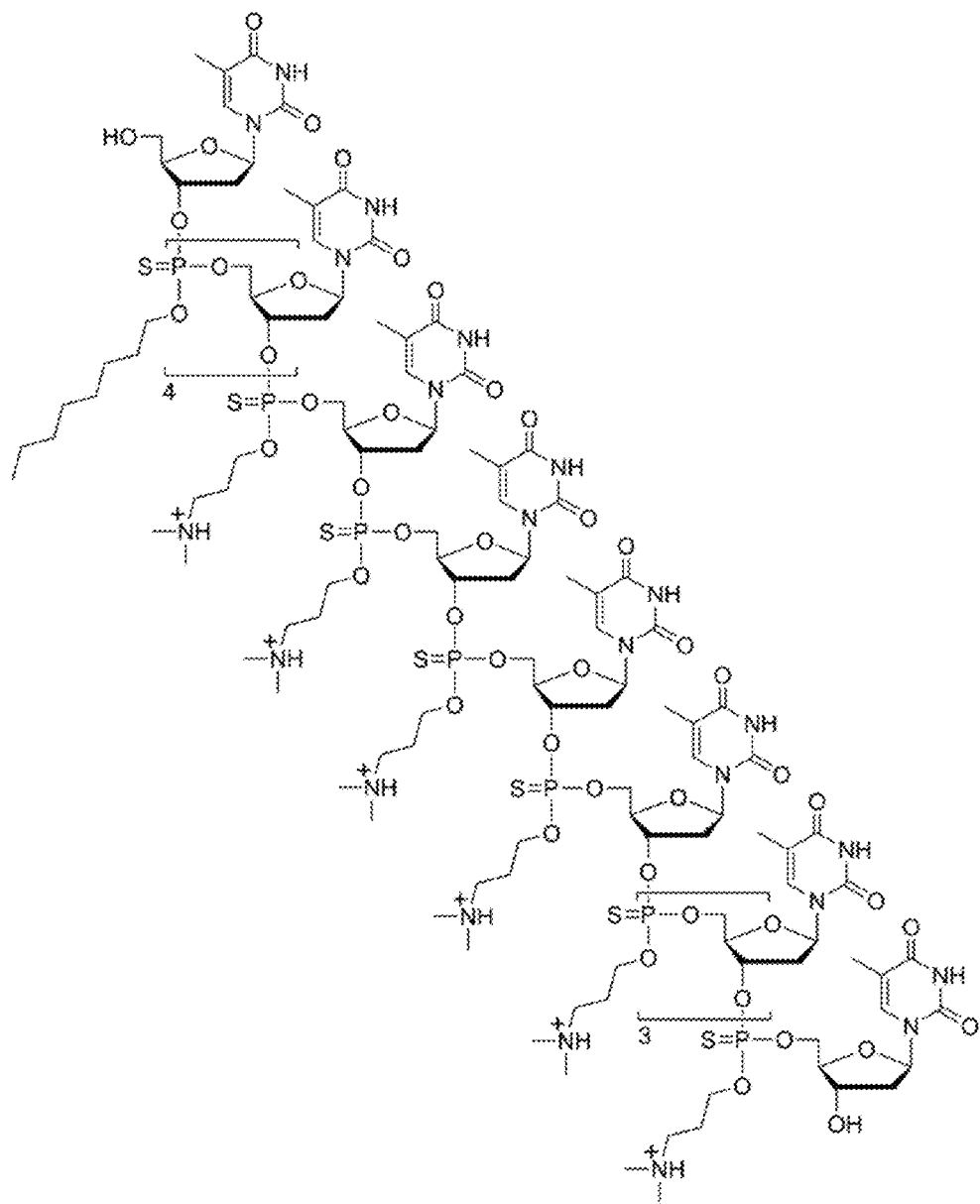
FIG. 6 presents a chemical structure of PS-dT$_{13}$[8+].

Example 6: A Short PNA-polyA Stretch is Necessary and Sufficient for dTtaPS-Mediated Internalization and Bioactivity of PNA Oligomers in Live Mammalian Cells The dTtaPS-mediated cellular internalization of fluorescently-labelled PNA oligomers (Table 1) in HEK 293, HeLa, HeLa pLuc 705, MCF7 and SK—N—SH live cells was evaluated by FACS analysis. As shown in FIG. 11, polyA-tailed PNA oligomers 7 and 8 were efficiently internalized in the presence of dTtaPS in all the cell lines under study. In sharp contrast, the PNA oligomer 9 lacking the polyA stretch was not significantly internalized under similar conditions in any of the cell lines. The efficiency of dTtaPS in mediating the cellular uptake of polyA-tailed PNA oligomers was assessed through a splice correction assay performed in HeLa pLuc 705 cells. The concentration-dependence of luciferase activity production on the dTtaPS-mediated internalization of PNA oligomer 10 in the proposed cell line is shown in FIG. 12 and compared with the luciferase activities measured either from the dTtaPS-assisted deliveries of PNA oligomers 11 and 12 or 2'-OMe RNA sequences 13 and 14 (FIG. 13). As clearly demonstrated in FIG. 12, the PNA oligomer 10 induced splice correction of the pre-mRNA encoding luciferase, in a dose-dependent manner, in the nucleus of the cells. When dTtaPS was absent, no luciferase activity was detected. It should be noted that the lowest concentration of oligomer 10 required for production of luciferase activity has not been investigated to further support the efficiency of the dTtaPS-mediated internalization process. FIG. 4B shows that the polyA-tailed PNA oligomer 11 failed, as expected for a negative control, to restore luciferase activity. The successful dTtaPS-assisted delivery of the fluorescently-labeled PNA oligomers 7 and 8 in HeLa pLuc 705 cells (FIG. 11) suggests that the dTtaPS-mediated delivery of 11 should have been as successful as that of 10 under similar conditions. The PNA oligomer 12, which is 10 lacking the polyA stretch, did not restore luciferase activity, because dTtaPS failed to efficiently internalize its fluoresceinated congener 9 in HeLa pLuc 705 cells (FIG. 11). For comparability purposes, the positive control 2'-OMe RNA sequences 13 was transfected in HeLa pLuc 705 cells using Lipofectamine™ 2000 as the carrier in serum-free medium (FIG. 4B). Under these conditions, the production of luciferase activity was comparable to that produced by the dTtaPS-assisted transfection of the polyA-tailed PNA oligomer 10 in serum-containing medium. No significant luciferase activity was detected when the negative control 2'-OMe RNA sequences 14 was transfected under identical conditions (FIG. 4B). The relationship between the concentration of dTtaPS and the extent of luminescence production upon transfection of the polyA-tailed PNA oligomer 10 in HeLa pLuc 705 cells was then investigated. At a PNA oligomer concentration of 1.0 µM, luciferase activity production was found optimal when the dTtaPS concentration was in the range of 1.5-3.0 µM. Confocal microscopy analysis of the dTtaPS-assisted uptake of the fluorescently-labeled PNA oligomers 7 in HeLa pLuc 705 cells revealed that endosomal sequestration of 7 is predominant after a contact time of 12 h at 37° C. IT was also seen that PNA oligomer 7 escaped endosomal sequestration to some extent, as evidenced by nuclear fluorescence. It should be noted that our experimental protocol for confocal microscopy analysis has not been optimized. Although the dTtaPS-assisted internalization of oligomer 7 was performed over a period of 12 hours, this period of time might not have been sufficient to permit optimal release of oligomer 7 from endosomal sequestration and production of a larger number of cells with nuclear fluorescence. Furthermore, the confocal magnification of 63× instead of routine 20× was used to provide clear evidence of nuclear fluorescence at the expense of a lesser number of cells that can be viewed at this level of magnification. The results of the confocal microscopy analysis confirmed the quantitative luminescence data measured upon splicing-redirection activity triggered by dTtaPS-mediated transfection of the polyA-tailed PNA oligomer 10.

Figure 7:
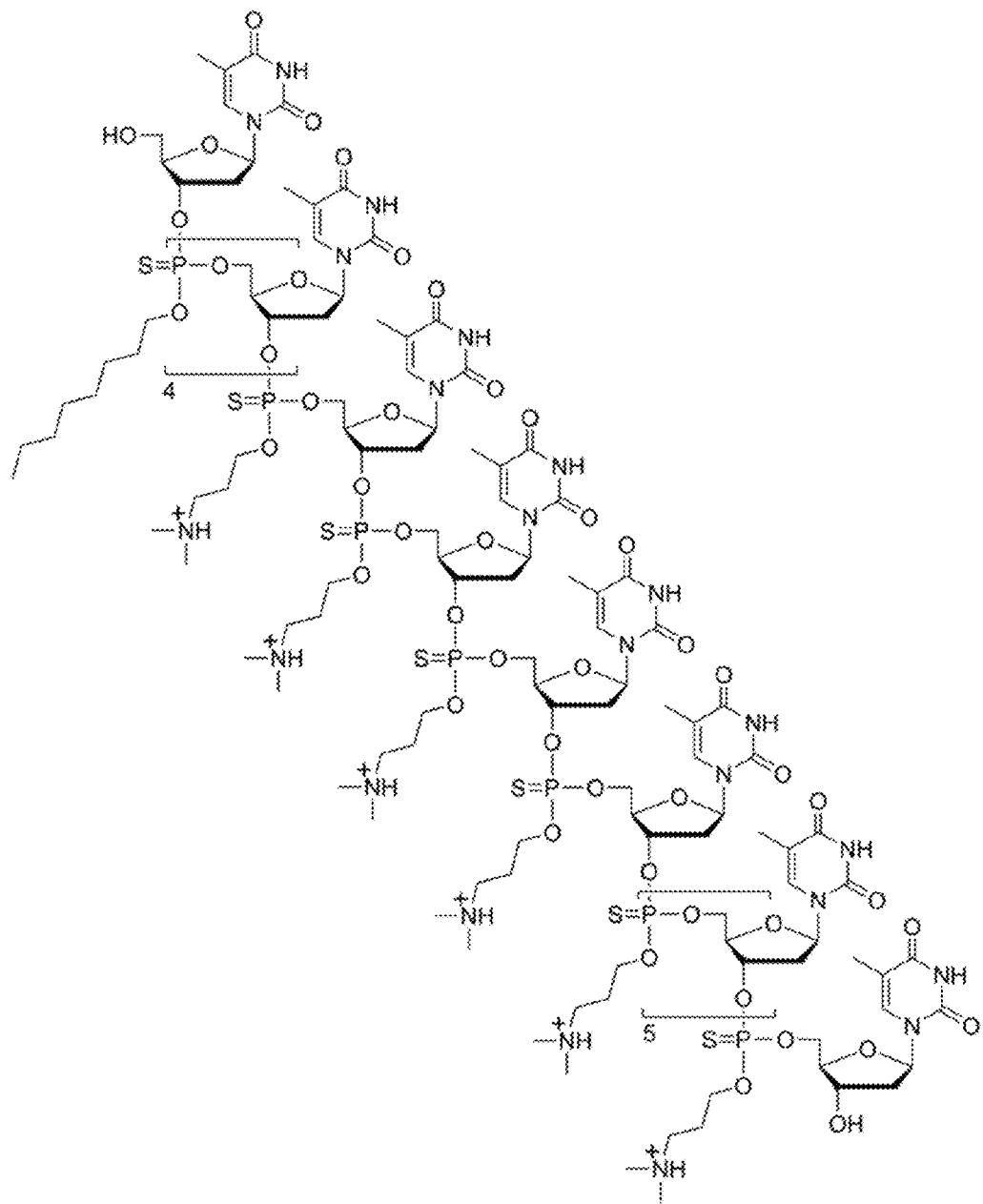
FIG. 7 presents a chemical structure of PS-dT$_{15}$[10+].
Figure 8:
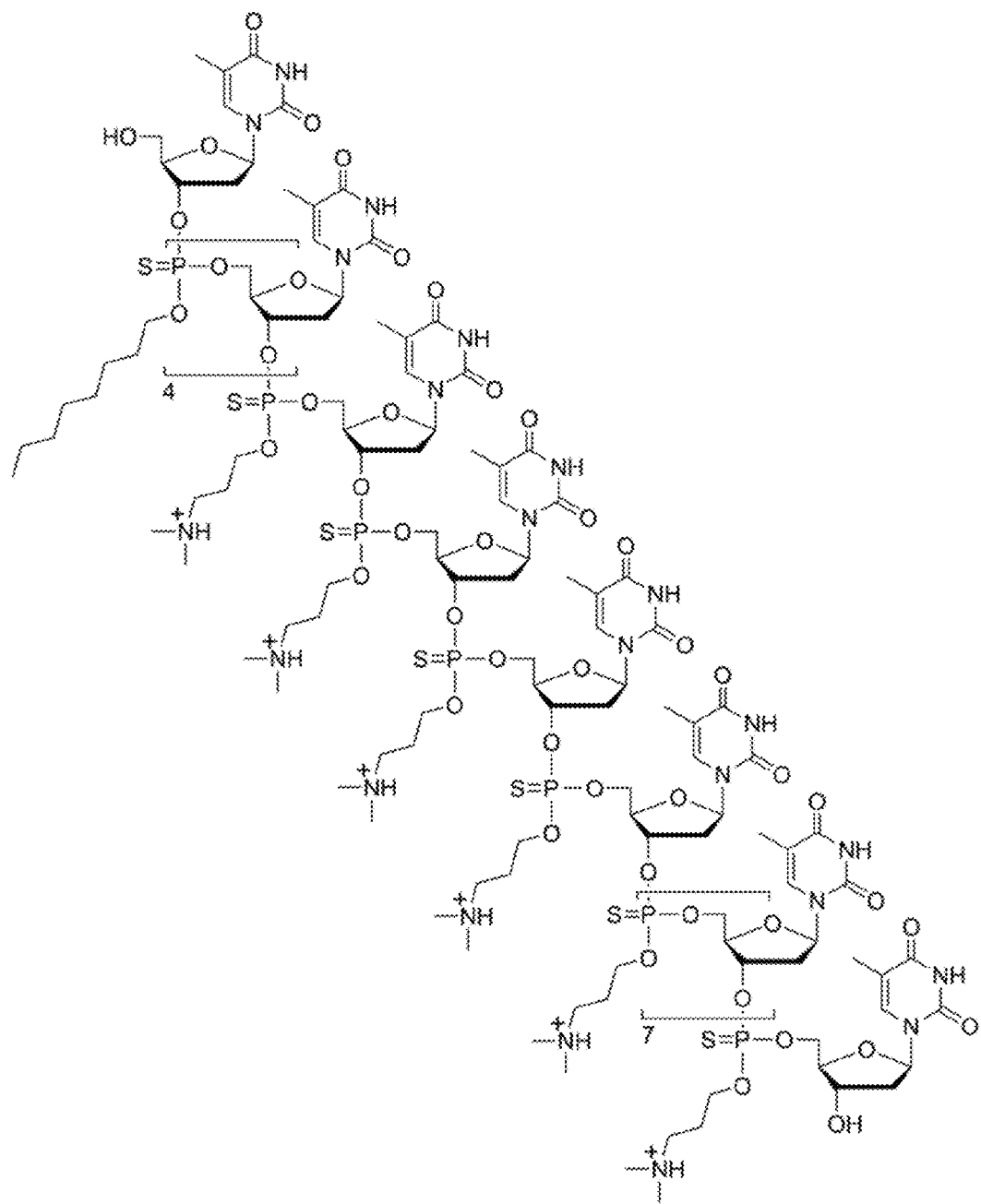
FIG. 8 presents a chemical structure of PS-dT$_{17}$[12+].

Example 7: Recognition of the PNA-polyA Stretch on the Cellular Internalization and Bioactivity of PNA Oligomers in HeLa pLuc 705 Cells The spatial arrangement and criticality of the polyA stretch of PNA oligomer 10 in terms of requirements for recognition by dTtaPS and cellular internalization were evaluated. This was achieved by moving the polyA stretch from the N-terminus of 10 to its C-terminus or replacing the polyA stretch with a polyT or a polyC stretch at the N-terminus. The consequences of these structural changes were monitored by measuring luciferase activity upon dTtaPS-mediated transfection of these modified PNA oligomers (15-17) in HeLa pLuc 705 cells. FIG. 15 shows that moving the polyA stretch from the N-terminus of 10 to its C-terminus did not significantly affect the dTtaPS-assisted transfection efficiency of PNA oligomer 17 under similar conditions. However, replacing the polyA stretch of 10 with a polyT or a polyC stretch at the N-terminus did not result in significant production of luciferase activity, presumably due to poor dTtaPS-mediated internalization of PNA oligomers 15 and 16. These findings suggest that recognition of the polyA stretch of PNA oligomer 10 by dTtaPS is necessary for its efficient cellular uptake. Interestingly, when the polyT-tailed PNA oligomer 15 is transfected in Hela pLuc 705 cells using the dAtaPS DNA element, luciferase activity production is restored to a level that is dependent on the concentration of 15 (FIG. 16). Under these conditions, about half the level of luciferase activity was obtained when compared to that produced by the dTtaPS-assisted delivery of 10 (FIG. 15). Although we cannot rule out the possibility that the dAtaPS-mediated delivery of 15 may be less efficient than the dTtaPS-assisted delivery of 10, one might argue that once internalized, cellular factors may competitively interact with the positively charged dAtaPS and allow the polyT stretch of uncharged PNA oligomer 15 to interact, by sequence complementarity, with the polyadenylated tail of cellular mRNAs. Such an interference may potentially lead to a significantly decreased concentration of 15 at the aberrant splice site of the luciferase pre-mRNA, when compared to the concentration of 10 under similar conditions. No significant level of luciferase activity was detected when dAtaPS was used for the delivery of the polyA-tailed PNA oligomer 10 (FIG. 16). These results are consistent with the recognition of the polyT stretch of PNA oligomer 15 by dAtaPS, as a critical requirement for efficient cellular uptake. As anticipated, dAtaPS failed to recognize and internalize the polyC-tailed or the polyA-tailed PNA oligomers 16 or 17, respectively, in HeLa pLuc 705 cells. The mechanism by which the polyA or polyT tail of PNA oligomers is recognized by dTtaPS or dAtaPS is unclear. Although recognition specificity appears to occur through Watson-Crick base-pairing, thermal denaturation of the dTtaPS:10 complex in PBS buffer (pH 7.4) did not produce a typical sigmoidal denaturation profile from which a melting temperature could be determined. With the objective of conclusively demonstrating that the polyA tail of PNA oligomer 10 is required for its dTtaPS-mediated internalization in HeLa pLuc 705 cells, a competition experiment was designed under which, the internalization of 10 by dTtaPS is conducted in the presence of an octathymidilyl DNA phosphorothioate oligomer (PS-dT$_8$). The affinity of PS-dT$_8$ for the polyA tail of oligomer 10 should prevent its internalization by dTtaPS to some extent and result in poorer luciferase activity production. As shown in FIG. 7, the production of luciferase activity decreased by as much as 80% relative to the control experiment performed in the absence of PS-dT$_8$. These findings strongly suggest that the recognition of polyA-tailed PNA oligomers by dTtaPS is specific and proceeds through weak base-pairing interactions considering that dTtaPS is a short DNA sequence with relatively bulky diastereomeric phosphorothioate triester functions.

Example 8: Mechanism of the dTtaPS-Assisted Internalization of PNA Oligomers in HeLa pLuc 705 Cells In order to determine whether the dTtaPS-mediated internalization of PNA oligomer 10 in HeLa pLuc 705 cells proceeded through an energy dependent mechanism, a cellular uptake experiment was carried out at 37° C. while another experiment was similarly conducted at 4° C. It was seen that when the cellular uptake experiment is carried out at 4° C., the production of luciferase activity is decreased by at least 50% relative to that measured from the experiment carried out at 37° C. These results indicate that the dTtaPS-assisted internalization of PNA oligomer 10 is in agreement with an endocytosis uptake mechanism. We then set out to identify the most probable endocytic pathway leading to the dTtaPS-mediated uptake of PNA oligomer 10. Well-documented endocytic pathway inhibitors were employed for this purpose, namely, chlorpromazine for inhibition of clathrin-coated pits-mediated endocytosis, nystatin for inhibition of caveolae-mediated endocytosis and 5-(N-ethyl-N-isopropyl) amiloride (EIPA) for inhibition of macropinocytosis. These endocytic pathway inhibitors were used at concentrations that are known to not significantly cause cell cytotoxicity. Nystatin did not inhibit luciferase production, whereas chlorpromazine and EIPA inhibited luciferase production to the extent of ~40% and ~95%, respectively. Although, the clathrin-coated pits-mediated endocytosis pathway is used to some extent for the dTtaPS-assisted internalization of PNA oligomer 10 in HeLa pLuc 705 cells, macropinocytosis clearly appears to be the prevailing endocytic pathway used for this internalization process.

Example 9: A Short PMO-polyA Stretch is Necessary and Sufficient for dTtaPS-Mediated Internalization and Bioactivity of PMO Oligomers in Live Mammalian Cells The applicability of dTtaPS to the delivery of a different class of uncharged nucleic acid sequences in several mammalian cell lines was carried out using PMO oligomers under experimental conditions similar to those used for PNA oligomers. As shown in FIG. 17, FACS analyses confirmed the dTtaPS-assisted delivery of the polyA-tailed PMO oligomers 18 and 19 in HEK 293, HeLa, HeLa pLuc 705, and SK—N—SH cell lines. The dTtaPS-assisted internalization of PMO oligomer 21 in HeLa pLuc 705 cells (FIG. 18) led to the production of luciferase activity that is about 5- to 8-fold less than that obtained with PNA oligomers at similar oligomer concentrations (FIGS. 12-13). These results suggest that dTtaPS is less competent at internalizing PMO oligomers than PNA oligomers and are in agreement with the measurements of mean fluorescence intensity (MFI) obtained from FACS analysis of the dTtaPS-mediated uptake of fluoresceinated PNA and PMO oligomer 7 and 18; the MFI determined after internalization of oligomer 7 is ~10-fold greater than that of oligomer 18. Of interest, the replacement of one PMO-A residue with a PMO-T in the polyA tail of PMO oligomer 21 did not significantly decrease the ability of dTtaPS to internalize 24 in HeLa pLuc 705 cells on the basis of luciferase activity production (FIG. 9B). Thus one A→T modification in the polyA tail of 24 is not sufficient to prevent its recognition and cellular internalization by dTtaPS. In the absence of dTtaPS, the internalization of PMO oligomer 21 is reduced to that of the negative control 22 or that of the positive control 23 lacking the polyA tail. The effect of dTtaPS concentration on the cellular uptake of PMO oligomer 21 in HeLa pLuc 705 cells was also investigated. Similar to the study performed with the PNA oligomer 10, the dTtaPS-mediated delivery of PMO oligomer 21 was found optimal, in terms of luciferase activity production, at a dTtaPS concentration in the range of 2.0-3.0 µM. Confocal microscopy analysis of the dTtaPS-assisted internalization of the fluorescently-labeled PMO oligomer 18 in HeLa pLuc 705 cells revealed endosomal sequestration of 18 and modest nuclear fluorescence, which is consistent with the level of luminescence measured upon splicing correction activity effected by dTtaPS-mediated transfection of the polyA-tailed PMO oligomer 21 (FIG. 18).

Example 10: How does the Efficiency of dTtaPS-Mediated Transfection of PNA Oligomer 10 in HeLa pLuc 705 Cells Compare with that of Lipofectamine® 2000?

A meaningful comparison could not be established, given that aside from the fact that Lipofectamine® 2000 cannot transfect the PNA oligomer 10 in the absence of a complementary negatively charged DNA sequence, the molar concentration of the cationic lipid is unknown. Although we could have conjugated a CPP to PNA oligomer 10 in order to compare the efficiency of its cellular internalization with that obtained with the trans-acting dTtaPS element, we dismissed this approach because the conjugation of a cationic CPP to a PNA oligomer is tedious and is reported to convey unpredictable physico-chemical and functional properties to the PNA.

Example 11: dTtaPS and dAtaPS Cytotoxicity Studies

The cytotoxicity of PNA oligomer 10:dTtaPS and PMO oligomer 21:dTtaPS complexes in HeLa pLuc 705 cells was evaluated over a period of 18 h using a commercial cell-counting kit. Increasing the concentration of 10 or 21 from 1.0 µM to 2.5 M while keeping the concentration of dTtaPS at 2.0 µM did not induce significant cytotoxicity when compared to that of the medium or in the absence of dTtaPS. Similarly, the cytotoxicity of dTtaPS and dAtaPS to HeLa pLuc 705 cells was found to be minimal at concentrations optimal for transfection efficiency.

Example 12: Synthesis of Oligomers

A series of oligomers of the formula $(Z)_x$ are synthesized. In the oligomers, each Z is independently selected from a 2'-deoxythymidinyl moiety, a 2'-deoxyuridinyl moiety, a 2'-deoxyadenosinyl moiety, a 2'-deoxyinosinyl moiety, a 2'-deoxycytidinyl moiety, a 5-methyl-2'-deoxycytidinyl moiety, a 7-deaza 2'-deoxyguanosinyl moiety, and a corresponding 2'-O-methyl ribonucleosidyl counterpart, in particular 2'-O-methyl uridinyl, and x is an integer from 5-20. The Z moieties are connected by thiophosphate triester linkages, 3-12 of said thiophosphate triester linkages being positively charged linkages of the formula:

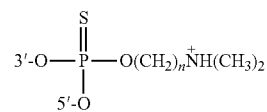

where n is an integer from 2 to 6 and the remainder of said thiophosphate triester linkages are neutral linkages of the formula:

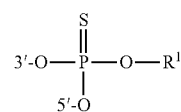

where each $R^1$ is, independently, selected from alkyl, cycloalkyl, alkenyl, cycloalkenyl, alkynyl, alkyl ether, cycloalkyl ether, alkyl thioether, cycloalkyl thioether, alkylpolyether, a nitrogen-containing or a nitrogen and oxygen-containing heterocyclic alkylyl group containing 6-28 carbons and cholesteryl. For the compositions, when x is 5-6, the number of positively charged linkages is 3, when x is 7-8, the number of positively charged linkages is 3-4, when x is 9 to 12, the number of positively charged linkages is 3-10, when x is 13 to 20, the number of positively charged linkages is 4-12. Oligomers are synthesized using standard DNA synthesis protocols. The oligomers are able to assist in transport a variety of polyA-tailed PNA or PMO oligomers into live cells.

CERTAIN EXPERIMENTAL CONCLUSIONS

The amphipathic trans-acting phosphorothioate DNA elements dTtaPS and dAtaPS are the first DNA-based transporters ever used for the delivery of uncharged nucleic acid sequences in mammalian cells. These DNA elements were easily prepared through solid-phase DNA synthesis protocols using appropriate deoxyribonucleoside phosphoramidites. dTtaPS was found to efficiently internalize polyA-tailed PNA or PMO oligomers in HEK 293, HeLa and SK—N—SH cells. The polyA stretch of either PNA or PMO oligomers is necessary and sufficient for the dTtaPS-assisted delivery of these oligomers in live cells. These findings indicate that internalization of the oligomers occurs through an energy-dependent mechanism and macropinocytosis appears to be the prevailing endocytic pathway used for cellular uptake. The recognition of polyA-tailed PNA or PMO oligomer by dTtaPS is specific and appears to occur through weak base-pairing interactions. The dTtaPS-assisted delivery of PNA oligomer 10 or PMO oligomer 21 in HeLa pLuc 705 cells enabled these oligomers to travel across the cytosol and nuclear membrane to bind to the pre-mRNA encoding luciferase and induce its correct splicing for production of luciferase activity. In the absence of the polyA stretch or when the polyA stretch is replaced with a polyT or a polyC stretch, dTtaPS failed to internalize PNA or PMO oligomers in live HeLa pLuc 705 cells and abolished the production of luciferase activity. dAtaPS was also found competent in internalizing specifically the polyT-tailed PNA oligomer 15 in HeLa pLuc 705 cells and restoring luciferase activity. Unlike commercial cationic lipids, which preferably require serum-free media for optimal transfection performance, the phosphorothioate DNA elements dTtaPS and dAtaPS performed comparably in both serum-free and serum-containing media while exhibiting little cytotoxicity at optimal transfection concentrations. Having demonstrated the proof of concept for this simple and efficient procedure for cellular internalization of uncharged nucleic acid analogues, future work will focus on broadening the use of amphipathic trans-acting phosphorothioate DNA elements for in vitro and in vivo delivery of therapeutically relevant uncharged and negatively charged nucleic acid-based drugs.

Figure 28:
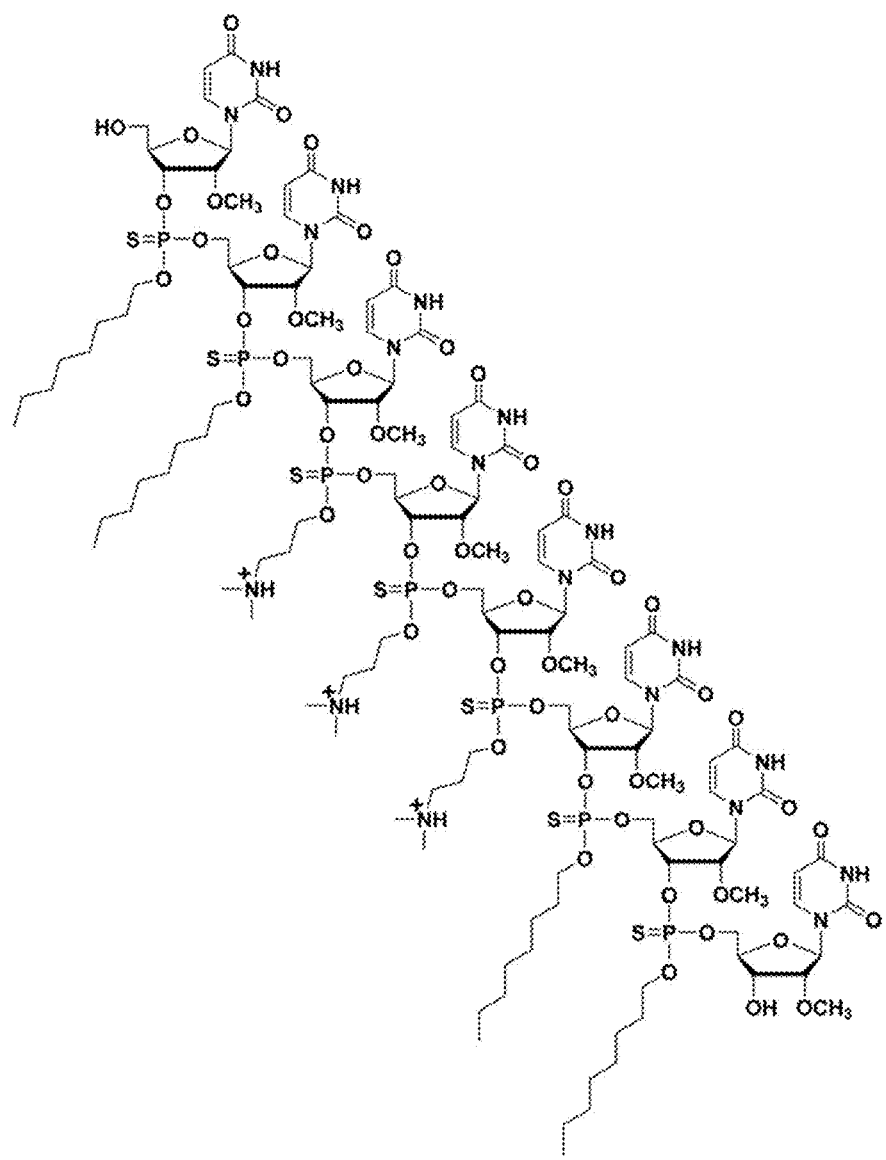
FIG. 28 presents a chemical structure of PS-2'-OMeU$_8$ [3+].

Example 13: PS-2'-OMeU$_8$[3+]-Mediated Delivery of PMOpA-SCO in HeLa pLuc 705 Cells Complex formation between PNA or PMO oligomers and dTtaPS or PS-2'-OMeU$_8$[3+]: PS-2'-OMeU$_8$[3+] is shown in FIG. 28. Appropriate amounts of PNA or PMO oligomers were solubilized in serum-free OptiMEM™ (20 μl); dTtaPS or PS-2'-OMeU$_8$[3+] was added to the solution to achieve a final concentration that is twice that of the oligomer. After a 30 min incubation at 37° C., the PNA or PMO oligomer:dTtaPS or PS-2'-OMeU$_8$[3+] complexes were stored at 4° C. for 15 minutes or until used. Stock solutions (2×) of the complexes were made by adding OptiMEM™ to appropriate volumes.

Luciferase assay protocol: HeLa pLuc 705 cells were seeded in a 96-well plate (2×10$^4$ cells/well) and allowed to grow at 37° C. for 18 h in 10% FBS-DMEM (100 μl). For each dose-dependence experiment, the culture medium of each well was replaced with either fresh serum-free (50 μl) or 20% serum-containing OptiMEM™ (50 μl) for experiments intended to be performed in serum-free or in 10% serum-containing medium. A 2× solution of PNA or PMO oligomer:dTtaPS or PS-2'-OMeU$_8$[3+] complexes in OptiMEM™ (50 μl) was added to the cells in order to achieve pre-determined complex concentrations, as indicated in the legends of relevant Figures. After a 4-hour incubation at 37° C., 20% FBS in OptiMEM™ (100 μl) was added to serum-free experiments and cells were incubated for an additional 18 h at 37° C. The culture medium was then removed by suction and the cells were lysed upon addition of the Pierce luciferase cell lysis buffer (50 μl) and mechanical agitation for 10 minutes at ambient temperature. The cell lysate (30 μl) was placed in a white 96-well plate and was followed by the addition of Bright-Glo™ reagent (20 μl); Luciferase activity was then measured using a microplate reader. For each well, luminescence was integrated over a period of 1 sec and recorded as relative light units (RLU). Luminescence measurements are reported based on the amount of total protein present in the test sample.

Figure 29:
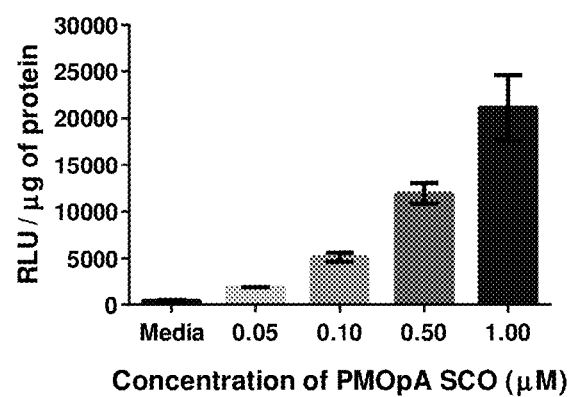
FIG. 29 shows the concentration-dependence of the 2'-OMeU$_8$[3+]-mediated delivery of PMOpA SCO sequence (PMO sequence 16, Table 1) on luciferase activity in serum-containing media. The concentration of the 2'-OMeU$_8$[3+] was kept at 2.0 μM in all experiments. Error bars represent the mean±SD of three independent experiments. RLU, relative light unit.

FIG. 29 shows the concentration-dependence of the PS-2'-OMeU$_8$[3+]-mediated delivery of PMOpA SCO sequence (PMO sequence 16, Table 1) on luciferase activity in serum-containing media.

The present disclosure may be understood more readily by reference to the following description taken in connection with the accompanying Figures and Examples, all of which form a part of this disclosure. It is to be understood that this disclosure is not limited to the specific products, methods, conditions or parameters described and/or shown herein, and that the terminology used herein is for the purpose of describing particular embodiments by way of example only and is not intended to be limiting of any claimed disclosure. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to compounds and methods of utilizing such compounds. That is, where the disclosure describes and/or claims a compound or method of use such compounds, it is appreciated that these descriptions and/or claims also describe and/or claim the devices, equipment, or systems for accomplishing these methods.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

What is claimed is:

1. A compound of the formula (Z)x wherein:

each Z is independently selected from a 2'-deoxythymidinyl moiety, a 2'-deoxyuridinyl moiety, a 2'-deoxyadenosinyl moiety, a 2'-deoxyinosinyl moiety, a 2'-deoxycytidinyl moiety, a 5-methyl-2'-deoxycytidinyl moiety, a 7-deaza 2'-deoxyguanosinyl moiety, or a corresponding 2'-O-methyl ribonucleosidyl counterpart of the 2'-deoxythymidinyl moiety, the 2'-deoxyuridinyl moiety, the 2'-deoxyadenosinyl moiety, the 2'-deoxyinosinyl moiety, the 2'-deoxycytidinyl moiety, the 5-methyl-2'-deoxycytidinyl moiety, or the 7-deaza 2'-deoxyguanosinyl moiety, x is an integer from 5-20, said Z moieties are connected by thiophosphate triester linkages, wherein 3-12 of said thiophosphate triester linkages being positively charged linkages of the formula:

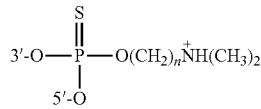

wherein n is an integer from 2 to 6, and the remainder of said thiophosphate triester linkages are neutral linkages of the formula:

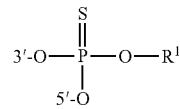

wherein each $R^1$ is $C_4$-$C_{10}$ alkyl;

provided that when x is 5-6, the number of positively charged linkages is 3, when x is 7-8, the number of positively charged linkages is 3-4, when x is 9-12, the number of positively charged linkages is 3-10, when x is 13-20, the number of positively charged linkages is 4-12.

2. The compound of claim 1, wherein n is an integer from 2 to 6.

3. The compound of claim 1, having the formula $(dT)_x$, $(dU)_x$, $(dA)_x$, $(dI)_x$, $(dC)_x$, $d(^{5\text{-}Me}C)_x$, $d(^{7\text{-}deaza}G)_x$, (2'-O-methyl U)$_x$, (2'-O-methyl A)$_x$, (2'-O-methyl C)$_x$, (2'-O-methyl $^{5\text{-}Me}$C)$_x$, (2'-O-methyl $^{5\text{-}Me}$U)$_x$ or (2'-O-methyl $^{7\text{-}deaza}$G)$_x$.

4. The compound of claim 1, wherein $R^1$ is 1-octyl and n is 3.

5. The compound of claim 1 having the formula:

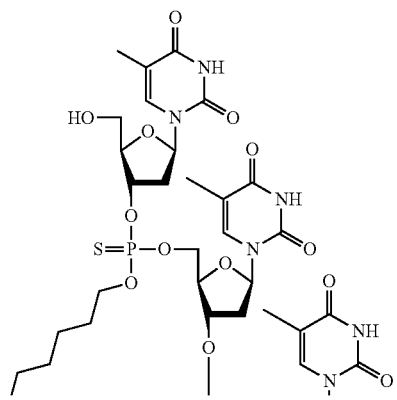

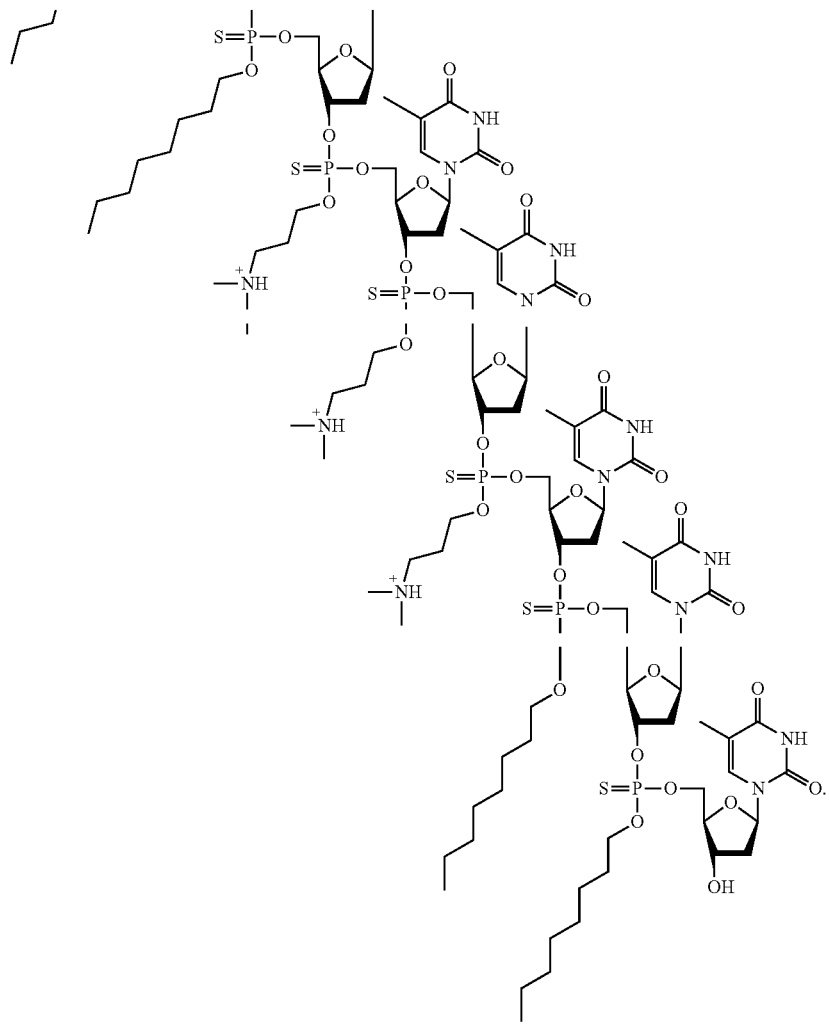

6. The compound of claim 1, having the formula:
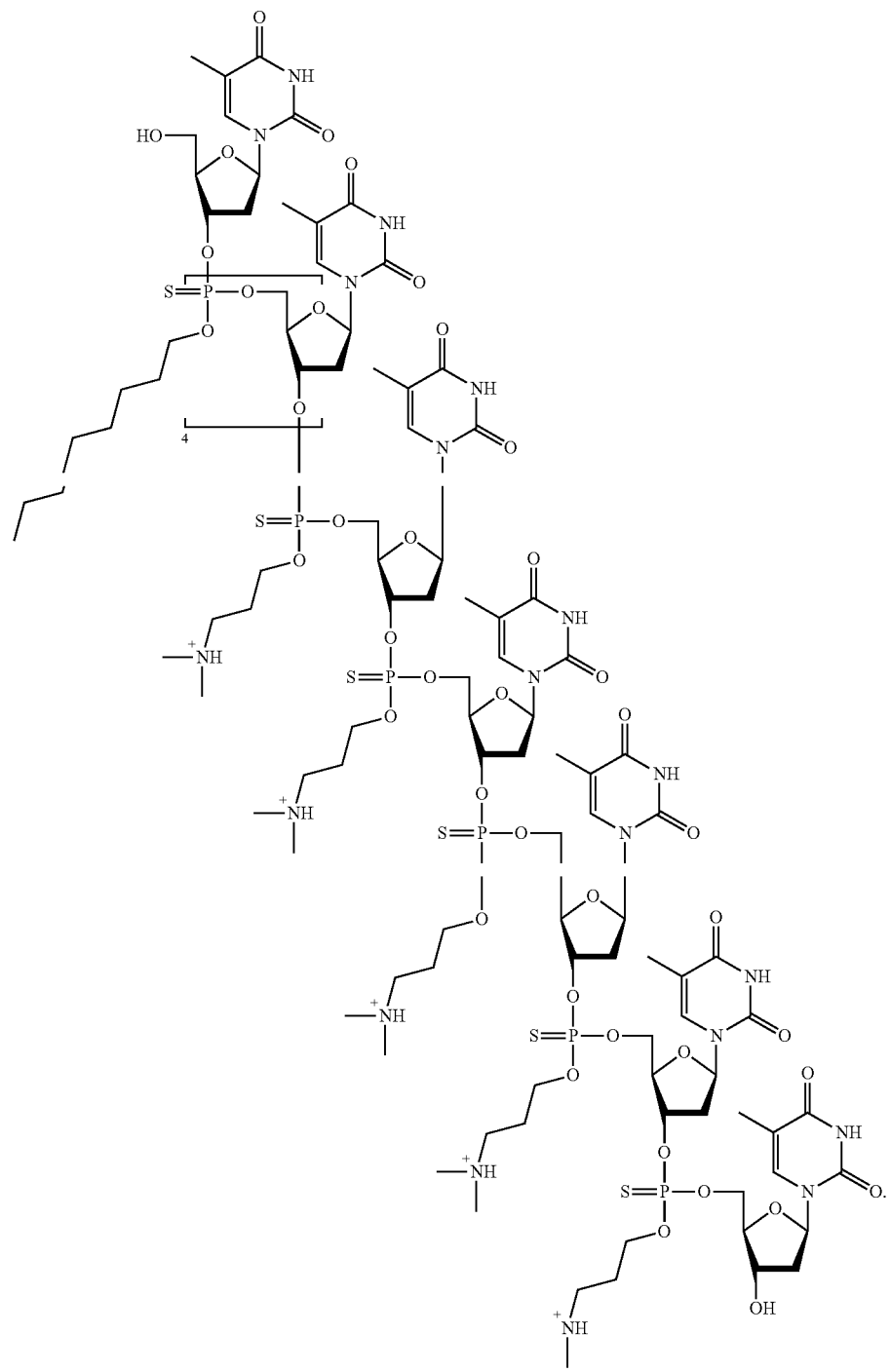

7. The compound of claim 1 having the formula:
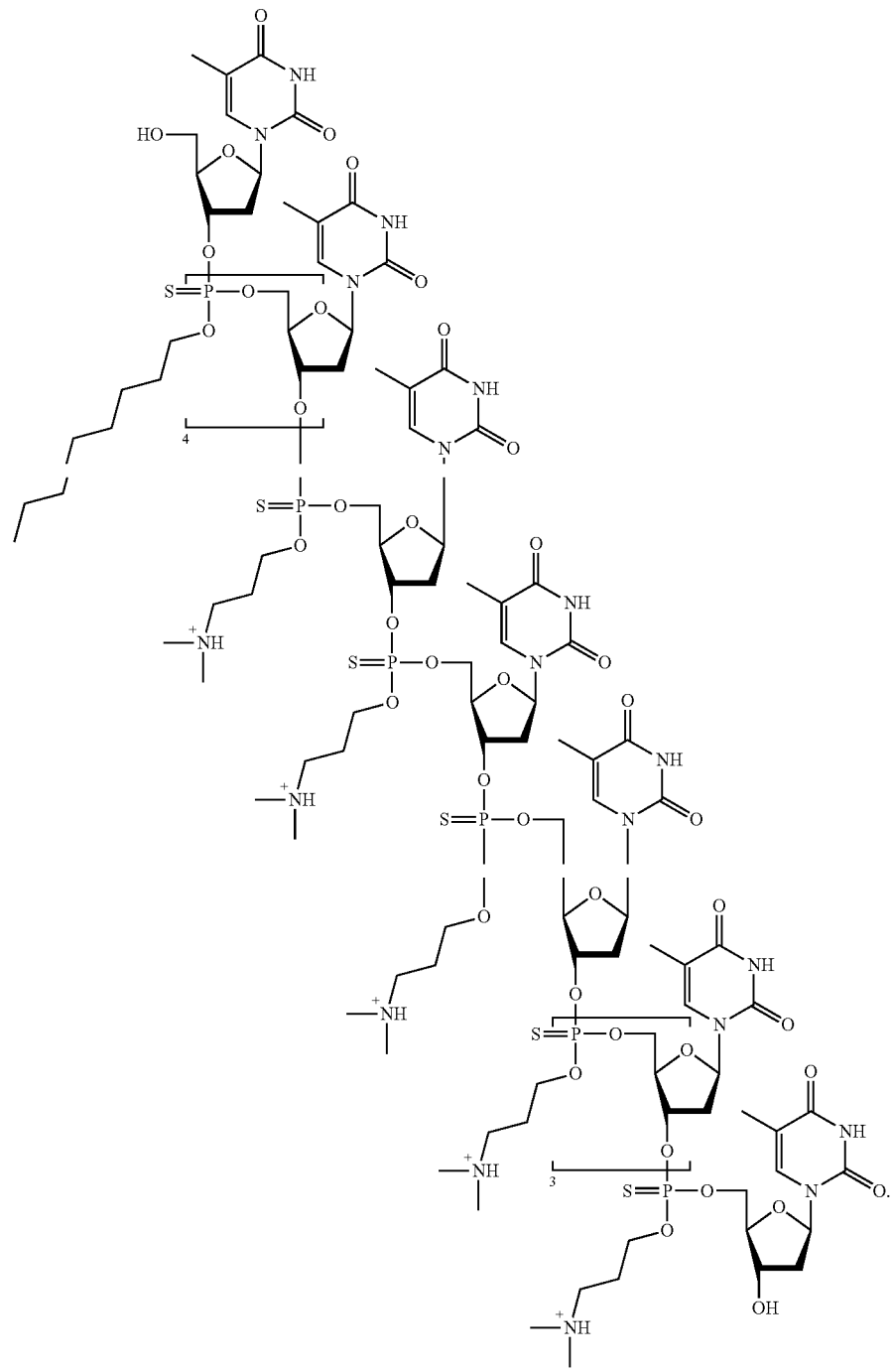

8. The compound of claim 1 having the formula:
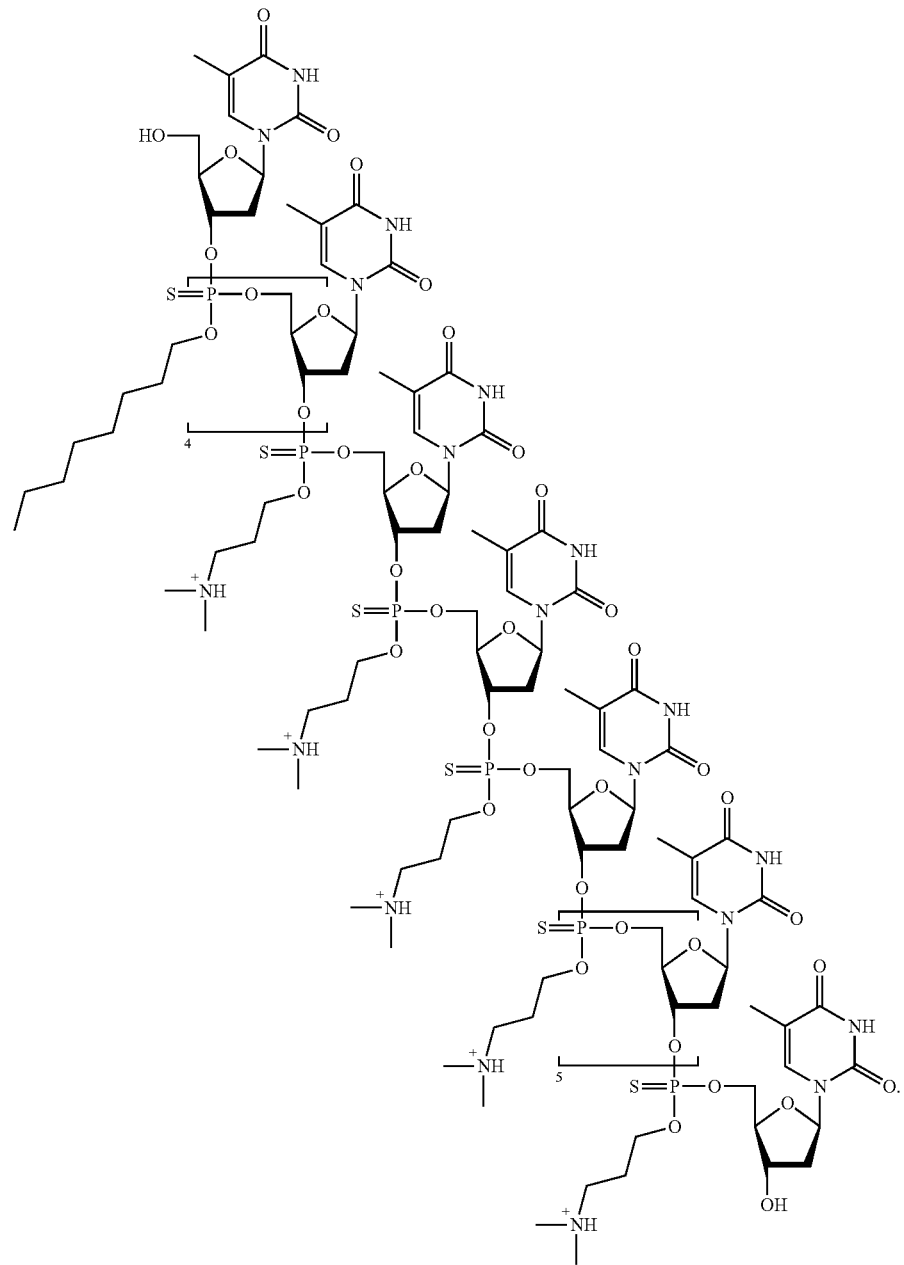

9. The compound of claim 1 having the formula:
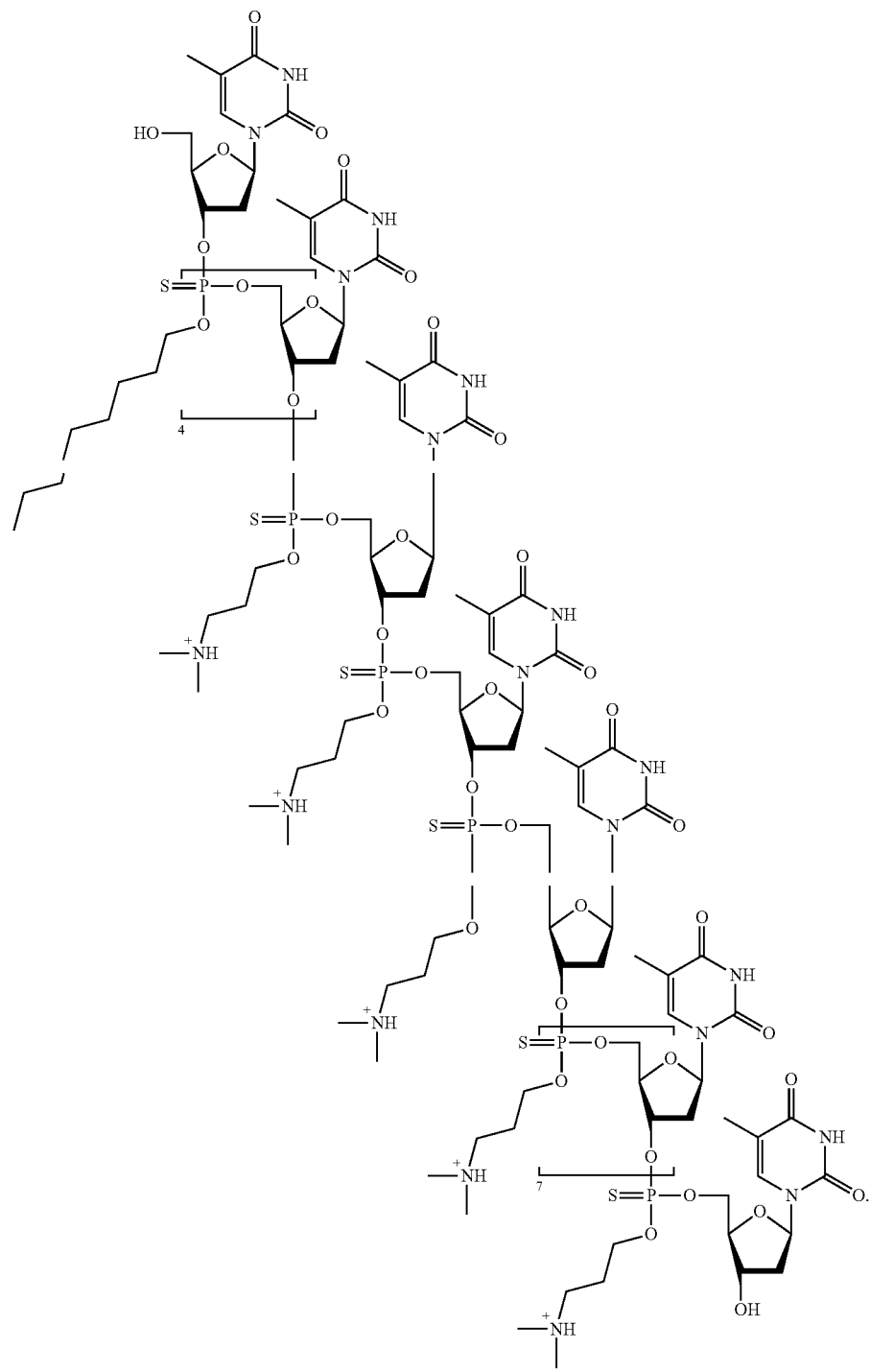

10. The compound of claim 1 having the formula:
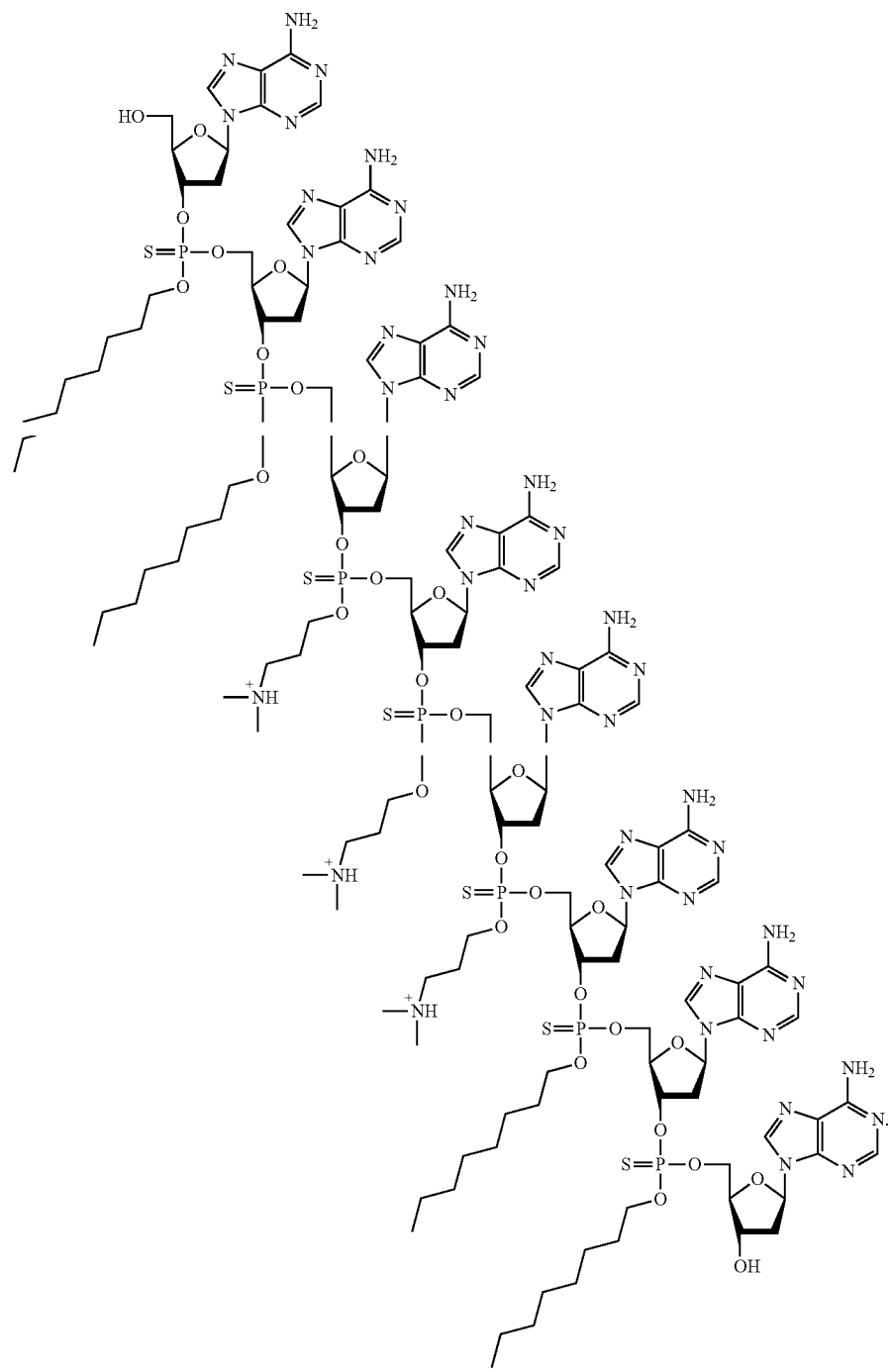 [SMILES: CCCCCCCCOP(=S)(OC[C@H]1O[C@@H](n2cnc3c(N)ncnc32)C[C@H]1OP(=S)(OCCCCCCCC)OC[C@H]1O[C@@H](n2cnc3c(N)ncnc32)C[C@H]1OP(=S)(OCCCN(C)C)OC[C@H]1O[C@@H](n2cnc3c(N)ncnc32)C[C@H]1OP(=S)(OCCCN(C)C)OC[C@H]1O[C@@H](n2cnc3c(N)ncnc32)C[C@H]1OP(=S)(OCCCN(C)C)OC[C@H]1O[C@@H](n2cnc3c(N)ncnc32)C[C@H]1OP(=S)(OCCCCCCCC)OC[C@H]1O[C@@H](n2cnc3c(N)ncnc32)C[C@H]1OP(=S)(OCCCCCCCC)OC[C@H]1O[C@@H](n2cnc3c(N)ncnc32)C[C@H]1O)O[C@@H]1C[C@H](n2cnc3c(N)ncnc32)O[C@@H]1CO]

11. The compound of claim 1 having the formula:
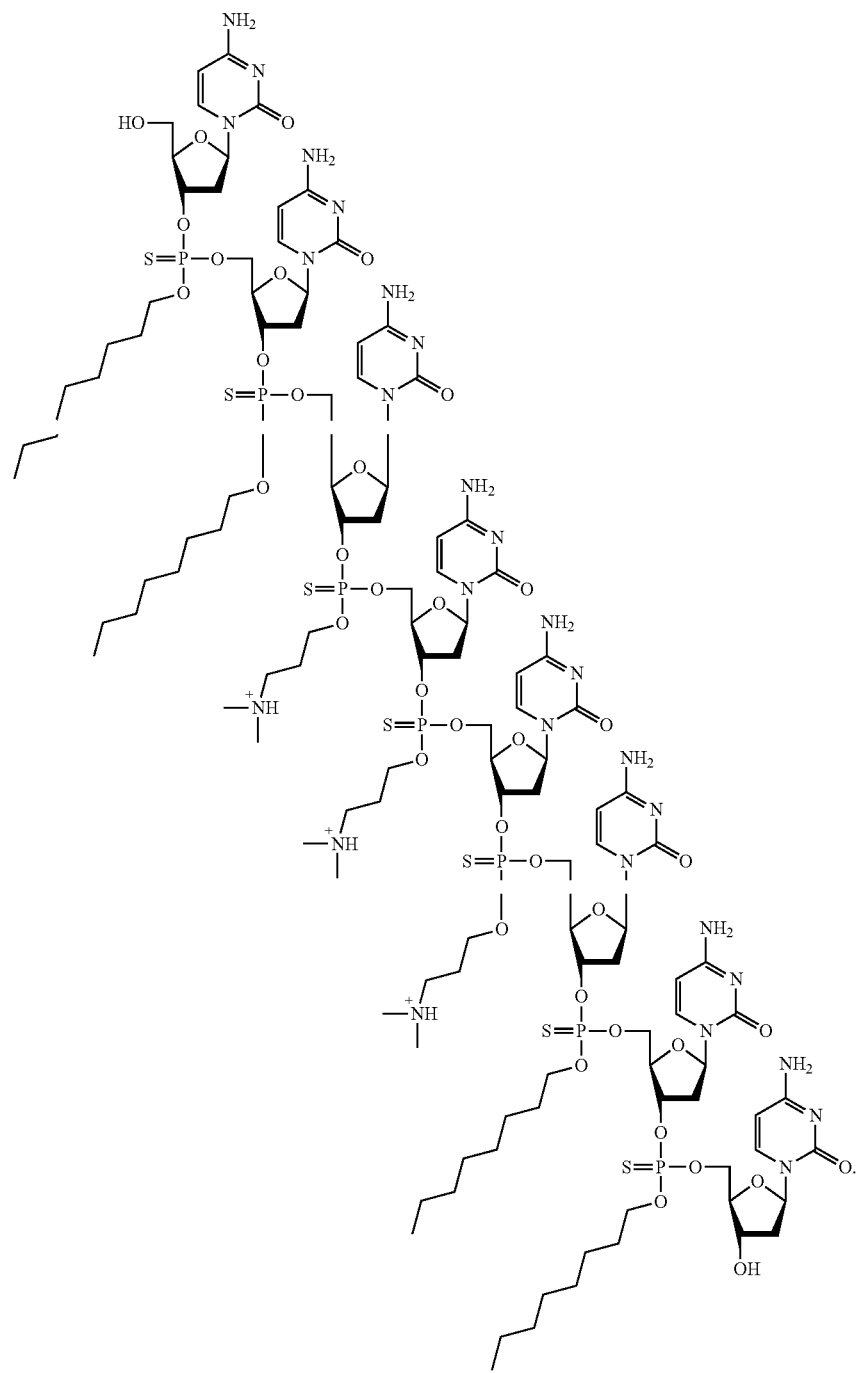 [SMILES: CCCCCCCCOP(=S)(OC[C@H]1O[C@@H](n2ccc(N)nc2=O)C[C@H]1OP(=S)(OCCCCCCCC)OC[C@H]1O[C@@H](n2ccc(N)nc2=O)C[C@H]1OP(=S)(OCCCN(C)C)OC[C@H]1O[C@@H](n2ccc(N)nc2=O)C[C@H]1OP(=S)(OCCCN(C)C)OC[C@H]1O[C@@H](n2ccc(N)nc2=O)C[C@H]1OP(=S)(OCCCN(C)C)OC[C@H]1O[C@@H](n2ccc(N)nc2=O)C[C@H]1OP(=S)(OCCCCCCCC)OC[C@H]1O[C@@H](n2ccc(N)nc2=O)C[C@H]1OP(=S)(OCCCCCCCC)OC[C@H]1O[C@@H](n2ccc(N)nc2=O)C[C@H]1O)O[C@@H]1C[C@H](n2ccc(N)nc2=O)O[C@@H]1CO]

12. The compound of claim 1 having the formula:

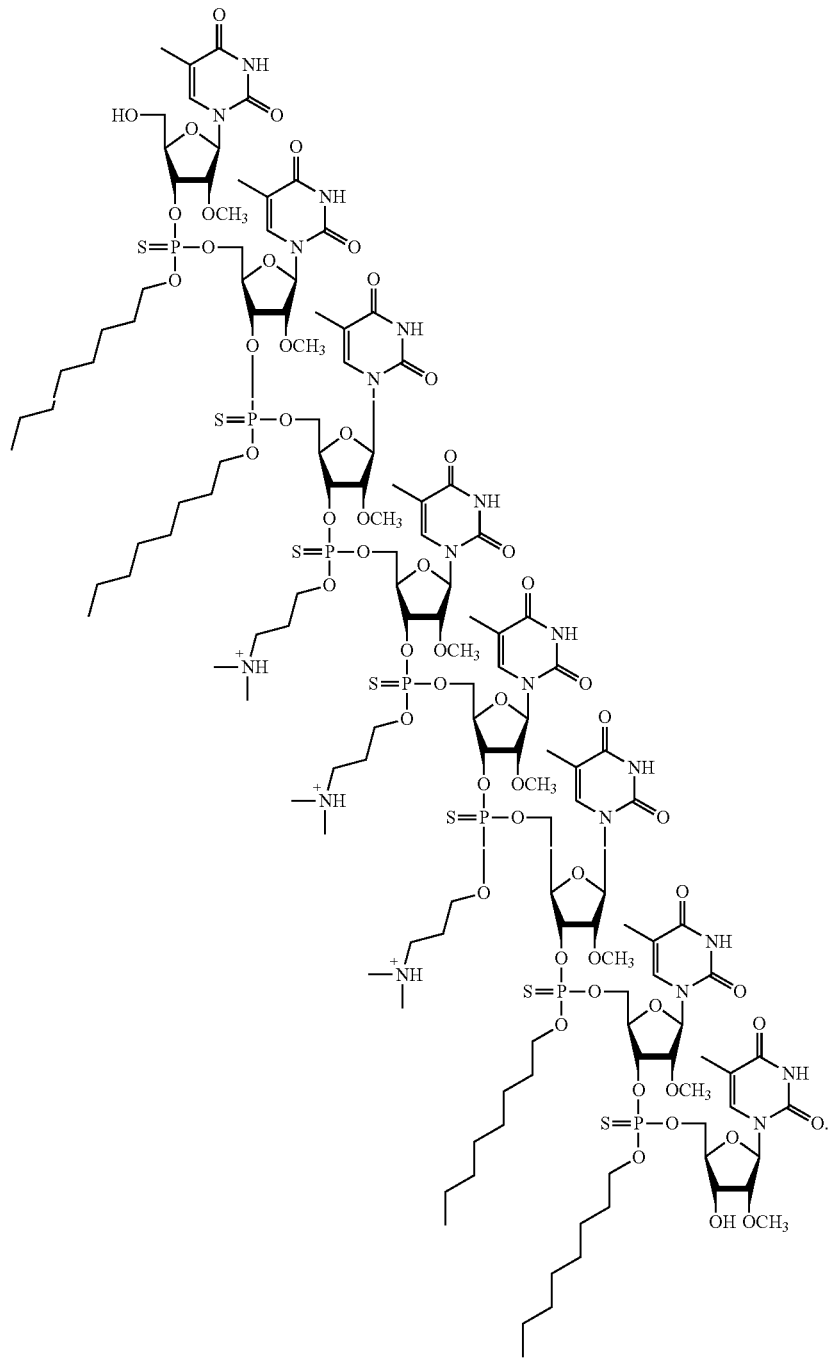

13. A method of introducing a nucleic acid into a cell by utilizing a compound of claim 1 as a transfection agent.

14. The method of claim 13, wherein said method comprises:
contacting said nucleic acid with a compound of claim 1 to form a complex; and
contacting said complex with said cell.

15. The method of claim 13, wherein said nucleic acid is uncharged.

16. The method of claim 13, wherein said nucleic acid is negatively or partially negatively charged.

17. The method of claim 13, wherein said nucleic acid is a peptide nucleic acid (PNA), a morpholino phosphorodiamidate (PMO), a xeno nucleic acid (XNA), a phosphorothioate DNA, a single- or double-stranded DNA sequence, a locked (LNA)- or unlocked (UNA)-nucleic acid, a DNA plasmid, a single- or double-stranded RNA sequence, an mRNA, a tRNA, or a short interfering (si)-, micro (mi)-, or short hairpin (sh)-RNA sequence.

18. The method of claim 13, having a threshold percentage delivery of nucleic acid to a target cell is at least 20%.

19. The method of claim 13, wherein said compound is delivered to the cell in a medium and said compound does not induce cytotoxicity of more than 15% higher than that of the medium in the absence of said compound.

20. The method of claim 13, wherein n is an integer from 2-6.

21. The method of claim 13, wherein the compound has the formula (dT), $(dU)_x$, $(dA)_x$, $(dI)_x$, $(dC)_x$, $d(^{5-Me}C)_x$, $d(^{7-deaza}G)_x$, (2'-O-methyl U)$_x$, (2'-O-methyl A)$_x$, (2'-O-methyl C)$_x$, (2'-O-methyl $^{5-Me}$C)$_x$, (2'-O-methyl $^{5-Me}$U)$_x$ or (2'-O-methyl $^{7-deaza}$G)$_x$.

22. The method of claim 13, wherein the compound is selected from

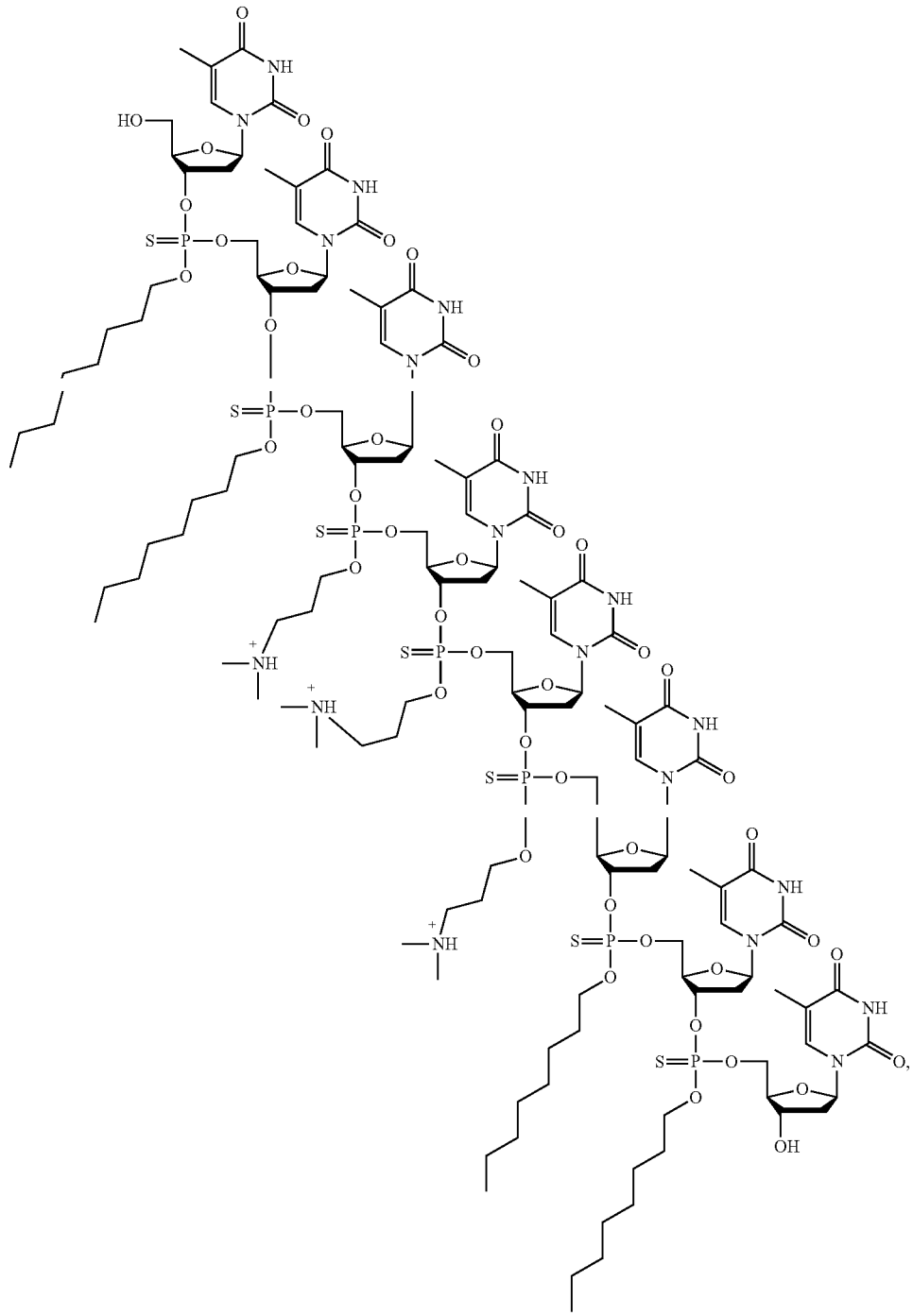

-continued
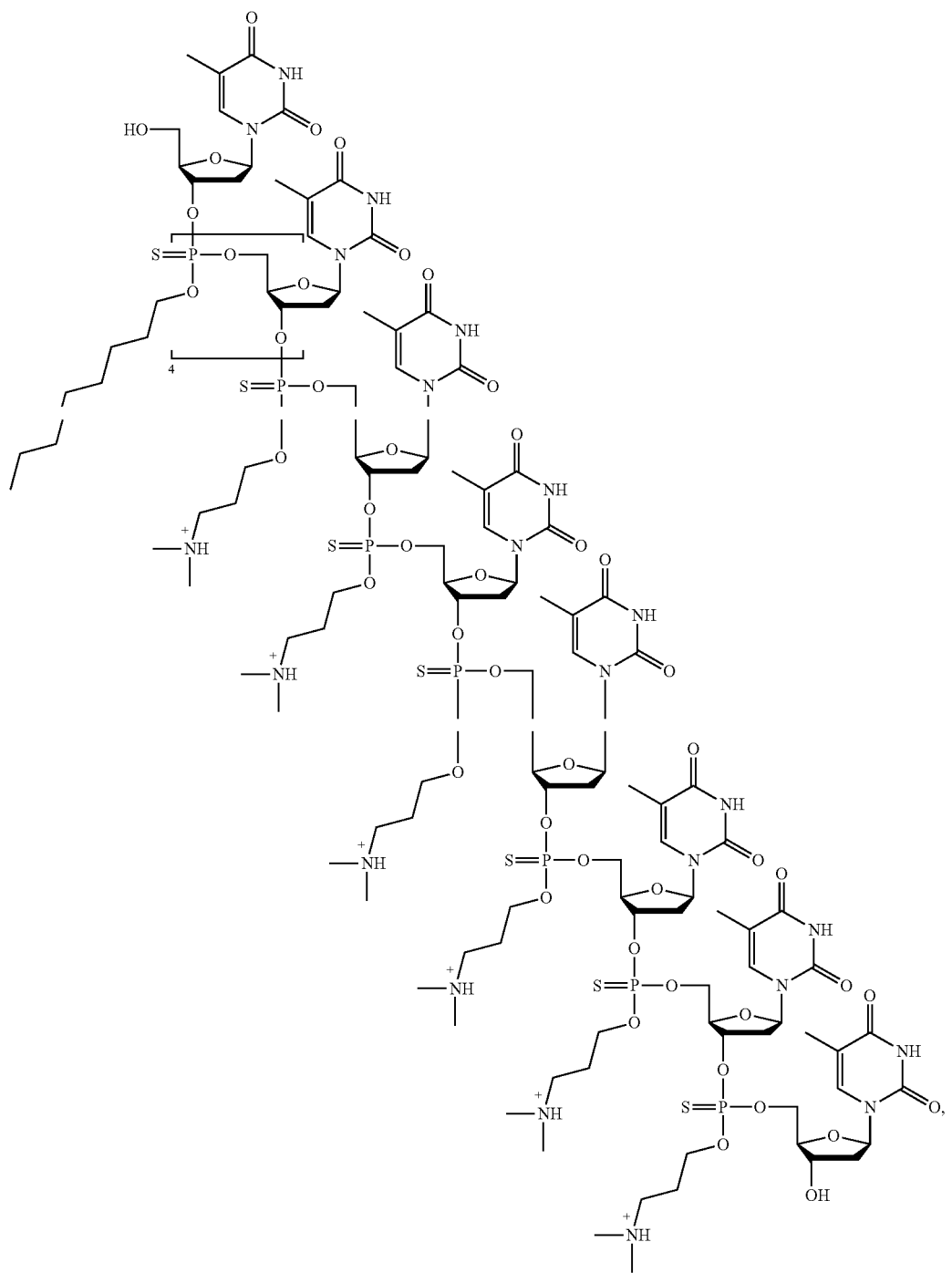

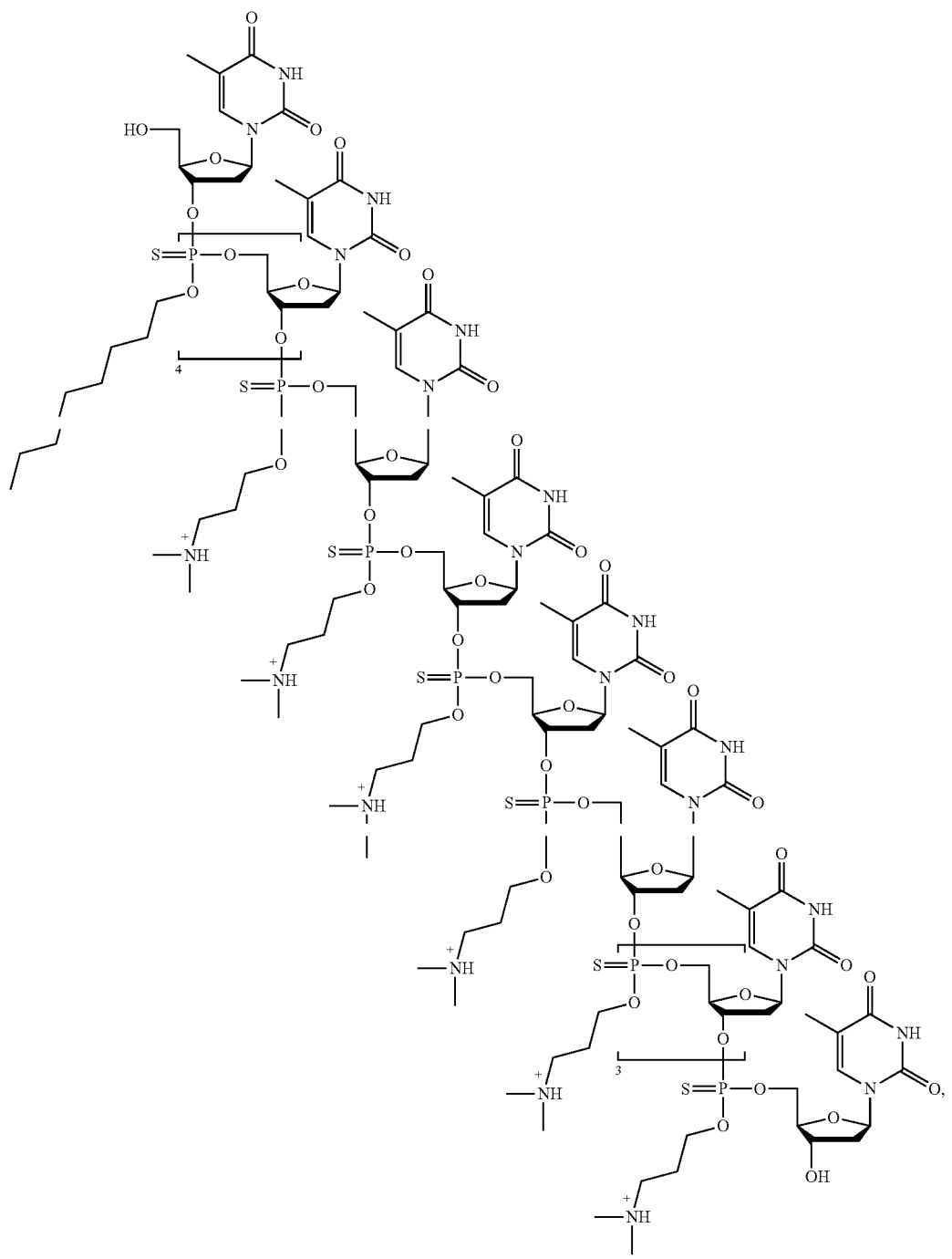

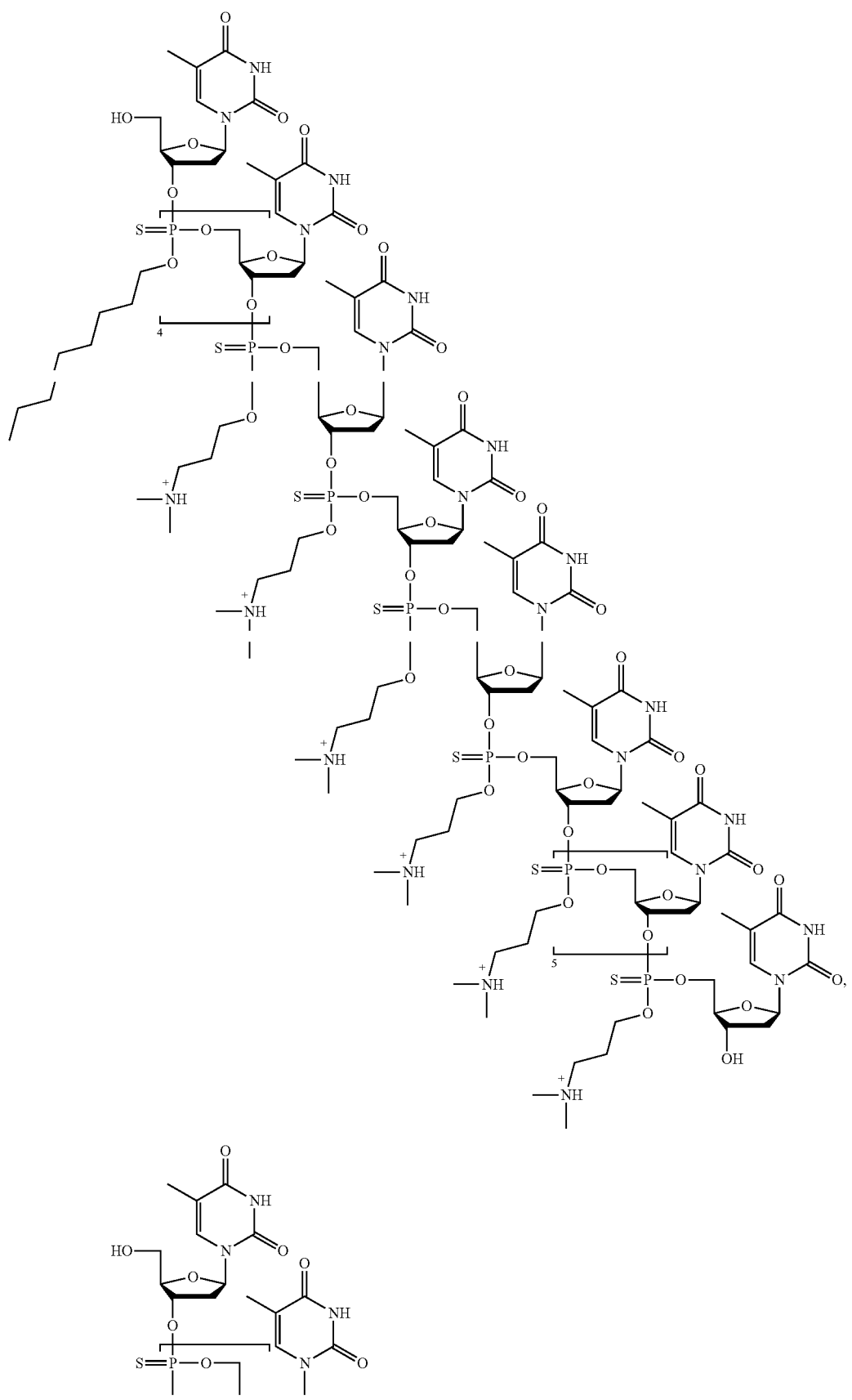

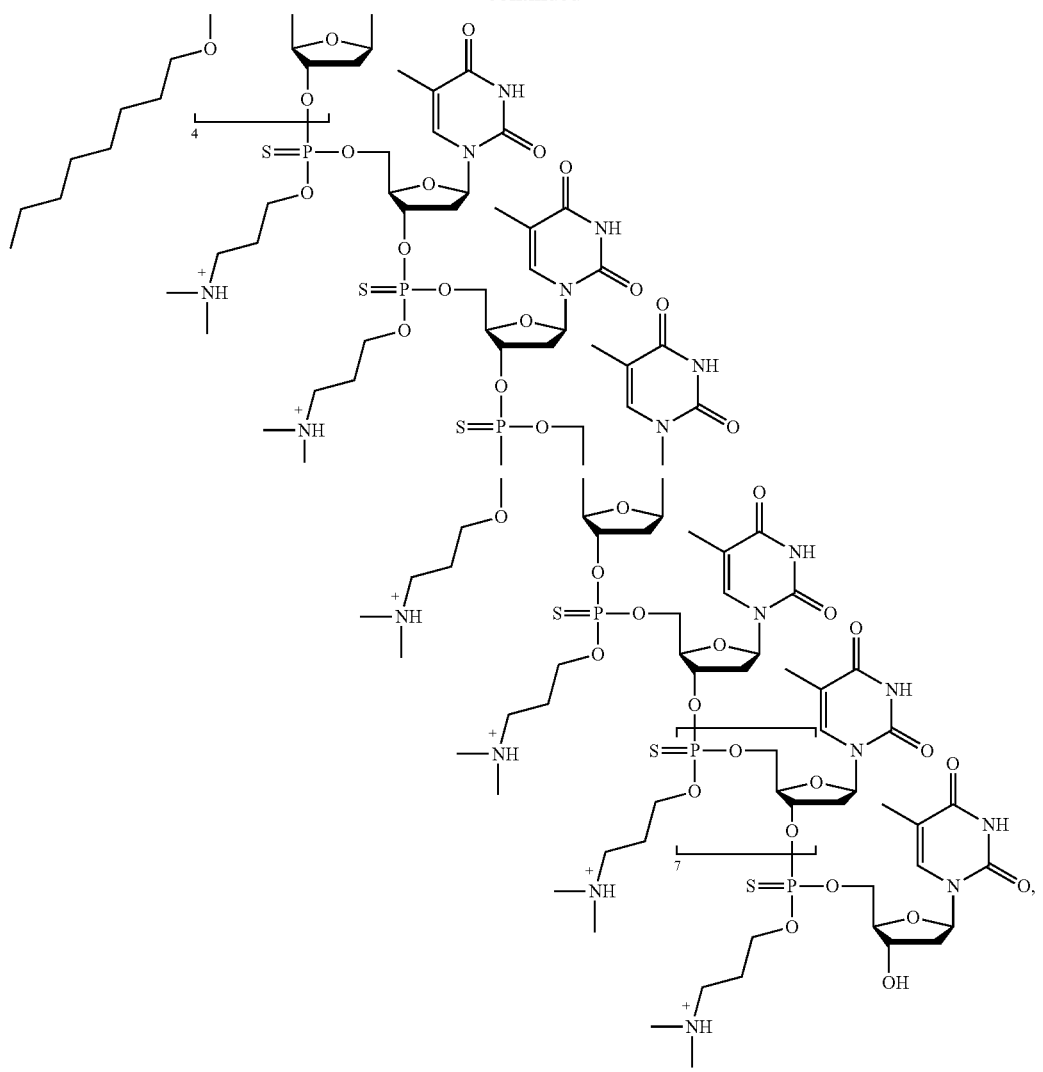
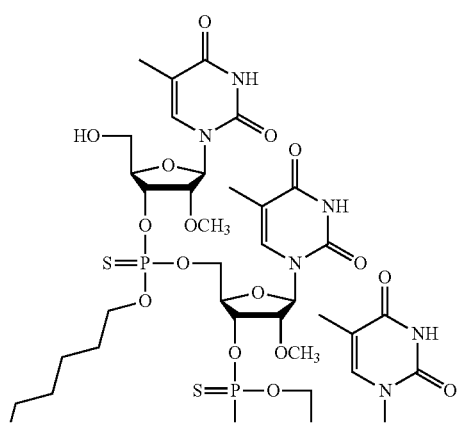

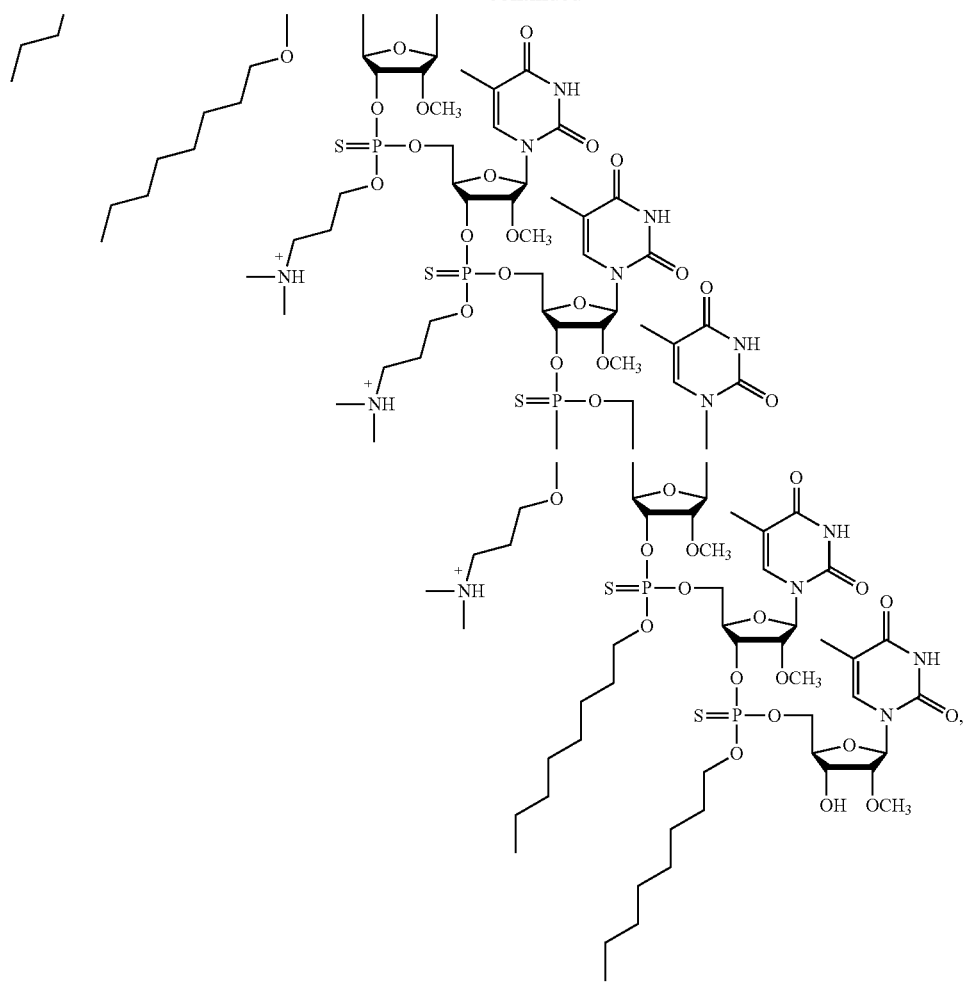
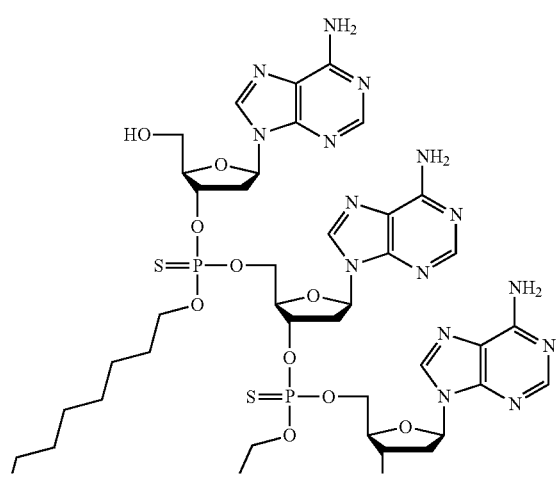

-continued
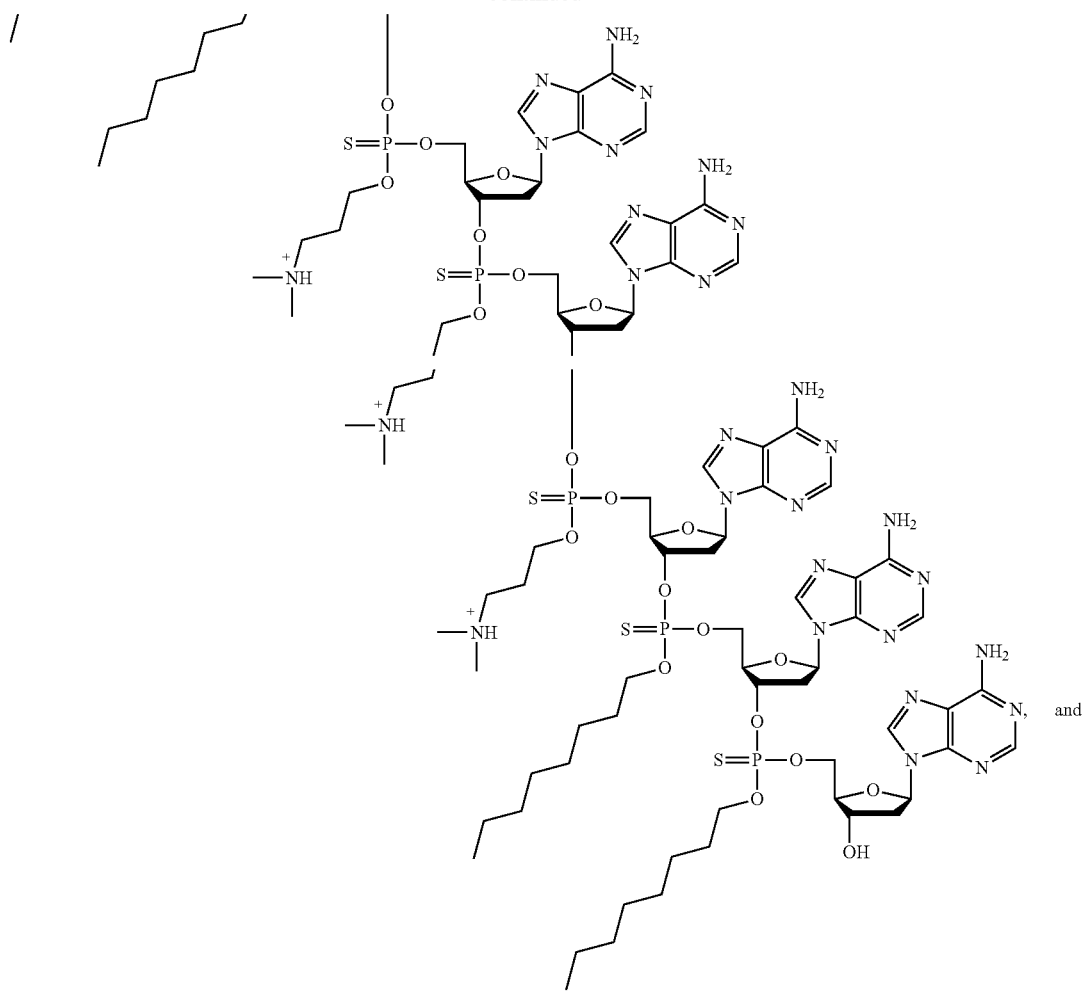
and
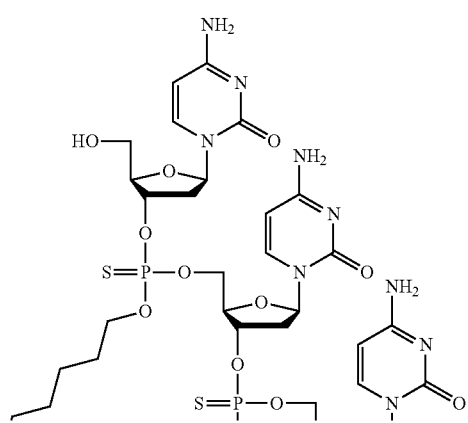

-continued
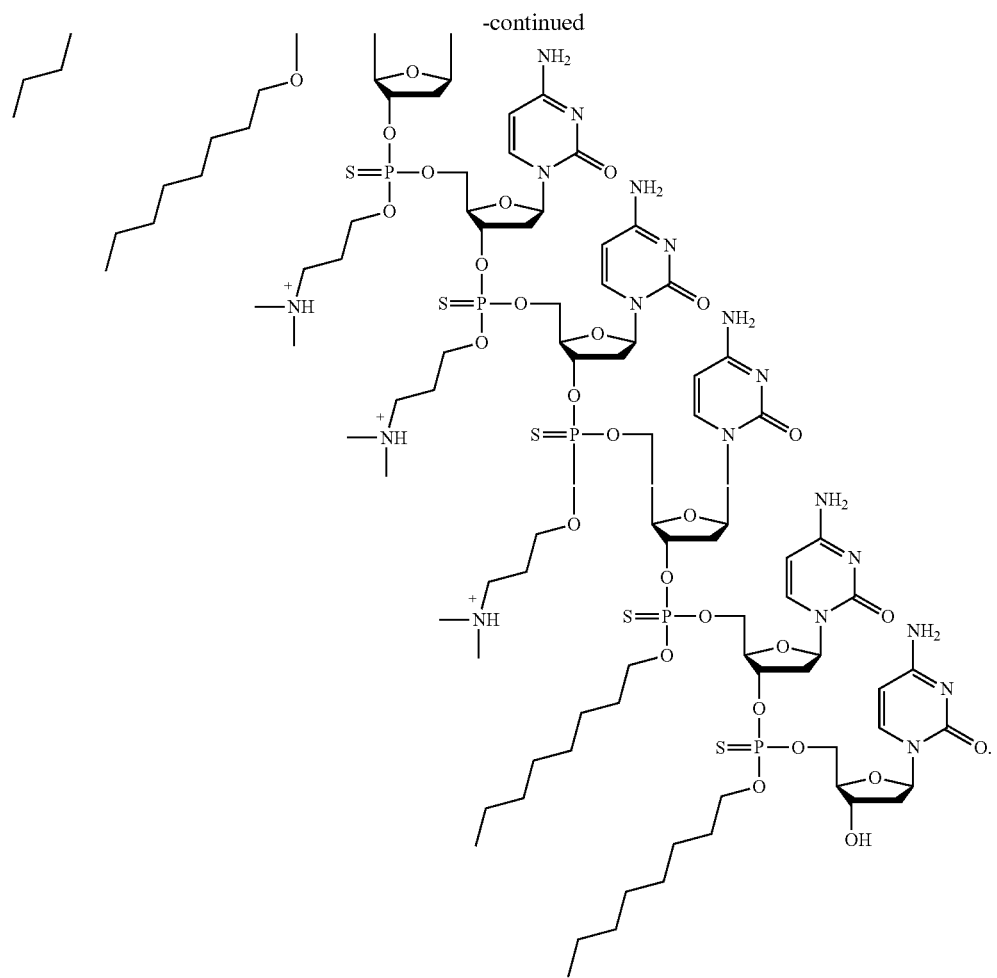
23. A kit comprising a compound of claim 1 and a nucleic acid.

SEQUENCE LISTING

```
<160> NUMBER OF SEQ ID NOS: 18

<210> SEQ ID NO 1
<211> LENGTH: 24
<212> TYPE: DNA
<213> ORGANISM: Artificial Sequence
<220> FEATURE:
<223> OTHER INFORMATION: PNA sequence

<400> SEQUENCE: 1
cctcttacct cagttacaaa aaaa                                              24

<210> SEQ ID NO 2
<211> LENGTH: 24
<212> TYPE: DNA
<213> ORGANISM: Artificial Sequence
<220> FEATURE:
<223> OTHER INFORMATION: PNA sequence

<400> SEQUENCE: 2
gtggccgttt acgtcgccaa aaaa                                              24

<210> SEQ ID NO 3
<211> LENGTH: 18
<212> TYPE: DNA
<213> ORGANISM: Artificial Sequence
<220> FEATURE:
<223> OTHER INFORMATION: PNA sequence

<400> SEQUENCE: 3
cctcttacct cagttaca                                                     18

<210> SEQ ID NO 4
<211> LENGTH: 24
<212> TYPE: DNA
<213> ORGANISM: Artificial Sequence
<220> FEATURE:
<223> OTHER INFORMATION: PNA sequence

<400> SEQUENCE: 4
cctcttacct cagttacaaa aaaa                                              24

<210> SEQ ID NO 5
<211> LENGTH: 24
<212> TYPE: DNA
<213> ORGANISM: Artificial Sequence
<220> FEATURE:
<223> OTHER INFORMATION: PNA sequence

<400> SEQUENCE: 5
gtggccgttt acgtcgccaa aaaa                                              24
```

```
<210> SEQ ID NO 6
<211> LENGTH: 18
<212> TYPE: DNA
<213> ORGANISM: Artificial Sequence
<220> FEATURE:
<223> OTHER INFORMATION: PNA sequence

<400> SEQUENCE: 6
cctcttacct cagttaca                                                       18

<210> SEQ ID NO 7
<211> LENGTH: 17
<212> TYPE: RNA
<213> ORGANISM: Artificial Sequence
<220> FEATURE:
<223> OTHER INFORMATION: 2'-OMe RNA sequence

<400> SEQUENCE: 7
ccucuuaccu caguaca                                                        17

<210> SEQ ID NO 8
<211> LENGTH: 18
<212> TYPE: RNA
<213> ORGANISM: Artificial Sequence
<220> FEATURE:
<223> OTHER INFORMATION: 2'-OMe RNA sequence

<400> SEQUENCE: 8
guggccguuu acgucgcc                                                       18

<210> SEQ ID NO 9
<211> LENGTH: 24
<212> TYPE: DNA
<213> ORGANISM: Artificial Sequence
<220> FEATURE:
<223> OTHER INFORMATION: PNA sequence

<400> SEQUENCE: 9
cctcttacct cagttacatt tttt                                                24

<210> SEQ ID NO 10
<211> LENGTH: 24
<212> TYPE: DNA
<213> ORGANISM: Artificial Sequence
<220> FEATURE:
<223> OTHER INFORMATION: PNA sequence

<400> SEQUENCE: 10
cctcttacct cagttacacc cccc                                                24

<210> SEQ ID NO 11
<211> LENGTH: 24
<212> TYPE: DNA
<213> ORGANISM: Artificial Sequence
<220> FEATURE:
```

<223> OTHER INFORMATION: PNA sequence

<400> SEQUENCE: 11
aaaaaacctc ttacctcagt taca                                    24

<210> SEQ ID NO 12
<211> LENGTH: 24
<212> TYPE: DNA
<213> ORGANISM: Artificial Sequence
<220> FEATURE:
<223> OTHER INFORMATION: PMO sequence

<400> SEQUENCE: 12
cctcttacct cagttacaaa aaaa                                    24

<210> SEQ ID NO 13
<211> LENGTH: 24
<212> TYPE: DNA
<213> ORGANISM: Artificial Sequence
<220> FEATURE:
<223> OTHER INFORMATION: PMO sequence

<400> SEQUENCE: 13
gtggccgttt acgtcgccaa aaaa                                    24

<210> SEQ ID NO 14
<211> LENGTH: 18
<212> TYPE: DNA
<213> ORGANISM: Artificial Sequence
<220> FEATURE:
<223> OTHER INFORMATION: PMO sequence

<400> SEQUENCE: 14
cctcttacct cagttaca                                           18

<210> SEQ ID NO 15
<211> LENGTH: 24
<212> TYPE: DNA
<213> ORGANISM: Artificial Sequence
<220> FEATURE:
<223> OTHER INFORMATION: PMO sequence

<400> SEQUENCE: 15
cctcttacct cagttacaaa aaaa                                    24

<210> SEQ ID NO 16
<211> LENGTH: 24
<212> TYPE: DNA
<213> ORGANISM: Artificial Sequence
<220> FEATURE:
<223> OTHER INFORMATION: PMO sequence

<400> SEQUENCE: 16
gtggccgttt acgtcgccaa aaaa                                    24

<210> SEQ ID NO 17
<211> LENGTH: 18
<212> TYPE: DNA
<213> ORGANISM: Artificial Sequence
<220> FEATURE:
<223> OTHER INFORMATION: PMO sequence

<400> SEQUENCE: 17
cctcttacct cagttaca                                           18

```
<210> SEQ ID NO 18
<211> LENGTH: 24
<212> TYPE: DNA
<213> ORGANISM: Artificial Sequence
<220> FEATURE:
<223> OTHER INFORMATION: PMO sequence

<400> SEQUENCE: 18
cctcttacct cagttacaaa taaa                                            24
```